US010167470B2

(12) United States Patent
Collin et al.

(10) Patent No.: US 10,167,470 B2
(45) Date of Patent: Jan. 1, 2019

(54) ANTISENSE OLIGONUCLEOTIDES FOR THE TREATMENT OF LEBER CONGENITAL AMAUROSIS

(71) Applicant: STICHTING KATHOLIEKE UNIVERSITEIT, Nijmegen (NL)

(72) Inventors: Robert Wilhelmus Johanna Collin, Venlo (NL); Franciscus Peter Maria Cremers, Malden (NL); Antonia Ingrid Den Hollander, Groesbeek (NL)

(73) Assignee: STICHTING KATHOLIEKE UNIVERSITEIT, Nijmegen (NL)

( * ) Notice: Subject to any disclaimer, the term of this patent is extended or adjusted under 35 U.S.C. 154(b) by 0 days.

(21) Appl. No.: 15/963,229

(22) Filed: Apr. 26, 2018

(65) Prior Publication Data

US 2018/0305692 A1  Oct. 25, 2018

Related U.S. Application Data

(63) Continuation of application No. 15/656,635, filed on Jul. 21, 2017, which is a continuation of application No. 14/342,776, filed as application No. PCT/NL2012/050275 on Apr. 25, 2012, now Pat. No. 9,771,580.

(60) Provisional application No. 61/531,137, filed on Sep. 6, 2011.

(30) Foreign Application Priority Data

Sep. 5, 2011 (NL) ..................................... 2007351

(51) Int. Cl.
C12N 15/113 (2010.01)
(52) U.S. Cl.
CPC ........ C12N 15/113 (2013.01); C12N 2310/11 (2013.01); C12N 2310/15 (2013.01); C12N 2310/321 (2013.01); C12N 2310/346 (2013.01); C12N 2320/33 (2013.01); C12N 2320/34 (2013.01)
(58) Field of Classification Search
None
See application file for complete search history.

(56) References Cited

U.S. PATENT DOCUMENTS

| 7,517,644 B1 | 4/2009 | Smith |
| 9,487,782 B2 | 11/2016 | Rozet et al. |
| 2005/0118625 A1 | 6/2005 | Mounts |
| 2005/0233455 A1 | 10/2005 | Damha et al. |
| 2009/0269755 A1 | 10/2009 | Aartsma-Rus et al. |
| 2012/0108654 A1 | 5/2012 | Campochiaro |

FOREIGN PATENT DOCUMENTS

| WO | WO 2009/121536 | 10/2009 |
| WO | WO 2012/168435 | 12/2012 |

OTHER PUBLICATIONS

Baala, et al. "Pleiotropic effects of CEP290 (NPHP6) mutations extend to Meckel syndrome", Am J Hum Genet (2007) vol. 81, 170-179.
Bainbridge, et al. "Effect of gene therapy on visual function in Leber's congenital amaurosis", N Engl J Med (2008) vol. 358, 2231-2239.
Baye, "Then-Terminal Region of Centrosomal Protein 290 (CEP290) Restores Vision in a Zebrafish Model of Human Blindness", Human Molecular Genetics, vol. 20, No. 8, Apr. 15, 2011, pp. 1467-1477.
Cideciyan et al., "Centrosomai-Ciliary Gene CEP290/NPHP6 Mutations Result in Blindness with Unexpected Sparing of Photoreceptors and Visual Brain: Implications for Therapy of Leber Congenital Amaurosis", Human Mutation, vol. 28, No. 11, Nov. 1, 2007, pp. 1074-1083.
Cideciyan, et al. "Human gene therapy for RPE65 isomerase deficiency activates the retinoid cycle of vision but with slow rod kinetics", Proc Natl Acad Sci (2008) vol. 105, 15112-15117.
Collin et al, "Antisense Oligonucleotide (AON-based Therapy for CEP290-Associated LCA", ARVO, May 3, 2011.
Collin et al., "Antisense oligonucleotide (AON)-based therapy for CEP290-associated LCA." Poster presented at: ARVO Annual Meeting, May 3, 2011, Program No. 3324, Poster No. A572.
Coppieters, et al. "Genetic screening of LCA in Belgium: predominance of CEP290 and identification of potential modifier alleles in AH 11 of CEP290-related phenotypes", Hum Mutat (2010) vol. 31, E1709-E1766.
Den Hollander et al., "Mutations in the CEP290 (NPHP6) Gene are a Frequent Cause of Leber Congenital Amaurosis", American Journal of Human Genetics, American Society of Human Genetics,vol. 79, No. 3, Sep. 1, 2006, pp. 556-561.
Den Hollander, et al. "Leber congenital amaurosis: genes, proteins and disease mechanisms",Prog Retin Eye Res (2008) vol. 27,391-419.
Den Hollander, et al. "Lighting a candle in the dark: advances in genetics and gene therapy of recessive retinal dystrophies", J Clin Invest (2010) vol. 120, 3042-3053.
Estrada-Cuzcano, et al. "IQCB1 mutations in patients with leber congenital amaurosis", Invest Ophthalmol Vis Sci (2011) vol. 52, 834-839.
Gerard et al, "Antisense Oligonucleotide-Mediated Exon Skipping Restores Primary Cilia Assembly in Fibroblasts Harbouring the Common LCA CEP290 Mutation", Aug. 31, 2011.
Gerard et al., "AON-Mediated Exon Skipping Restores Ciliation in Fibroblasts Harboring the Common Leber Congenital Amaurosis CEP290 Mutation", American Society of Gene & Cell Therapy,Molecular Therapy-Nucleic Acids, vol. 1, Jun. 26, 2012, DOI: 10.1038/mtna.2012.21.

(Continued)

Primary Examiner — Jennifer Pitrak McDonald
(74) Attorney, Agent, or Firm — McDonnell Boehnen Hulbert & Berghoff LLP

(57) ABSTRACT

The present invention relates to the fields of medicine and immunology. In particular, it relates to novel antisense oligonucleotides that may be used in the treatment, prevention and/or delay of Leber congenital amaurosis.

11 Claims, 5 Drawing Sheets
Specification includes a Sequence Listing.

(56) References Cited

OTHER PUBLICATIONS

Hauswirth, et al. "Phase I Trial of Leber Congenital Amaurosis due to Estrada-Mutations by OcularSubretinal Injection of Adena-Associated Virus Gene Vector: Short-Term Results", Hum Gene Ther,Oct. 2008, vol. 19, pp. 979-990.
Helou, et al. "Mutation analysis of NPHP6/CEP290 in patients with Joubert syndrome and Senior-Loken syndrome", J Med Genet (2007) vol. 44, 657-663.
International Search Report in PCT/NL2012/050275 dated Aug. 28, 2012.
Koenekoop, et al. "Genetic testing for retinal dystrophies and dysfunctions: benefits, dilemmas and solutions", Clin Experiment Ophthalmol (2007) vol. 35, 473-485.
Lan Franchi et al., "Identification of 4370 expressed sequence tags from a 3'-end-specific cDNA library of human skeletal muscle by DNA sequencing and filter hybridization", Genome Research, 1996, vol. 6.1, pp. 35-42.
Leber "Uber Retinitis Pigmentosa and angeborene Amaurose", von Graefe's Archives Ophthalmology(1869) vol. 15, pp. 1-25.
Littink, et al. "A novel nonsense mutation in CEP290 induces exon skipping and leads to a relatively mild retinal phenotype", Invest Ophthalmol Vis Sci (201 0) Vo. 51, 3646-3652.
Maguire, et al. "Age-dependent effects of RPE65 gene therapy for Leber's congenital amaurosis: a phase 1 dose-escalation trial", Lancet (2009) vol. 374, 1597-1605.
Maguire, et al. "Safety and efficacy of gene transfer for Leber's congenital amaurosis", N Engl J Med (2008) vol. 358, 2240-2248.
Perrault, et al. "Spectrum of NPHP6/CEP290 mutations in Leber congenital amaurosis and delineation of the associated phenotype", Hum Mutat (2007), vol. 28, 416.
Stone "Leber congenital amaurosis—a model for efficient genetic testing of heterogeneous disorders: LXIV Edward Jackson Memorial Lecture", Am J Ophthalmol (2007) vol. 144, 791-811.
Valente, et al. "Mutations in CEP290, which encodes a centrosomal protein, cause pleiotropic forms of Joubert syndrome", Nat Genet (2006) vol. 38, 623-625.

A Wild-type CEP290

B LCA mutant CEP290

C LCA mutant CEP290 + AON

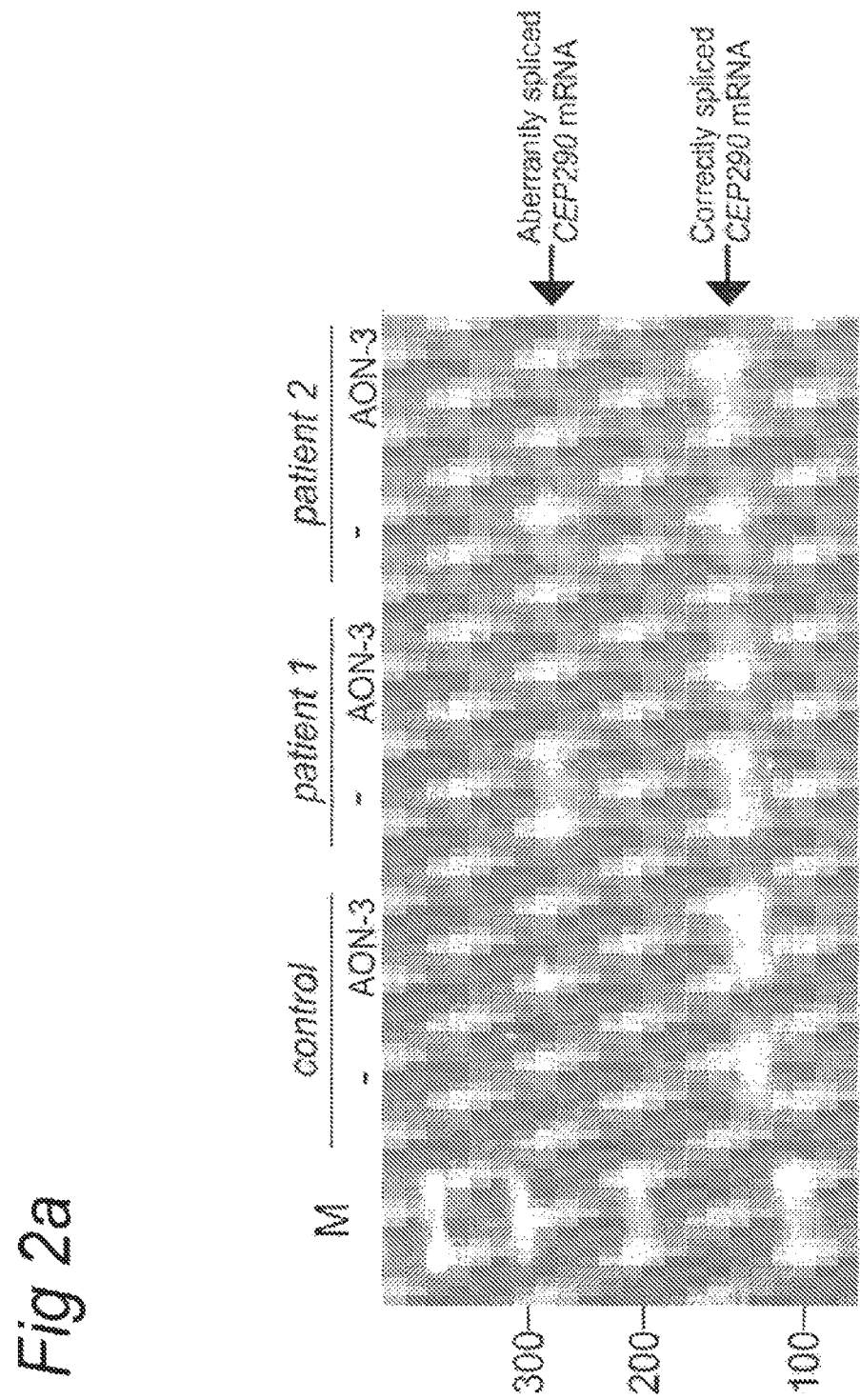

ANTISENSE OLIGONUCLEOTIDES FOR THE TREATMENT OF LEBER CONGENITAL AMAUROSIS

CROSS-REFERENCE TO RELATED APPLICATIONS

The present application is a Continuation Application of U.S. application Ser. No. 15/656,635, filed Jun. 21, 2017, which is a Continuation Application of U.S. application Ser. No. 14/342,776, filed Jun. 16, 2014, which is the U.S. National Phase of International Patent Application No. PCT/NL2012/050275, filed Apr. 25, 2012 and published as WO 2013/036105 AI, which claims priority to Netherlands Patent Application No. 2007351, filed Sep. 5, 2011, and U.S. Provisional Application No. 61/531,137, 10 filed Sep. 6, 2011. The contents of these applications are herein incorporated by reference in their entirety.

SEQUENCE LISTING

The instant application contains a Sequence Listing which has been submitted electronically in ASCII format and is hereby incorporated by reference in its entirety. Said ASCII copy, created on Jul. 17, 2017, is named 069818-9676SequenceListing.txt and is 229 KB.

FIELD OF THE INVENTION

The present invention relates to the fields of medicine and immunology. In particular, it relates to novel antisense oligonucleotides that may be used in the treatment, prevention and/or delay of Leber congenital amaurosis.

BACKGROUND OF THE INVENTION

Leber congenital amaurosis (LCA) is the most severe form of inherited retinal dystrophy, with an onset of disease symptoms in the first years of life (Leber, T., 1869) and an estimated prevalence of approximately 1 in 50,000 worldwide (Koenekoop et al, 2007; Stone, 2007). Genetically, LCA is a heterogeneous disease, with fifteen genes identified to date in which mutations are causative for LCA (den Hollander et al, 2008; Estrada-Cuzcano et al, 2011). The most frequently mutated LCA gene is CEP290, accounting for ~15% of all cases (Stone, 2007; den Hollander, 2008; den Hollander, 2006; Perrault et al, 2007). Severe mutations in CEP290 have been reported to cause a spectrum of systemic diseases that, besides retinal dystrophy, are characterized by brain defects, kidney malformations, polydactyly and/or obesity (Baal et al, 2007; den Hollander et al, 2008; Helou et al., 2007; Valente et al, 2006). There is no clear-cut genotype-phenotype correlation between the combination of CEP290 mutations and the associated phenotypes, but patients with LCA and early-onset retinal dystrophy very often carry hypomorphic alleles (Stone, 2007; den Hollander et al, 2006; Perrault et al, 2007; Coppieters et al, 2010; Liitink et al 2010). The by far most frequently occurring hypomorphic CEP290 mutation, especially European countries and in the US, is a change in intron 26 of CEP290 (c.2991+1655A>G) (Stone, 2007; den Hollander et al, 2006; Perrault et al, 2007; Liitink et al, 2010). This mutation creates a cryptic splice donor site in intron 26 which results in the inclusion of an aberrant exon of 128 bp in the mutant CEP290 mRNA, and inserts a premature stop codon (p.C998X) (see FIG. 1). Besides the mutant CEP290 mRNA, also the wild-type transcript that lacks the aberrant exon is still produced, explaining the hypomorphic nature of this mutation (Estrada-Cuzcano et al, 2011).

LCA, and other retinal dystrophies, for long have been considered incurable diseases. However, the first phase I/II clinical trials using gene augmentation therapy have lead to promising results in a selected group of adult LCA/RP patients with mutations in the RPE65 gene (Bainbridge et al, 2008, Cideciyan et al, 2008; Hauswirth et al, 2008; Maguire et al, 2008). Unilateral subretinal injections of adeno-associated viruses particles carrying constructs encoding the wild-type RPE65 cDNA were shown to be safe and moderately effective in some patients, without causing any adverse effects. In a follow-up study using adults and children, visual improvements were more sustained, especially in the children who all gained ambulatory vision (Maguire et al, 2009). Together, these studies have shown the potential to treat LCA, and thereby enormously boosted the development of therapeutic strategies for other genetic subtypes of retinal dystrophies (den Hollander et al, 2010). However, due to the tremendous variety in gene size, and technical limitations of the vehicles that are used to deliver therapeutic constructs, gene augmentation therapy may not be applicable to all genes. The RPE65 cDNA is for instance only 1.6 kb, whereas the CEP290 cDNA amounts to about 7.4 kb, thereby exceeding the cargo size of many available vectors, including the presently used adeno-associated vectors (AAV). In addition, using gene replacement therapy, it is hard to control the expression levels of the therapeutic gene which for some genes need to be tightly regulated. It is therefore an objective of the present invention to provide a convenient therapeutic strategy for the prevention, treatment or delay of Leber congenital amaurosis as caused by an intronic mutation in CEP290.

DETAILED DESCRIPTION OF THE INVENTION

Surprisingly, it has now been demonstrated that specific antisense oligonucleotides (AONs) are able to block the aberrant splicing of CEP290 that is caused by the intronic LCA mutation.

Accordingly, in a first aspect the present invention provides an exon skipping molecule that binds to and/or is complementary to a polynucleotide with the nucleotide sequence as shown in SEQ ID NO: 6, preferably SEQ ID NO: 7, more preferably SEQ ID NO: 8, or a part thereof.

In all embodiments of the present invention, the terms "modulating splicing" and "exon skipping" are synonymous. In respect of CEP290, "modulating splicing" or "exon skipping" are to be construed as the exclusion of the aberrant 128 nucleotide exon (SEQ ID NO: 4) from the CEP290 mRNA (see FIG. 1). The term exon skipping is herein defined as the induction within a cell of a mature mRNA that does not contain a particular exon that would be present in the mature mRNA without exon skipping. Exon skipping is achieved by providing a cell expressing the pre-mRNA of said mature mRNA with a molecule capable of interfering with sequences such as, for example, the (cryptic) splice donor or (cryptic) splice acceptor sequence required for allowing the enzymatic process of splicing, or with a molecule that is capable of interfering with an exon inclusion signal required for recognition of a stretch of nucleotides as an exon to be included in the mature mRNA; such molecules are herein referred to as exon skipping molecules. The term pre-mRNA refers to a non-processed or partly processed precursor mRNA that is synthesized from a DNA template in the nucleus of a cell by transcription.

The term "antisense oligonucleotide" is understood to refer to a nucleotide sequence which is substantially complementary to a target nucleotide sequence in a pre-mRNA molecule, hrRNA (heterogeneous nuclear RNA) or mRNA molecule. The degree of complementarity (or substantial complementarity) of the antisense sequence is preferably such that a molecule comprising the antisense sequence can form a stable hybrid with the target nucleotide sequence in the RNA molecule under physiological conditions.

The terms "antisense oligonucleotide" and "oligonucleotide" are used interchangeably herein and are understood to refer to an oligonucleotide comprising an antisense sequence.

In an embodiment, an exon skipping molecule as defined herein can be a compound molecule that binds and/or is complementary to the specified sequence, or a protein such as an RNA-binding protein or a non-natural zinc-finger protein that has been modified to be able to bind to the indicated nucleotide sequence on a RNA molecule. Methods for screening compound molecules that bind specific nucleotide sequences are, for example, disclosed in PCT/NL01/00697 and U.S. Pat. No. 6,875,736, which are herein incorporated by reference. Methods for designing RNA-binding Zinc-finger proteins that bind specific nucleotide sequences are disclosed by Friesen and Darby, Nature Structural Biology 5: 543-546 (1998) which is here to incorporated by reference. Binding to one of the specified SEQ ID NO. 6, 7 or 8 sequence, preferably in the context of the aberrant 128 nucleotide CEP290 exon (SEQ ID NO. 4) may be assessed via techniques known to the skilled person. A preferred technique is gel mobility shift assay as described in EP 1 619 249. In a preferred embodiment, an exon skipping molecule is said to bind to one of the specified sequences as soon as a binding of said molecule to a labeled sequence SEQ ID NO.: 6, 7 or 8 is detectable in a gel mobility shift assay.

In all embodiments of the invention, an exon skipping molecule is preferably a nucleic acid molecule, preferably an oligonucleotide. Preferably, an exon skipping molecule according to the invention is a nucleic acid molecule, preferably an oligonucleotide, which is complementary or substantially complementary to a nucleotide sequence as shown in SEQ ID NO: 6, preferably SEQ ID NO: 7, more preferably SEQ ID NO: 8, or a part thereof as later defined herein.

The term "substantially complementary" used in the context of the present invention indicates that some mismatches in the antisense sequence are allowed as long as the functionality, i.e., inducing skipping of the aberrant 128 nucleotide CEP290 exon (SEQ ID NO: 4), is still acceptable. Preferably, the complementarity is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

The present invention provides a method for designing an exon skipping molecule, preferably an oligonucleotide able to induce skipping of the aberrant 128 nucleotide CEP290 exon (SEQ ID NO: 4). First, said oligonucleotide is selected to bind to one of SEQ ID NO: 6, 7 or 8 or a part thereof as defined later herein. Subsequently, in a preferred method at least one of the following aspects has to be taken into account for designing, improving said exon skipping molecule any further:

The exon skipping molecule preferably does not contain a CpG or a stretch of CpG, The exon skipping molecule has acceptable RNA binding kinetics and/or thermodynamic properties.

The presence of a CpG or a stretch of CpG in an oligonucleotide is usually associated with an increased immunogenicity of said oligonucleotide (Dorn and Kippenberger, 2008). This increased immunogenicity is undesired since it may induce damage of the tissue to be treated i.e. the eye. Immunogenicity may be assessed in an animal mode by assessing the presence of CD4+ and/or CD8+ cells and/or inflammatory mononucleocyte infiltration. Immunogenicity may also be assessed in blood of an animal or of a human being treated with an oligonucleotide of the invention by detecting the presence of a neutralizing antibody and/or an antibody recognizing said oligonucleotide using a standard immunoassay known to the skilled person.

An increase in immunogenicity may be assessed by detecting the presence of an increasing amount of a neutralizing antibody or an antibody recognizing said oligonucleotide using a standard immunoassay.

The invention allows designing an oligonucleotide with acceptable RNA binding kinetics a and/or thermodynamic properties. The RNA binding kinetics and/or thermodynamic properties are at least in part determined by the melting temperature of an oligonucleotide (Tm; calculated with the oligonucleotide properties calculator (www.unc.edu/~cail/biotool/oligo/index.html) for single stranded RNA using the basic Tm and the nearest neighbor model), and/or the free energy of the AON-target exon complex (using RNA structure version 4.5). If a Tm is too high, the oligonucleotide is expected to be less specific. An acceptable Tm and free energy depend on the sequence of the oligonucleotide. Therefore, it is difficult to give preferred ranges for each of these parameters. An acceptable Tm may be ranged between 35 and 70° C. and an acceptable free energy may be ranged between 15 and 45 kcal/mol.

The skilled person may therefore first choose an oligonucleotide as a potential therapeutic compound as binding and/or being complementary to SEQ ID NO: 6, 7, or 8 or a part thereof as defined later herein. The skilled person may check that said oligonucleotide is able to bind to said sequences as earlier defined herein. Optionally in a second step, he may use the invention to further optimize said oligonucleotide by checking for the absence of CpG and/or by optimizing its Tm and/or free energy of the AON-target complex. He may try to design an oligonucleotide wherein preferably no CpG and/or wherein a more acceptable Tm and/or free energy are obtained by choosing a distinct sequence of CEP290 (including SEQ ID NO: 6, 7 or 8) to which the oligonucleotide is complementary. Alternatively, if an oligonucleotide complementary to a given stretch within SEQ ID NO: 6, 7 or 8, comprises a CpG, and/or does not have an acceptable Tm and/or free energy, the skilled person may improve any of these parameters by decreasing the length of the oligonucleotide, and/or by choosing a distinct stretch within any of SEQ ID NO: 6, 7 or 8 to which the oligonucleotide is complementary and/or by altering the chemistry of the oligonucleotide.

At any step of the method, an oligonucleotide of the invention is preferably an oligonucleotide, which is still able to exhibit an acceptable level of functional activity. A functional activity of said oligonucleotide is preferably to induce the skipping of the aberrant 128 nucleotide CEP290 exon (SEQ ID NO: 4) to a certain extent, to provide an individual with a functional CEP290 protein and/or mRNA and/or at least in part decreasing the production of an aberrant CEP290 protein and/or mRNA. In a preferred embodiment, an oligonucleotide is said to induce skipping of the aberrant 128 nucleotide CEP290 exon (SEQ ID NO: 4), when the aberrant 128 nucleotide (CEP290 exon (SEQ ID NO: 4) skipping percentage as measured by real-time quantitative RT-PCR analysis (is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%).

Preferably, a nucleic acid molecule according to the invention, preferably an oligonucleotide, which comprises a sequence that is complementary or substantially complementary to a nucleotide sequence as shown in SEQ ID NO: 6, preferably SEQ ID NO: 7, more preferably SEQ ID NO: 8, or part thereof of CEP290 is such that the (substantially) complementary part is at least 50% of the length of the oligonucleotide according to the invention, more preferably at least 60%, even more preferably at least 70%, even more preferably at least 80%, even more preferably at least 90%, or even more preferably at least 95%, or even more preferably 98%, or even more preferably at least 99%, or even more preferably 100%. Preferably, an oligonucleotide according to the invention comprises or consists of a sequence that is complementary to part of SEQ ID NO: 6, 7 or 8. As an example, an oligonucleotide may comprise a sequence that is complementary to part of SEQ ID NO: 6, 7 or 8 and additional flanking sequences. In a more preferred embodiment, the length of said complementary part of said oligonucleotide is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides. Additional flanking sequences may be used to modify the binding of a protein to the oligonucleotide, or to modify a thermodynamic property of the oligonucleotide more preferably to modify target RNA binding affinity.

It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may, to some extent, be allowed, if under the circumstances in the cell, the stretch of nucleotides is sufficiently capable of hybridizing to the complementary part. In this context, "sufficiently" preferably means that using a gel mobility shift assay as described in example 1 of EP 1619249, binding of an oligonucleotide is detectable. Optionally, said oligonucleotide may further be tested by transfection into retina cells of patients. Skipping of a targeted exon may be assessed by RT-PCR (as described in EP1619249). The complementary regions are preferably designed such that, when combined, they are specific for the exon in the pre-mRNA. Such specificity may be created with various lengths of complementary regions as this depends on the actual sequences in other (pre-)mRNA molecules in the system. The risk that the oligonucleotide also will be able to hybridize to one or more other pre-mRNA molecules decreases with increasing size of the oligonucleotide. It is clear that oligonucleotides comprising mismatches in the region of complementarity but that retain the capacity to hybridize and/or bind to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought, that higher hybridization strengths, (i.e. increasing number of interactions with the opposing strand) are favorable in increasing the efficiency of the process of interfering with the splicing machinery of the system. Preferably, the complementarity is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

An exon skipping molecule of the invention is preferably an isolated molecule.

An exon skipping molecule of the invention is preferably a nucleic acid molecule or nucleotide-based molecule, preferably an (antisense) oligonucleotide, which is complementary to a sequence selected from SEQ ID NO: 6, 7 and 8.

A preferred exon skipping molecule, according to the invention is a nucleic acid molecule comprising an antisense oligonucleotide which antisense oligonucelotide has a length from about 8 to about 143 nucleotides, more preferred from about 8 to 60, more preferred 10 to about 40 nucleotides, more preferred from about 12 to about 30 nucleotides, more preferred from about 14 to about 28 nucleotides, nucleotides, most preferred about 20 nucleotides, such as 15 nucleotides, 16 nucleotides, 17 nucleotides, 18 nucleotides, 19 nucleotides, 20 nucleotides, 21 nucleotides, 22 nucleotides, 23 nucleotides, 24 nucleotides or 25 nucleotides.

A preferred exon skipping molecule of the invention is an antisense oligonucelotide comprising or consisting of from 8 to 143 nucleotides, more preferred from 10 to 40 nucleotides, more preferred from 12 to 30 nucleotides, more preferred from 14 to 20 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In certain embodiments, the invention provides an exon skipping molecule composing or preferably consisting of an antisense oligonucleotide selected from the group consisting of SEQ ID NO: 10, SEQ ID NO: 11, and SEQ ID NO: 12.

In a more preferred embodiment, the invention provides an exon skipping molecule comprising or preferably consisting of the antisense oligonucleotide SEQ ID NO: 10. It was found that this molecule is very efficient in modulating splicing of the aberrant 128 nucleotide CEP290 exon. This preferred exon skipping molecule of the invention comprising SEQ ID NO: 10 preferably comprises from 8 to 143 nucleotides, more preferred from 10 to 40 nucleotides, more preferred from 10 to 30 nucleotides, more preferred from 12 to 20 nucleotides, more preferably from 14 to 18 or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In another more preferred embodiment, the invention provides an exon skipping molecule comprising or preferably consisting of the antisense oligonucleotide SEQ ID NO: 11. It was found that this molecule is very efficient in modulating splicing of the aberrant 128 nucleotide CEP290 exon. This preferred exon skipping molecule of the invention comprising SEQ ID NO: 11 preferably comprises from 8 to 143 nucleotides, more preferred from 10 to 40 nucleotides, more preferred from 10 to 30 nucleotides, more preferred from 12 to 20 nucleotides, more preferably from 14 to 18, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 50, 60, 65, 70, 75, 80, 85, 90, 95, 100, 110, 115, 120, 125, 130, 135, 140, 141, 142 or 143 nucleotides.

In another more preferred embodiment, the invention provides an exon skipping molecule comprising or preferably consisting of the antisense oligonucleotide SEQ ID NO: 12. It was found that this molecule is very efficient in modulating splicing of the aberrant 128 nucleotide CEP290 exon. This preferred exon skipping molecule of the invention comprising SEQ ID NO: 12 preferably comprises from 8 to 143 nucleotides, more preferred from 10 to 40 nucleotides, more preferred from 10 to 30 nucleotides, more preferred from 12 to 20 nucleotides, more preferred from 14 to 18, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

An exon skipping molecule according to the invention may contain one of more RNA residues, or one or more DNA residues, and/or one or more nucleotide analogues or equivalents, as will be further detailed herein below.

It is preferred that an exon skipping molecule of the invention comprises one or more residues that are modified to increase nuclease resistance, and/or to increase the affinity of the antisense oligonucleotide for the target sequence. Therefore, in a preferred embodiment, the antisense nucleotide sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery, however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium.

It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionalkylphosphonate, thionalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, or aralkyl; that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; -dimethylaminooxyethoxy; and -dimethylaminoethoxyethoxy. The sugar moiety can be a pyranose or derivative thereof, or a deoxypyranose or derivative thereof, preferably ribose or derivative thereof, or deoxyribose or derivative of. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-O,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

A preferred exon skipping molecule according to the invention comprises a 2'-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives.

An effective antisense oligonucleotide according to the invention comprises a 2'-O-methyl ribose with a phosphorothioate backbone.

It will also be understood by a skilled person that different antisense oligonucleotides can be combined for efficiently skipping of the aberrant 128 nucleotide exon CEP290. In a preferred embodiment, a combination of at least two antisense oligonucleotides are used in a method of the invention, such as two different antisense oligonucleotides, three different antisense oligonucleotides, four different antisense oligonucleotides, or five different antisense oligonucleotides.

An antisense oligonucleotide can be linked to a moiety that enhances uptake of the antisense oligonucleotide in cells, preferably retina cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

An exon skipping molecule according to the invention may be indirectly administrated using suitable means shown in the art. When the exon skipping molecule is an oligonucleotide, it may for example be provided to an individual or a cell, tissue or organs of said individual in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of an exon skipping molecule as identified herein. Accordingly, the present invention provides a viral vector expressing an exon skipping molecule according to the invention when placed under conditions conducive to expression of the exon skipping molecule. A cell can be provided with an exon skipping molecule capable of interfering with essential sequences that result in highly efficient skipping of the aberrant 128 nucleotide CEP290 exon by plasmid-derived antisense oligonucleotide expression or viral expression provided by adenovirus- or adeno-associated virus-based vectors. Expression may be driven by a polymerase III promoter, such as a U1, a U6, or a U7 RNA promoter. A preferred delivery vehicle is a viral sector such as an adeno-associated virus vector (AAV), or a retroviral vector such as a lentivirus vector and the like. Also, plasmids, artificial chromosomes, plasmids usable for targeted homologous recombination and integration in the human genome of cells may be suitably applied for delivery of an oligonucleotide as defined herein. Preferred for the current invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts. Preferably, in the form of a fusion transcript with an U1 or U7 transcript. Such fusions may be generated as described (Gorman L et al, 1998 or Suter D et al, 1999).

The exon slopping molecule according to the invention, preferably an antisense oligonucleotide, may be delivered as such. However, the exon skipping molecule may also be encoded by the viral vector. Typically, this is in the form of an RNA transcript that comprises the sequence of an oligonucleotide according to the invention in a part of the transcript.

One preferred antisense oligonucleotide expression system is an adenovirus associated virus (AAV)-based vector. Single chain and double chain AAV-based vectors have been developed that can be used for prolonged expression of small antisense nucleotide sequences for highly efficient skipping of the aberrant 128 nucleotide CEP290 exon.

A preferred AAV-based vector for instance comprises an expression cassette that is driven by a polymerase III-promoter (Pol III). A preferred Pol III promoter is, for example, a U1, a U6, or a U7 RNA promoter.

The invention therefore also provides a viral-based vector, comprising a Pol III-promoter driven expression cassette for expression of an antisense oligonucleotide of the invention for inducing skipping of aberrant 128 nucleotide CEP290 exon.

Improvements in means for providing an individual or a cell, tissue, organ of said individual with an exon skipping molecule according to the invention, are anticipated considering the progress that has already thus far been achieved. Such future improvements may of course be incorporated to achieve the mentioned effect on restructuring of mRNA using a method of the invention. An exon skipping molecule according to the invention can be delivered as is to an individual, a cell, tissue or organ of said individual. When administering an exon skipping molecule according to the invention, it is preferred that the molecule is dissolved in a solution that is compatible with the delivery method. Retina cells can be provided with a plasmid for antisense oligonucleotide expression by providing the plasmid in an aqueous solution. Alternatively, a plasmid can be provided by transfection using known transfection agentia. For intravenous, subcutaneous, intramuscular, intrathecal and/or intraventricular administration it is preferred that the solution is a physiological salt solution. Particularly preferred in the invention is the use of an excipient or transfection agentia that will aid in delivery of each of the constituents as defined herein to a cell and/or into a cell, preferably a retina cell. Preferred are excipients or transfection agentia capable of forming complexes, nanoparticles, micelles, vesicles and/or liposomes that deliver each constituent as defined herein, completed or trapped in a vesicle or liposome through a cell membrane. Many of these excipients are known in the art. Suitable excipients or transfection agentia comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self assembly into particles that can deliver each constituent as defined herein to a cell, preferably a retina cell. Such excipients have been shown to efficiently deliver an oligonucleotide such as antisense nucleic acids to a wide variety of cultured cells, including retina cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide, across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an exon skipping molecule for use in the current invention to deliver it for the prevention, treatment or delay of a CEP290 related disease or condition. "Prevention, treatment or delay of a CEP290 related disease or condition" is herein preferably defined as preventing, halting, ceasing the progression of, or reversing partial or complete visual impairment or blindness that is caused by a genetic defect in the CEP290 gene.

In addition, an exon skipping molecule according to the invention could be covalently or non-covalently linked to a targeting ligand specifically designed to facilitate the uptake into the cell, cytoplasm and/or its nucleus. Such ligand could compose (i) a compound (including but not limited to peptide(-like) structures) recognising cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an exon skipping molecule according to the invention is formulated in a composition or a medicament or a composition, which is provided with at least an excipient and/or a targeting ligand for delivery and/or a delivery device thereof to a cell and/or enhancing its intracellular delivery.

It is to be understood that if a composition comprises an additional constituent such as an adjunct compound as later defined herein, each constituent of the composition may not be formulated in one single combination or composition or preparation. Depending on their identity, the skilled person will know which type of formulation is the most appropriate for each constituent as defined herein. In a preferred embodiment, the invention provides a composition or a preparation which is in the form of a kit of parts comprising an exon skipping molecule according to the invention and a further adjunct compound as later defined herein.

If required, an exon skipping molecule according to the invention or a vector, preferably a viral vector, expressing an exon skipping molecule according to the invention can be incorporated into a pharmaceutically active mixture by adding a pharmaceutically acceptable carrier.

Accordingly, the invention also provides a composition, preferably a pharmaceutical composition, comprising an exon skipping molecule according to the invention, or a viral vector according to the invention and a pharmaceutically acceptable excipient. Such composition may comprise a single exon skipping molecule according to the invention, but may also comprise multiple, distinct exon skipping molecules according to the invention. Such a pharmaceutical composition may comprise any pharmaceutically acceptable excipient, including a carrier, filler, preservative, adjuvant, solubilizer and/or diluent. Such pharmaceutically acceptable carrier, filler, preservative, adjuvant, solubilizer and/or diluent may for instance be found in Remington, 2000. Each feature of said composition has earlier been defined herein.

If multiple distinct exon skipping molecules according to the invention are used, concentration or dose defined herein may refer to the total concentration or dose of all oligonucleotides used or the concentration or dose of each exon skipping molecule used or added. Therefore in one embodiment, there is provided a composition wherein each or the total amount of exon skipping molecules according to the invention used is dosed in an amount ranged from 0.1 and 20 mg/kg, preferably 0.5 and 20 mg/kg.

A preferred exon skipping molecule according to the invention, is for the treatment of CEP290 related disease or condition of an individual. In all embodiments of the present invention, the term "treatment" is understood to include the prevention and/or delay of the CEP290 related disease or condition. An individual, which may be treated using an exon skipping molecule according to the invention may already have been diagnosed as having a CEP290 related disease or condition. Alternatively, an individual which may be treated using an exon skipping molecule according to the invention may not have yet been diagnosed as having a CEP290 related disease or condition but may be an individual having an increased risk of developing a CEP290 related disease or condition in the future given his or her genetic background. A preferred individual is a human being. In a preferred embodiment the CEP290 related disease or condition is Leber congenital amaurosis.

Accordingly, the present invention further provides an exon skipping molecule according to the invention, or a viral vector according to the invention, or a composition according to the invention for use as a medicament, for treating a CEP290 related disease or condition requiring modulating splicing of CEP290 and for use as a medicament for the prevention, treatment or delay of a CEP290 related disease or condition. A preferred CEP290 related disease or condition is Leber congential amaurosis. Each feature of said use has earlier been defined herein.

The invention further provides the use of an exon skipping molecule according to the invention, or of a viral vector according to the invention, or a composition according to the invention for the treatment of a CEP290 related disease or condition requiring modulating splicing of CEP290. In a preferred embodiment the CEP290 related disease or condition is Leber congenital amaurosis.

The present invention further provides the use of an exon skipping molecule according to the invention, or of a viral vector according to the invention, or a composition according to the invention for the preparation of a medicament, for the preparation of a medicament for treating a CEP290 related disease or condition requiring modulating splicing of CEP290 and for the preparation of a medicament for the prevention, treatment or delay of a CEP290 related disease or condition. A preferred CEP290 related disease or condition is Leber congenital amaurosis. Therefore in a further aspect, there is provided the use of an exon skipping molecule, viral vector or composition as defined herein for the preparation of medicament, for the preparation of a medicament for treating a condition requiring modulating splicing of CEP290 and for the preparation of a medicament for the prevention treatment or delay of a CEP290 related disease or condition. A preferred CEP290 related disease or condition is Leber congenital amaurosis. Each feature of said use has earlier been defined herein.

A treatment in a use or in a method according to the invention is at least one week, at least one month, at least several months, at least one year, at least 2, 3, 4, 5, 6 years or more. Each exon skipping molecule or exon skipping oligonucleotide or equivalent thereof as defined herein for use according to the invention may be suitable for direct administration to a cell, tissue and/or an organ in vivo of individuals already affected or at risk of developing CEP290 related disease or condition, and may be administered directly in vivo, ex vivo or in vitro. The frequency of administration of an oligonucleotide, composition, compound or adjunct compound of the invention may depend on several parameters such as the age of the patient, the mutation of the patient, the number of exon skipping molecules (i.e. dose), the formulation of said molecule. The frequency may be ranged between at least once in two weeks, or three weeks or four weeks or five weeks or a longer time period.

Dose ranges of an exon skipping molecule, preferably an oligonucleotide according to the invention are preferably designed on the basis of rising dose studies in clinical trials (in vivo use) for which rigorous protocol requirements exist. An exon skipping molecule or an oligonucleotide as defined herein may be used at a dose which is ranged from 0.1 and 20 mg/kg, preferably from 0.5 and 20 mg/kg.

In a preferred embodiment, a concentration of an oligonucleotide as defined herein, which is ranged from 0.1 nM and 1 µM is used. Preferably, this range is for in vitro use in a cellular model such as retina cells or retinal tissue. More preferably, the concentration used is ranged from 1 to 400 nM, even more preferably from 10 to 200 nM, even more preferably from 50 to 100 nm. If several oligonucleotides are used, this concentration or dose may refer to the total concentration or dose of oligonucleotides or the concentration or dose of each oligonucleotide added.

In a preferred embodiment, a viral vector, preferably an AAV vector as described earlier herein, as delivery vehicle for a molecule according to the invention, is administered in a dose ranging from $1 \times 10^9$-$1 \times 10^{17}$ virusparticles per injection, more preferably from $1 \times 10^{10}$-$1 \times 10^{12}$ virusparticles per injection.

The ranges of concentration or dose of oligonucleotide(s) as given above are preferred concentrations or doses for in vitro or ex vivo uses. The skilled person will understand that depending on the oligonucleotide(s) used, the target cell to be treated, the gene target and its expression levels, the medium used and the transfection and incubation conditions, the concentration or dose of oligonucleotide(s) used may further vary and may need to be optimized any further.

An exon skipping molecule according to the invention, or a viral vector according to the invention, or a composition according to the invention for use according to the invention may be suitable for administration to a cell, tissue and/or an organ in vivo of individuals already affected or at risk of developing a CEP290 related disease or condition, and may be administered in vivo, ex vivo or in vitro. Said exon skipping molecule according to the invention, or a viral vector according to the invention, or a composition according to the invention may be directly or indirectly administrated to a cell, tissue and/or an organ in vivo of an individual already affected by or at risk of developing a CEP290 related disease or condition, and may be administered directly or indirectly in vivo, ex vivo or in vitro. As Leber congenital amaurosis has a pronounced phenotype in retina cells, it is preferred that said cells are retina cells, it is further preferred that said tissue is the retina and/or it is further preferred that said organ comprises or consists of the eye.

The invention further provides a method for modulating splicing of CEP290 in a cell comprising contacting the cell, preferably a retina cell, with an exon skipping molecule according to the invention, or a viral vector according to the invention, or a composition according to the invention. The features of this aspect are preferably those defined earlier herein. Contacting the cell with an exon skipping molecule according to the invention, or a viral vector according to the invention, or a composition according to the invention may be performed by any method known by the person skilled in the art. Use of the methods for delivery of exon skipping molecules, viral vectors and compositions described herein is included. Contacting may be directly or indirectly and may be in vivo, ex vivo or in vitro.

The invention further provides a method for the treatment of a CEP290 related disease or condition requiring modulating splicing of CEP290 of an individual in need thereof, said method comprising contacting a cell, preferably a retina cell, of said individual with an exon skipping molecule according to the invention, or a viral vector according to the invention, or a composition according to the invention. The features of this aspect are preferably those defined earlier herein. Contacting the cell, preferably a retina cell with an exon skipping molecule according to the invention, or a viral vector according to the invention, or a composition according to the invention may be performed by any method known by the person skilled in the art. Use of the methods for delivery of molecules, viral vectors and compositions described herein is included. Contacting may be directly or indirectly and may be in vivo, ex vivo or in vitro. A preferred CEP290 related disease or condition is Leber congenital amaurosis.

Unless otherwise indicated each embodiment as described herein may be combined with another embodiment as described herein.

As can be observed in the experimental section herein, at the RNA level, addition of various AONs targeting the aberrant CEP290 exon indeed resulted in a conversion of aberrantly spliced CEP290 mRNA to correctly spliced CEP290 mRNA. This conversion will coincide with an increased synthesis of the wild-type CEP290 protein.

In fibroblasts (that can be derived from skin cells), CEP290 is abundantly expressed. Therefore, it is to be expected that addition of AONs to cultured fibroblasts from LCA patients will result in an increased amount of wild-type CEP290 protein that is detectable on Western blot, and as such will demonstrate that AON-based therapy will not only redirect normal splicing of CEP290 mRNA but will also result in restoring CEP290 protein function. This experiment is presently ongoing.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 0.1% of the value.

The sequence information as provided herein should not be so narrowly construed as to require inclusion of erroneously identified bases. The skilled person is capable of identifying such erroneously identified bases and knows how to correct for such errors. In case of sequence errors, the sequence of the polypeptide obtainable by expression of the gene present in SEQ ID NO: 1 containing the nucleic acid sequence coding for the polypeptide should prevail.

All patent and literature references cited in the present specification are hereby incorporated by reference in their entirety.

A) Normal CEP290 mRNA splicing of exons 26 and 27, resulting in wild-type CEP290 protein (figure discloses SEQ ID NOS 17-18, respectively, in order of appearance).

B) The most frequent LCA-causing mutation is an A-to-G transition (underlined and indicated with an asterisk) in intron 26 of CEP290. This mutation creates a splice donor site, which results in the inclusion of an aberrant exon to ~50% of the CEP290 mRNA and subsequent premature termination of the CEP290 protein (figure discloses SEQ ID NOS 19-20, respectively, in order of appearance).

C) Upon binding of sequence-specific AONs, factors involved in splicing will not recognize the aberrant splice donor site in intron 26, resulting in redirection of normal CEP290 splicing and synthesis of a correct CEP290 protein (figure discloses SEQ ID NOS 19, 21, and 20, respectively, in order of appearance).

Figure 2B:
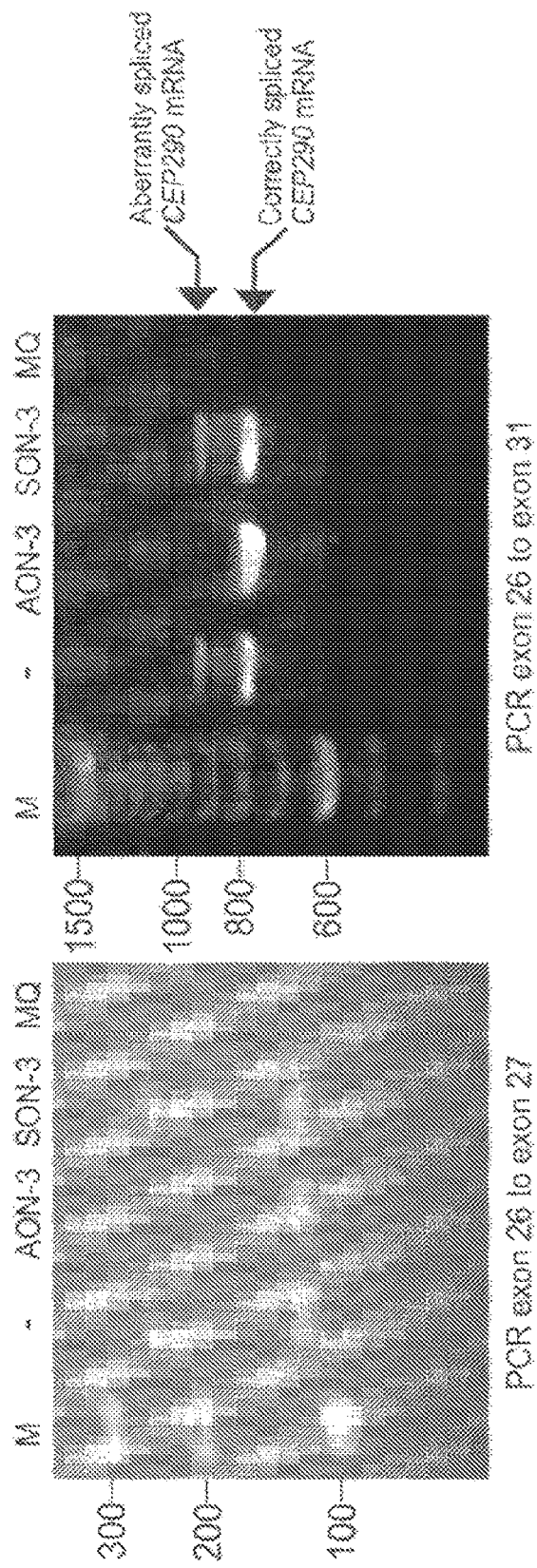
Figure 2C:
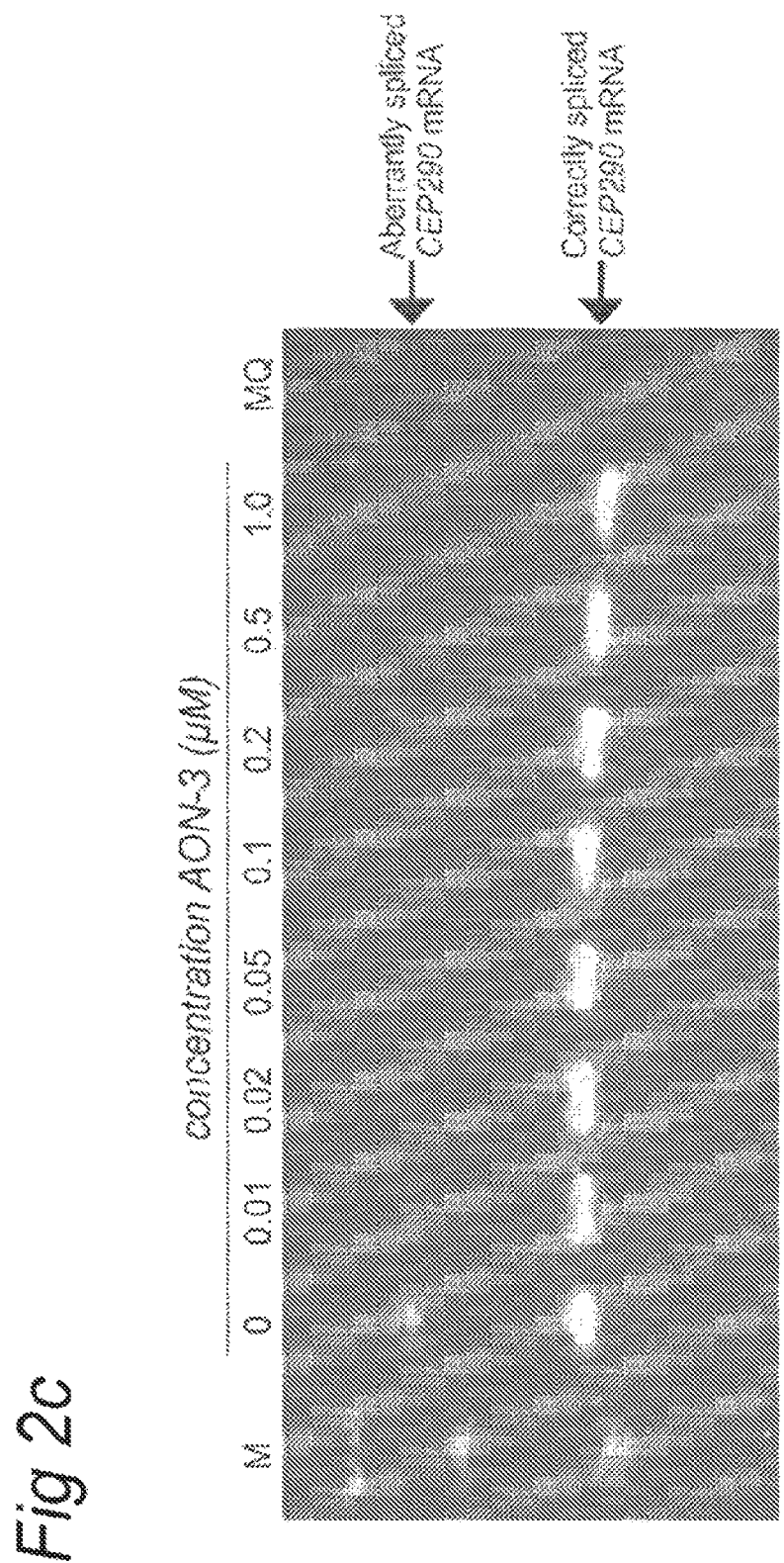

FIGS. 2a, 2b and 2c AON-based rescue of aberrant CEP290 splicing

A) RT-PCR analysis of CEP290 mRNA isolated from lymphoblastoid cells of one control individuals and two individuals affected with LCA, that were cultured in the absence or presence of a selected AON (AON-3) direct against the aberrant CEP290 exonin a final concentration of 1.0 µM. The upper band represents the aberrant CEP290 splice product, whereas the lower band represents the wild-type CEP290 splice product. M: 100-bp marker. MQ: negative water control.

B) Specificity of AON-based rescue. Similar to A), cells were transfected with AON-3, or a sense oligonucleotide directed to the same target site (SON-3). Left panel: RT-PCR reaction using primers located in exon 26 and exon 27. Right panel. RT-PCR reaction using primers located in exon 26 and exon 31.

C) Dose-dependent rescue of CEP290 mRNA splicing. Similar to A), cells were transfected with different concentrations of the selected AON, ranging from 0.01 to 1.0 µM.

Figure 3A:
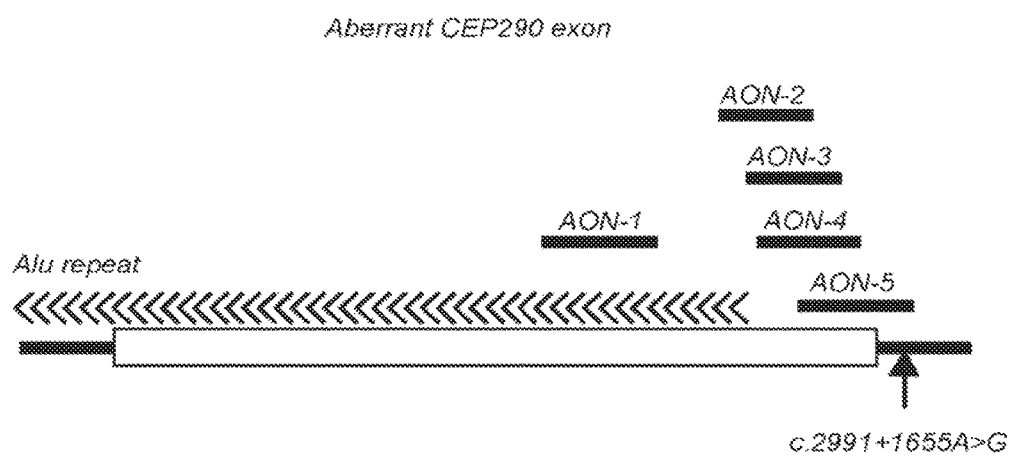
Figure 3B:
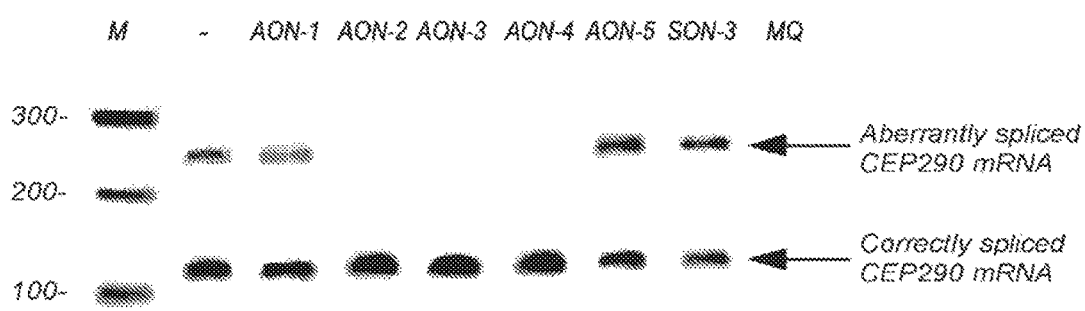

FIGS. 3a and 3b Sequence specificity in AON-based rescue of aberrant CEP290 splicing A) Overview of the aberrant CEP290 exon, and the relative positions of the AONs that were selected. The 5'-end of the aberrant exon is part of an Alu repeat.

B) RT-PCR analysis of CEP290 mRNA isolated from lymphoblastoid cells of an LCA patient that were cultured in the absence or presence of different AONs direct against the aberrant CEP290 exon (AON-1 to -5), or one sense oligonucleotide (SON-3). The AONs and SON were transfected in a final concentration of 0.1 µM. The upper band represents the aberrant CEP290 splice product, whereas the lower band represents the wild-type CEP290 splice product. M: 100-bp marker.

All sequences herein are depicted from 5'→3'

TABLE 1

Sequences as set forth in the Sequence Listing

| SEQ ID NO: | SEQ type | Description |
|---|---|---|
| 1 | Genomic DNA | CEP290 |
| 2 | cDNA | CEP290 |
| 3 | PRT | CEP290 protein |
| 4 | DNA | 128 nucleotide aberrant CEP290 exon |
| 5 | PRT | CEP290 aberrant protein |
| 6 | Polynucleotide | 143 nucleotide motif |
| 7 | Polynucleotide | 42 nucleotide motif |
| 8 | Polynucleotide | 24 nucleotide motif |
| 9 | AON-1 | taatcccagcactttaggag |
| 10 | AON-2 | gggccaggtgcggtgg |
| 11 | AON-3 | aactggggccaggtgcg |
| 12 | AON-4 | tacaactggggccaggtg |

TABLE 1-continued

Sequences as set forth in the Sequence Listing

| SEQ ID NO: | SEQ type | Description |
|---|---|---|
| 13 | AON-5 | actcacaattacaactgggg |
| 14 | SON-3 | cgcacctggcccagtt |
| 15 | PCR primer | tgctaagtacagggacatcttgc |
| 16 | PCR primer | agactccacttgttcttttaaggag |

The present invention is further described by the following examples which should not be construed as limiting the scope of the invention.

Unless stated otherwise, the practice of the invention will employ standard conventional methods of molecular biology, virology, microbiology or biochemistry. Such techniques are described in Sambrook et al. (1989) Molecular Cloning, A Laboratory Manual (2$^{nd}$ edition). Cold Spring Harbor Laboratory, Cold Spring Harbor Laboratory Press; in Sambrook and Russell (2001) *Molecular Cloning: A Laboratory Manual*, Third Edition, Cold Spring Harbor Laboratory Press, NY; in Volumes 1 and 2 of Ausubel et al. (1994) *Current Protocols in Molecular Biology, Current Protocols*, USA; and in Volumes I and II of Brown (1998) *Molecular Biology LabFax*, Second Edition, Academic Press (UK); *Oligonucleotide Synthesis* (N. Gait editor); *Nucleic Acid Hybridization* (Hames and Higgins, eds.).

EXAMPLES

Materials and Methods

Design Antisense Oligonucleotides

The 128-bp sequence of the aberrant CEP290 exon that is included into the mutant CEP290 mRNA was analyzed for the presence of exonic splice enhancer motifs using the ESE finder 3.0 program (http://rulai.cshl.edu/cgi-bin/tools/ESE3/esefinder.cgi?process=home). RNA antisense oligonucleotides were purchased from Eurogentec, and designed with a $T_m$ of 58° C., and modified with a 2'-O-methyl group at the sugar chain and a phosphothioratc backbone, and dissolved in phosphate buffered saline.

Cell Culture

Human B-lymphoblasts cells of LCA patients homozygously carrying the intronic mutation in CEP290 were immortalized by transformation with the Eppstein-Barr virus, as described previously (Wall F E, 1995). Cells were cultured in RPMI1640 medium (Gibco) containing 10% (v/v) fetal calf serum (Sigma), 1% 10 U/µl penicillin and 10 µg/µl streptomycin (Gibco), and 1% GlutaMAX (Gibco), at a density of 0.5×10$^6$ cells/ml. Cells were passaged twice a week.

Transfection of AONs

A day before transfection, 1.0×10$^6$ cells were seeded in each well of a 6-wells plate, in a total volume of 2 ml complete medium. Transfection mixtures were prepared by combining 2.5 µl AON in a desired concentration, or distilled water, 5 µl transfection reagent (ExGen in vitro 500, Fermentas) and 92.5 µl 150 mM NaCl, and incubated at room temperature for 10 minutes, before addition to the cells. Six hours after transfection, 8 ml of low-serum medium (complete medium with only 1% fetal calf serum) was added. Forty-eight hours after transfection, cells were collected and washed with 1×PBS, before directly proceeding to RNA isolation.

RNA Isolation and RT-PCR

Total RNA was isolated from transfected lymphoblastoid cells using the Nucleospin RNA II isolation kit (Machery Nagel), according to manufacturer's protocol. Subsequently, 1 µg of total RNA was used for cDNA synthesis using the tScript cDNA synthesis kit (Bio-Rad). Five percent of the cDNA was used for each PCR reaction. Part of the CEP290 cDNA was amplified under standard PCR conditions supplemented with 5% Q-solution (Qiagen), and using forward primer tgctaagtacagggacatcttgc (SEQ ID NO:15) and reverse primer agactccacttgttctmaaggag (SEQ ID NO: 16) that are located in exon 26 and exon 27 of the human CEP290 gene, respectively. PCR products were resolved on a 1.5% agarose gel. Bands presumably representing correctly and aberrantly spliced CEP290 were excised from the gel, purified using Nucleospin Extract II isolation kit and sequenced from both strands with the ABI PRISM Big Dye Terminator Cycle Sequencing V2.0 Ready Reaction kit and the ABI PRISM 3730 DNA analyzer (Applied Biosystems).

Introduction

Here, we describe the use of AONs to redirect normal splicing of CEP290 in patient-derived lymphoblast cells, and show a sequence-specific and dose-dependent decrease in levels of aberrantly spliced CEP290, thereby revealing the potential of AON-based therapy to treat CEP290-associated LCA.

Results

Figure 1:
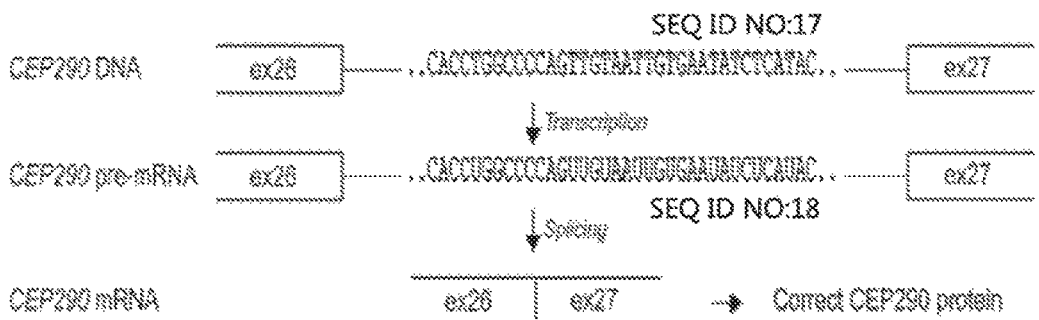
FIG. 1 CEP290 splicing and AON function
Figure 1:
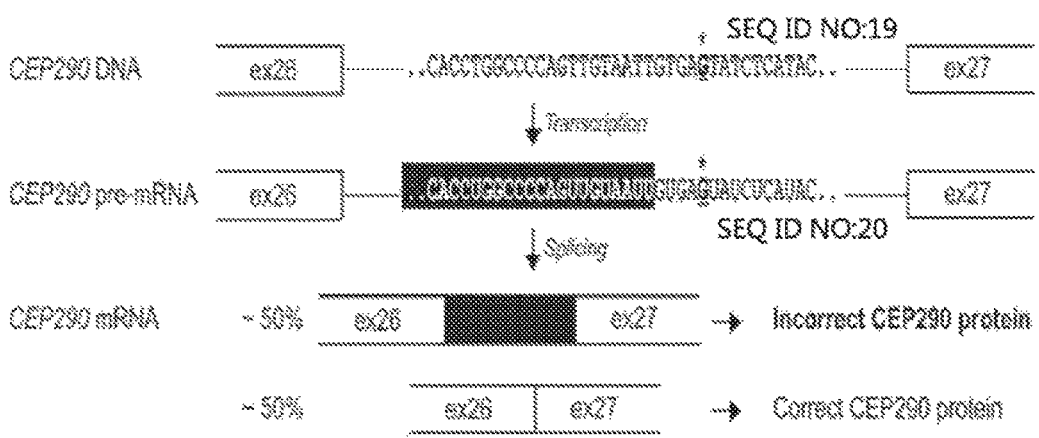
Figure 1:
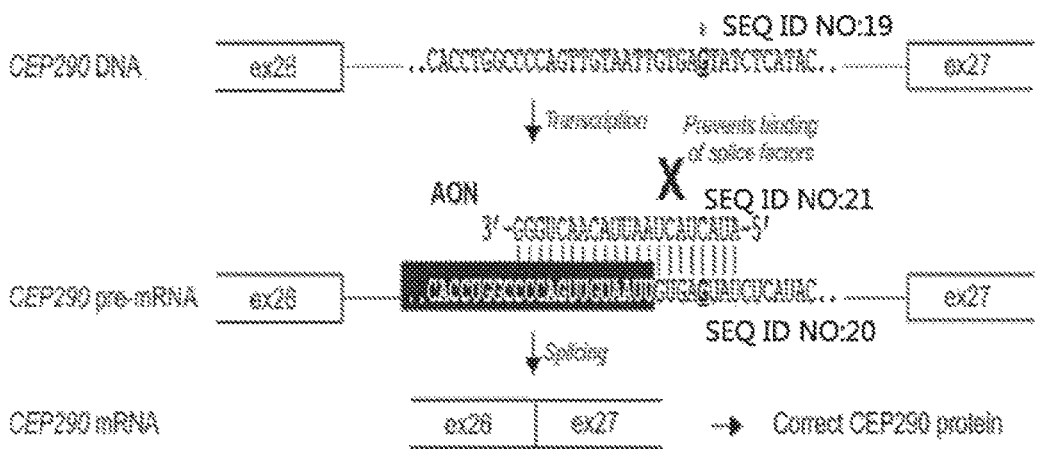

The intronic CEP290 mutation (c.2991+1655A>G) creates a cryptic splice donor site that results in the inclusion of an aberrant exon into the CEP290 mRNA (FIG. 1). Addition of AONs directed against the aberrant exon would prevent the insertion of this exon by prevailing the binding of factors that are essential for splicing such as the U1- and U2snRNP complexes, and serine-arginine rich proteins, thereby restoring normal CEP290 splicing and protein synthesis (FIG. 1). AONs can target splice sites as well as exonic sequences, although in the particular case of the Duchenne muscular dystrophy DMD gene, AONs targeting exonic regions tend to outperform those that target the splice sites (Aartsma-Rus et al, 2010). In addition, previous studies have suggested a positive correlation between the capability of AONs to induce exon skipping and the presence of predicted SC35 splice factor binding sites in the target sequence (Aartsma-Rus et al, 2008). To design an AON with high exon-skipping potential, the aberrant CEP290 exon (128 nucleotides exonic sequence plus 15 nucleotides of intronic sequence on each side) was scrutinized for exonic splice enhancer binding motifs, using the ESE finder 3.0 program (Smith et al, 2006). At the 3'-end of the aberrant exon, two SC35-binding motifs were predicted (data not shown). Hence, the first AON was designed such that it encompassed these two motifs (designated AON-3, SEQ ID NO. 11), and being complementary to the CEP290 mRNA.

To determine whether AON-3 has exon-skipping potential in vitro, immortalized lympoblastoid cells of two unrelated individuals with LCA homozygously carrying the intronic CEP290 founder mutation c.2991+1655A>G, as well as one control individual were cultured in the absence or presence of 1 µM AON-3. As expected, in the control individual, only a band representing correctly spliced CEP290 was observed, whereas in both affected individuals two products were present, one representing correctly spliced, and one representing aberrantly spliced CEP290 mRNA. Upon addition of AON-3, a strong decrease in aberrantly spliced CEP290 was noted, in both individuals with LCA (FIG. 2a). Next, the specificity of AON-3 was assessed by transfecting a sense oligonucleotide directed to the same target site (SON-3, SEQ ID NO: 14). RT-PCR analysis showed that in the cells transfected with SON-3, both the aberrantly spliced and the correctly spliced CEP290 mRNA molecules are still present (FIG. 2b, left panel), demonstrating the specificity of the antisense sequence. Using an additional pair of primers that amplifies larger products, similar results were obtained (FIG. 2b, right panel). Interestingly, the decrease in aberrantly spliced CEP290 appears to coincide with an increased intensity of the product representing correctly spliced CEP290 mRNA. These data indicate that the aberrant product is not degraded, but that the AON transfection truly induces exon skipping, resulting in the synthesis of more correctly spliced wild-type CEP290 mRNA. To determine the effective dose of AON-3, cells were transfected with various concentrations of AON-3, ranging from 0.01 to 1.0 µM. Even at the lowest concentration of 0.01 µM, a marked reduction in aberrantly spliced CEP290 was observed. The maximum amount of exon skipping was observed at 0.05 or 0.1 µM of AON, indicating that these concentrations are sufficient to convert almost all aberrantly spliced CEP290 (FIG. 2c).

The effectiveness of AONs in splice modulation is thought to merely depend on the accessibility of the target mRNA molecule, and hence may differ tremendously between neighboring sequences. To determine whether this sequence specificity also applies for CEP290, several AONs were designed that target the aberrant CEP290 exon (Table 1). This exon consists of 128 base pairs, the majority of which are part of an Alu repeat, one of the most frequent repetitive elements in the human genome (Schmidt et al, 1982), covering the entire 5'-end of the aberrant exon (FIG. 3a). Hence, the majority of AONs were designed to be complementary to the 3'-end of the aberrant exon or the splice donor site (FIG. 3a). In total, five AONs were transfected at a final concentration of 0.1 µM, which was shown to be optimal for AON-3. Interestingly, besides AON-3, also AON-2 (SEQ ID NO: 10) and AON-4 (SEQ ID NO. 12) resulted in high levels of exon skipping. In contrast, AON-1 (SEQ ID NO: 9) that targets the Alu repeat region, and AON-5 (SEQ ID NO: 13) that is directed against the splice donor site, hardly showed any exon skipping potential (FIG. 3b). These data demonstrate the sequence specificity in AON-based exon skipping of CEP290 and highlight a small region of the aberrant CEP290 exon as a potential therapeutic target.

Discussion

In this study, we explored the therapeutic potential of AONs to correct a splice defect caused by an intronic mutation in CEP290. In immortalized lymphoblast cells of LCA patients homozygously carrying the intronic CEP290 mutation c.2991+1655A>G, transfection of some but not all AONs resulted in skipping of the aberrant exon, thereby almost fully restoring normal CEP290 splicing.

AONs have been the focus of therapeutic research for over a decade, for the treatment of a variety of genetic diseases (Hammond et al, 2011). These strategies include the use of AONs to block the recognition of aberrant splice sites, to alter the ratio between two naturally occurring splice isoforms, to induce skipping of exons that contain protein-truncating mutations, or to induce the skipping of exons in order to restore the reading-frame of a gene that is disrupted by a genomic deletion, allowing the synthesis of a (partially) functional protein (Hammond et al. 2011). The latter approach is already being applied in phase I/II clinical trials for the treatment of patients with Duchenne muscular dystrophy, with promising results (Kinali et al, 2009; van Deutekom et al, 2007).

The intronic CEP290 mutation is an ideal target for AON-based therapy, since this mutation results in the inclusion of an aberrant exon in the CEP290 mRNA which is normally not transcribed. Inducing skipping of this aberrant exon by AONs fully restores the normal CEP290 mRNA, allowing normal levels of CEP290 protein to be synthesized. A second major advantage is that although this AON-approach is a mutation-specific therapeutic strategy, the intronic CEP290 mutation is by far the most frequent LCA-causing mutation.[4] Based on the estimated prevalence of LCA (1:50,000), and the observed frequency of the intronic CEP290 mutation in Northern-Europe (26%) (Coppieters et al. 2010) and the U.S. (10%) (Stone, 2007), at least one thousand and, depending on the frequency of the mutation in other populations, perhaps many more individuals worldwide have LCA due to this mutation. Finally, although the LCA phenotype associated with CEP290 mutations is severe, it appears that the photoreceptor integrity, especially in the macula, as well as the anatomical structure of the visual connections to the brain, are relatively intact in LCA patients with CEP290 mutations, which would allow a window of opportunity for therapeutic intervention (Cideciyan et al, 2007).

The study described here provides a proof-of-principle of AON-based therapy for CEP290-associated LCA in vitro, using immortalized patient lymphoblast cells. In order to determine the true therapeutic potential of this method for treating LCA, additional studies are needed that include the development of therapeutic vectors, and assessment of efficacy and safety in animal models. Although naked AONs, or conjugated to cell-penetrating peptides, can be delivered to the retina by intraocular injections, the limited stability of the AONs would require multiple injections in each individual. In contrast, by using viral vectors, a single subretinal injection would suffice to allow a long-term expression of the therapeutic construct. Previously, others have used recombinant adeno-associated viral (rAAV) vectors carrying U1- or modified U7snRNA constructs to efficiently deliver AON sequences, in the mdx mouse model for DMD, or in DMD patient myoblasts, respectively (Geib et al, 2009; Goyenhalle et al, 2004). In line with this, AONs targeting the aberrant exon of CEP290 could be cloned within such constructs, and delivered to the retina by subretinal injections of rAAV-5 or -8 serotypes that efficiently transduce photoreceptor cells where the endogenous CEP290 gene is expressed (Alloca et al, 2007; Lebherz et al, 2008). Using rAAV-2 vectors, no long-lasting immune response was evoked upon subretinal injections of these vectors in patients with RPE65 mutations (Simonella et al, 2009), and also for rAAV-5 and rAAV-8, immune responses appear to be absent or limited, at least in animal models (Li et al, 2009; Vandenberghe et al, 2011). One final safety aspect concerns the specificity of the sequence that is used to block the splicing of the aberrant CEP290 exon. As stated before, the majority of this exon is part of an Alu repeat, and AONs directed against this repeat will likely bind at multiple sites in the human genome, increasing the chance to induce off-target effects. The AONs that were shown to be effective in this study do not fully target the Alu repeat sequence, but are also not completely unique in the human genome. However, when blasting against the EST database, no exact hits are found, indicating that at the level of expressed genes, these sequences are unlikely to induce off-target effects and deregulate normal splicing of other genes. To further study the efficacy and safety of AON-based therapy for CEP290-associated LCA in vivo, we are currently generating a transgenic knock-in mouse model that carries part of the human CEP290 gene (exon 26 to exon 27, with and without the intronic mutation) which is exchanged with its mouse counterpart. Compared to gene augmentation therapy, AON-based therapy has a number of advantages. First, in gene augmentation therapy, a ubiquitous or tissue-specific promoter is used to drive expression of the wild-type cDNA encoding the protein that is mutated in a certain patient. For instance in one clinical trial for RPE65 gene therapy, the chicken beta-actin promoter was used (Maguire et al, 2008). Using these but also fragments of the endogenous promoters, it is difficult to control the levels of expression of the therapeutic gene. In some cases, like for the RPE65 protein that has an enzymatic function, expression levels beyond those of the endogenous gene might not be harmful to the retina. For other genes however, including those that encode structural proteins like CEP290, tightly-regulated expression levels might be crucial for cell survival, and overexpression of the therapeutic protein might exert toxic effects. Using AONs, the therapeutic intervention occurs at the pre-mRNA level, and hence does not interfere with the endogenous expression levels of the target gene A second issue is the use of the viral vector. Of a variety of different recombinant viral vectors, rAAVs are considered to be most suitable for treating retinal dystrophies, because of their relatively high transduction efficiency of retinal cells, and their limited immunogenicity. The major drawback of rAAVs however is their limited cargo size of 4.8 kb. Again, for some genes like RPE65, this is not a problem. For many other retinal genes however, like CEP290 (with an open reading frame of 7.4 kb), but also ABCA4 and USH2A, the size of their full-length cDNAs exceeds the cargo size of the currently available pool of rAAVs. One way to overcome this problem is to express cDNAs that express only partial proteins with residual activity, as has been suggested for CEP290 by expressing the N-terminal region of CEP290 in a zebrafish model (Baye et al, 2011). Other viral vectors, like lentivirus or adenoviruses have a higher cargo capacity that rAAVs (~8 kb), but are less efficient in transducing retinal cells, and adenoviruses have a higher immunogenic potential (den Hollander et al. 2010). For AON-based therapy, the size limitations of AAV are not a problem, since the small size of the AONs and the accompanying constructs easily fit within the available AAVs.

In conclusion, this study shows that administration of AONs to cultured patient cells almost fully corrects a splice defect that is caused by a frequent intronic mutation in CEP290 that causes LCA. These data warrant further research to determine the therapeutic potential of AON-based therapy for CEP290-associated LCA, in order to delay or cease the progression of this devastating blinding disease.

REFERENCE LIST

1. Leber, T. (1869). Uber Retinitis Pigmentosa und angeborene Amaurose, von Graefe's Archives Ophthalmology 15, 1-25.
2. Koenekoop, R. K., Lopez, I, den Hollander, A. I., Allikmets, R., and Cremers, F. P. (2007). Genetic testing for retinal dystrophies and dysfunctions: benefits, dilemmas and solutions. Clin Experiment Ophthalmol 35, 473-485.
3. Stone, E. M. (2007). Leber congenital amaurosis—a model for efficient genetic testing of heterogeneous disorders: LXIV Edward Jackson Memorial Lecture, Am J Ophthalmol 144, 791-811.
4. den Hollander, A. I., Roepman, R., Koenekoop, R. K., and Cremers, F. P. M. (2008). Leber congenital amaurosis: genes, proteins and disease mechanisms. Prog Retin Eye Res 27, 391-419.
5. Estrada-Cuzcano, A., Koenekoop, R. K., Coppieters, F., Kohl, S. Lopez, I., Collin, R. W. J., De Baere, E. B., Roeleveld, D., Marek, J., Bernd, A. et al (2011). IQCB1 mutations in patients with leber congenital amaurosis. Invest Ophthalmol Vis Sci 52, 834-839.
6. den Hollander, A. I., Koenekoop. R. K., Yzer, S., Lopez, I., Arends, M. L., Voesenek, K. E., Zonneveld, M. N., Strom, T. M., Meitinger, T., Brunner, H. G. et al (2006). Mutations in the CEP290 (NPHP6) gene are a frequent cause of Leber congenital amaurosis. Am J Hum Genet 79, 556-561.
7. Perrault, I., Delphin, N., Hanein, S., Gerber, S., Dufier, J. L., Roche, O., foort-Dhellemmes, S., Dollfus, H., Fazzi, E., Munnich, A. et al (2007). Spectrum of NPHP6/CEP290 mutations in Leber congenital amaurosis and delineation of the associated phenotype. Hum Mutat 28, 416.
8. Baala, L., Audollent, S., Martinovic, J., Ozilou, C., Babron, M. C., Sivanandamoorthy, S., Saunier, S., Salomon, R., Gonzales, M., Rattenberry, E. et al (2007). Pleiotropic effects of CEP290 (NPHP6) mutations extend to Meckel syndrome. Am J Hum Genet 81, 170-179.
9. Frank, V., den Hollander, A. I., Bruchle, N. O., Zonneveld, M. N., Nurnberg, G., Becker, C., Du, B. G., Kendziorra, H., Roosing, S., Senderek, J. et al (2008). Mutations of the CEP290 gene encoding a centrosomal protein cause Meckel-Gruber syndrome. Hum Mutat 29, 45-52.
10. Helou J., Otto, E. A., Attanasio, M., Allen, S. J., Parisi, M. A., Glass, L, Utsch, B., Hashmi, S., Fazzi, E., Omran, H. et al (2007). Mutation analysis of NPHP6/CEP290 in patients with Joubert syndrome and Senior-Loken syndrome. J Med Genet 44, 657-663.
11. Valente, E. M., Silhavy, J. L., Brancati, F., Barrano, G., Krishnaswami, S. R., Castori, M., Lancaster, M. A., Boltshauser, E., Boccone, L., Al-Gazali, L. et al (2006). Mutations in CEP290, which encodes a centrosomal protein, cause pleiotropic forms of Joubert syndrome. Nat Genet 38, 623-625
12. Coppieters, F., Casteels, I., Meire, F., De Jaegere S., Hooghe, S., van Regemorter N., Van Esch H., Matuleviciene, A., Nunes, L., Meersschaut, V. et al (2010). Genetic screening of LCA in Belgium: predominance of CEP290 and identification of potential modifier alleles in AHI1 of CEP290-related phenotypes. Hum Mutat 31, E1709-E1766.
13. Littink, K. W., Pott, J. W., Collin. R. W. J., Kroes, H. Y., Verheij. J. B., Blokland, E. A., de Castro Miro M., Hoyng, C. B., Klaver, C. C., Koenekoop, R. K. et al (2010). A novel nonsense mutation in CEP290 induces exon skipping and leads to a relatively mild retinal phenotype. Invest Ophthalmol Vis Sci 51, 3646-3652.
14. Bainbridge, J. W., Smith, A. J., Barker, S. S., Robbie, S, Henderson. R., Balaggan, K., Viswanathan, A., Holder, G. E., Stockman, A., Tyler, N et al (2008). Effect of gene therapy on visual function in Leber's congenital amaurosis. N Engl J Med 358, 2231-2239.
15. Cideciyan, A. V., Aleman, T. S., Boye, S. L., Schwartz, S. B., Kaushal, S., Roman, A. J., Pang, J. J., Sumaroka, A., Windsor, E. A., Wilson, J. M. et al (2008). Human gene therapy for RPE65 isomerase deficiency activates the retinoid cycle of vision but with slow rod kinetics. Proc Natl Acad Sci USA 105, 15112-15117.
16. Hauswirth, W., Aleman, T. S., Kaushal, S., Cideciyan, A. V., Schwartz, S. B., Wang, L., Conlon, T., Boye, S. L., Flotte, T. R., Byrne, B. et al (2008). Phase I Trial of Leber Congenital Amaurosis due to Estrada-Mutations by Ocular Subretinal Injection of Adeno-Associated Virus Gene Vector: Short-Term Results. Hum Gene Ther
17. Maguire, A. M., Simonelli, F., Pierce, E. A., Pugh, E. N., Jr., Mingozzi, F., Bennicelli, J., Banfi, S., Marshall. K. A., Testa, F., Surace, E. M. et al (2008). Safety and efficacy of gene transfer for Leber's congenital amaurosis. N Engl J Med 358, 2240-2248.
18. Maguire, A. M., High, K. A., Auricchio, A., Wright. J. F., Pierce, E. A., Testa. F., Mingozzi, F. Bennicelli, J. L., Ying, G. S., Rossi. S. et al (2009). Age-dependent effects of RPE65 gene therapy for Leber's congenital amaurosis, a phase 1 dose-escalation trial. Lancet 374, 1597-1605.
19. den Hollander, A. I., Black, A., Bennett, J., and Cremers, F. P. M. (2010). Lighting a candle in the dark, advances in genetics and gene therapy of recessive retinal dystrophies. J Clin Invest 120, 3042-3053.
20. Aartsma-Rus, A., Houlleberghs, H., van Deutekom, J. C., van Ommen, G. J., and 't Hoen, P. A. (2010). Exonic sequences provide better targets for antisense oligonucleotides than splice site sequences in the modulation of Duchenne muscular dystrophy splicing. Oligonucleotides 20, 69-77.
21. Aartsma-Rus, A., van, V. L., Hirschi, M., Janson, A. A., Heemskerk. H., de Winter, C. L., de, K. S., van Deutekom, J. C., 't Hoen, P. A., and van Ommen, G. J. (2008). Guidelines for Antisense Oligonucleotide Design and Insight Into Splice-modulating Mechanisms. Mol Ther
22. Smith, P. J. Zhang, C., Wang, J., Chew, S. L., Zhang, M. Q., and Krainer, A. R. (2006). An increased specificity score matrix for the prediction of SF2/ASF-specific exonic splicing enhancers. Hum Mol Genet 15, 2490-2508
23. Schmid, C. W. and Jelinek, W. R. (1982). The Alu family of dispersed repetitive sequences. Science 216, 1065-1070.
24. Hammond, S. M. and Wood, M. J. (2011). Genetic therapies for RNA mis-splicing diseases Trends Genet 27, 196-205.
25. Kinali, M., rechavala-Gomeza, V., Feng, L., Cirak, S., Hunt, D., Adkin, C., Guglieri, M., Ashton, E., Abbs, S., Nihoyannopoulos, P. et al (2009). Local restoration of dystrophin expression with the morpholino oligomer AVI-4658 in Duchenne muscular dystrophy: a single-blind, placebo-controlled, dose-escalation, proof-of-concept study. Lancet Neurol 8, 918-928.
26. van Deutekom, J. C., Janson, A. A., Ginjaar, I. B., Frankhuizen, W. S., Aartsma-Rus, A., Bremmer-Bout, M., Den Dunnen, J. T., Koop, K van der Kooi, A. J., Goemans, N. M. et al (2007). Local dystrophin restoration with antisense oligonucleotide PRO051. N Engl J Med 357, 2677-2686.
27. Coppieters, F., Lefever, S., Leroy, B. P, and De, B. E. (2010). CEP290, a gene with many faces: mutation overview and presentation of CEP290base. Hum Mutat 31, 1097-1108.
28. Cideciyan, A. V., Aleman, T. S., Jacobson, S. G., Khanna, H., Sumaroka, A., Aguirre, G. K., Schwartz, S. B., Windsor, E. A., He, S., Chang, B. et al (2007). Centrosomal-ciliary gene CEP290/NPHP6 mutations result in blindness with unexpected sparing of photoreceptors and visual brain: implications for therapy of Leber congenital amaurosis. Hum Mutat 28, 1074-1083.
29. Geib, T. and Hertel, K. J. (2009) Restoration of full-length SMN promoted by adenoviral vectors expressing RNA antisense oligonucleotides embedded in U7 snRNAs. PLoS One 4, e8204.
30. Goyenvalle, A., Vulin, A., Fougerousse, F., Leturcq, F, Kaplan, J. C., Garcia, L., and Danos, O. (2004). Rescue of dystrophic muscle through U7 snRNA-mediated exon skipping. Science 306, 1796-1799.
31. Allocca, M., Mussolino, C., Garcia-Hoyos, M., Sanges, D., Iodice, C., Petrillo, M., Vandenberghe, L. H., Wilson, J. M., Marigo, V., Suracc, E. M. et al (2007). Novel adeno-associated virus serotypes efficiently transduce murine photoreceptors. J Virol 81, 11372-11380.
32. Lebherz, C., Maguire, A., Tang. W., Bennett, J., and Wilson, J. M. (2008). Novel AAV serotypes for improved ocular gene transfer. J Gene Med 10, 375-382.
33. Simonelli, F., Maguire, A. M., Testa, F., Pierce, E. A., Mingozzi, F., Bennicelli, J. L., Rossi, S., Marshall, K., Banfi, S., Surace, E. M. et al (2009). Gene Therapy for Leber's Congenital Amaurosis is Safe and Effective Through 1.5 Years After Vector Administration. Mol Ther
34. Li, W., Kong, F., Li, X., Dai, X., Liu, X., Zheng, Q., Wu, R., Zhou, X., Lu, F., Chang, B. et al (2009). Gene therapy following subretinal AAV5 vector delivery is not affected by a previous intravitreal AAV5 vector administration in the partner eye. Mol Vis 15, 267-275.
35. Vandenberghe, L. H., Bell. P., Maguire, A. M., Cearley, C. N., Xiao, R., Calcedo, R., Wang, L., Castle, M. J., Maguire, A. C., Grant, R et al (2011). Dosage Thresholds for AAV2 and AAV8 Photoreceptor Gene Therapy in Monkey. Sci Transl Med 3, 88ra54.
36. Baye, L. M., Patrinostro, X., Swaminathan, S., Beck, J. S., Zhang. Y., Stone, E. M., Sheffield, V. C., and Slusarski, D. C. (2011). The N-terminal region of centrosomal protein 290 (CEP290) restores vision in a zebrafish model of human blindness Hum Mol Genet 20, 1467-1477.
37. Dorn and Kippenberger, Curr Opin Mol Ther 2008 10(1) 10-20
38. Nielsen, et al. (1991) Science 254, 1497-1500
39. Govindaraju and Kumar (2005) Chem. Commun, 495-497
40. Egholm et al (1993) Nature 365, 566-568
41. Morita et al 2001. Nucleic Acid Res Supplement No. 1: 241-242
42. Gorman L. et al, Stable alteration of pre-mRNA splicing patterns by modified U7 small nuclear RNAs. Proc Natl Acad Sci USA 1998; 95(9):4929-34
43. Suter D, et al, Double-target antisense U7 snRNAs promote efficient skipping of an aberrant exon in three human beta-thalassemic mutations. Hum Mol Genet 1999; 8(13):2415-23
44. Remington: The Science and Practice of Pharmacy, 20th Edition. Baltimore, Md.: Lippincott Williams & Wilkins, 2000

The invention claimed is:

1. A method for treating a CEP290-related disease or condition requiring modulating, splicing of CEP290 c.2991+1655A>G, the method comprising administering to a subject in need thereof an exon skipping antisense oligonucleotide that is sufficiently complementary to SEQ ID NO: 6, SEQ ID NO: 7, or SEQ ID NO: 8 to specifically bind to SEQ ID NO:6, SEQ ID NO:7, or SEQ ID NO:8, respectively.

2. The method according to claim 1, wherein said antisense oligonucleotide has a length from about 8 to about 128 nucleotides.

3. The method according to claim 1, wherein said antisense oligonucleotide comprises a sequence selected from the group consisting of SEQ ID NO: 10, SEQ ID NO: 11, and SEQ ID NO: 12.

4. The method according to claim 1 wherein said antisense oligonucleotide comprises a 2'-O alkyl phosphorothioate antisense oligonucleotide.

5. The method according to claim 1, wherein the 2'-O alkyl phosphorothioate antisense oligonucleotide is selected from the group consisting of 2'-O-methyl modified ribose (RNA), 2-O-ethyl modified ribose, 2'-O-propyl modified ribose, and/or substituted derivatives thereof.

6. The method according to claim 5, wherein the substituted derivatives are halogenated derivatives.

7. The method according to claim 1, wherein the disease or condition is Leber congenital amaurosis.

8. A method for treating a CEP290-related disease or condition requiring modulating splicing of CEP290 c.2991+1655A>G, the method comprising administering to a subject in need thereof a vector expressing an exon skipping antisense oligonucleotide when placed under conditions conducive to expression of the antisense oligonucleotide, wherein said antisense oligonucleotide is sufficiently complementary to SEQ ID NO: 6, SEQ ID NO: 7, or SEQ ID NO: 8 to specifically bind to SEQ ID NO:6, SEQ ID NO:7, or SEQ ID NO: 8, respectively.

9. The method according to claim 8, wherein said antisense oligonucleotide has a length from about 8 to about 128 nucleotides.

10. The method according to claim 8, wherein said antisense oligonucleotide comprises a sequence selected from the group consisting of SEQ ID NO: 10, SEQ ID NO: 11, and SEQ ID NO: 12.

11. The method according to claim 8, wherein the disease or condition is Leber congenital amaurosis.

* * * * *

SEQUENCE LISTING

<160> NUMBER OF SEQ ID NOS: 21

<210> SEQ ID NO 1
<211> LENGTH: 93203
<212> TYPE: DNA
<213> ORGANISM: Homo sapiens
<220> FEATURE:
<221> NAME/KEY: 5'UTR
<222> LOCATION: (1)..(909)
<223> OTHER INFORMATION: Intron from 318 to 882
<220> FEATURE:
<221> NAME/KEY: exon
<222> LOCATION: (910)..(1011)
<220> FEATURE:
<221> NAME/KEY: Intron
<222> LOCATION: (1012)..(1183)
<220> FEATURE:
<221> NAME/KEY: exon
<222> LOCATION: (1184)..(1261)
<220> FEATURE:
<221> NAME/KEY: Intron
<222> LOCATION: (1262)..(2652)
<220> FEATURE:
<221> NAME/KEY: exon
<222> LOCATION: (2653)..(2722)
<220> FEATURE:
<221> NAME/KEY: Intron
<222> LOCATION: (2723)..(3025)
<220> FEATURE:
<221> NAME/KEY: exon
<222> LOCATION: (3026)..(3072)
<220> FEATURE:
<221> NAME/KEY: Intron
<222> LOCATION: (3073)..(5430)
<220> FEATURE:
<221> NAME/KEY: exon
<222> LOCATION: (5431)..(5574)
<220> FEATURE:
<221> NAME/KEY: Intron
<222> LOCATION: (5575)..(10998)
<220> FEATURE:
<221> NAME/KEY: exon
<222> LOCATION: (10999)..(11052)
<220> FEATURE:
<221> NAME/KEY: Intron
<222> LOCATION: (11053)..(11651)
<220> FEATURE:
<221> NAME/KEY: exon
<222> LOCATION: (11652)..(11672)
<220> FEATURE:
<221> NAME/KEY: Intron
<222> LOCATION: (11673)..(11796)
<220> FEATURE:
<221> NAME/KEY: exon
<222> LOCATION: (11797)..(11949)
<220> FEATURE:
<221> NAME/KEY: Intron
<222> LOCATION: (11950)..(12340)
<220> FEATURE:
<221> NAME/KEY: exon
<222> LOCATION: (12341)..(12523)
<220> FEATURE:
<221> NAME/KEY: Intron
<222> LOCATION: (12524)..(13181)
<220> FEATURE:
<221> NAME/KEY: exon
<222> LOCATION: (13182)..(13271)
<220> FEATURE:
<221> NAME/KEY: Intron
<222> LOCATION: (13272)..(15778)
<220> FEATURE:
<221> NAME/KEY: exon
<222> LOCATION: (15779)..(15901)
<220> FEATURE:
<221> NAME/KEY: Intron
<222> LOCATION: (15902)..(16847)

```
-continued

<220> FEATURE:
<221> NAME/KEY: exon
<222> LOCATION: (16848)..(16971)
<220> FEATURE:
<221> NAME/KEY: Intron
<222> LOCATION: (16972)..(21050)
<220> FEATURE:
<221> NAME/KEY: exon
<222> LOCATION: (21051)..(21220)
<220> FEATURE:
<221> NAME/KEY: Intron
<222> LOCATION: (21221)..(21940)
<220> FEATURE:
<221> NAME/KEY: exon
<222> LOCATION: (21941)..(22103)
<220> FEATURE:
<221> NAME/KEY: Intron
<222> LOCATION: (22104)..(23473)
<220> FEATURE:
<221> NAME/KEY: exon
<222> LOCATION: (23474)..(23574)
<220> FEATURE:
<221> NAME/KEY: Intron
<222> LOCATION: (23575)..(23646)
<220> FEATURE:
<221> NAME/KEY: exon
<222> LOCATION: (23647)..(23734)
<220> FEATURE:
<221> NAME/KEY: Intron
<222> LOCATION: (23735)..(25071)
<220> FEATURE:
<221> NAME/KEY: exon
<222> LOCATION: (25072)..(25184)
<220> FEATURE:
<221> NAME/KEY: Intron
<222> LOCATION: (25185)..(27034)
<220> FEATURE:
<221> NAME/KEY: exon
<222> LOCATION: (27035)..(27119)
<220> FEATURE:
<221> NAME/KEY: Intron
<222> LOCATION: (27120)..(27654)
<220> FEATURE:
<221> NAME/KEY: exon
<222> LOCATION: (27655)..(27797)
<220> FEATURE:
<221> NAME/KEY: Intron
<222> LOCATION: (27798)..(30358)
<220> FEATURE:
<221> NAME/KEY: exon
<222> LOCATION: (30359)..(30523)
<220> FEATURE:
<221> NAME/KEY: Intron
<222> LOCATION: (30524)..(30865)
<220> FEATURE:
<221> NAME/KEY: exon
<222> LOCATION: (30866)..(31015)
<220> FEATURE:
<221> NAME/KEY: Intron
<222> LOCATION: (31016)..(33035)
<220> FEATURE:
<221> NAME/KEY: exon
<222> LOCATION: (33036)..(33151)
<220> FEATURE:
<221> NAME/KEY: Intron
<222> LOCATION: (33152)..(35118)
<220> FEATURE:
<221> NAME/KEY: exon
<222> LOCATION: (35119)..(35221)
<220> FEATURE:
<221> NAME/KEY: Intron
<222> LOCATION: (35222)..(35311)
<220> FEATURE:
<221> NAME/KEY: exon
<222> LOCATION: (35312)..(35542)
<220> FEATURE:
<221> NAME/KEY: Intron
<222> LOCATION: (35543)..(39205)
```

```
<220> FEATURE:
<221> NAME/KEY: exon
<222> LOCATION: (39206)..(39379)
<220> FEATURE:
<221> NAME/KEY: Intron
<222> LOCATION: (39380)..(45217)
<223> OTHER INFORMATION: Aberrant exon included in mutant CEP290 mRNA
      position 40902-41209 mutated nucleotide A>G in LCA patients at
      position 41034
<220> FEATURE:
<221> NAME/KEY: exon
<222> LOCATION: (45218)..(45329)
<220> FEATURE:
<221> NAME/KEY: Intron
<222> LOCATION: (45330)..(48241)
<220> FEATURE:
<221> NAME/KEY: exon
<222> LOCATION: (48242)..(48447)
<220> FEATURE:
<221> NAME/KEY: Intron
<222> LOCATION: (48448)..(49384)
<220> FEATURE:
<221> NAME/KEY: exon
<222> LOCATION: (49385)..(49536)
<220> FEATURE:
<221> NAME/KEY: Intron
<222> LOCATION: (49537)..(51377)
<220> FEATURE:
<221> NAME/KEY: exon
<222> LOCATION: (51378)..(51489)
<220> FEATURE:
<221> NAME/KEY: Intron
<222> LOCATION: (51490)..(52729)
<220> FEATURE:
<221> NAME/KEY: exon
<222> LOCATION: (52730)..(53185)
<220> FEATURE:
<221> NAME/KEY: Intron
<222> LOCATION: (53186)..(54272)
<220> FEATURE:
<221> NAME/KEY: exon
<222> LOCATION: (54273)..(54437)
<220> FEATURE:
<221> NAME/KEY: Intron
<222> LOCATION: (54438)..(55718)
<220> FEATURE:
<221> NAME/KEY: exon
<222> LOCATION: (55719)..(55826)
<220> FEATURE:
<221> NAME/KEY: Intron
<222> LOCATION: (55827)..(56043)
<220> FEATURE:
<221> NAME/KEY: exon
<222> LOCATION: (56044)..(56178)
<220> FEATURE:
<221> NAME/KEY: Intron
<222> LOCATION: (56179)..(57364)
<220> FEATURE:
<221> NAME/KEY: exon
<222> LOCATION: (57365)..(57631)
<220> FEATURE:
<221> NAME/KEY: Intron
<222> LOCATION: (57632)..(58262)
<220> FEATURE:
<221> NAME/KEY: exon
<222> LOCATION: (58263)..(58370)
<220> FEATURE:
<221> NAME/KEY: Intron
<222> LOCATION: (58371)..(58986)
<220> FEATURE:
<221> NAME/KEY: exon
<222> LOCATION: (58987)..(59186)
<220> FEATURE:
<221> NAME/KEY: Intron
<222> LOCATION: (59187)..(61821)
<220> FEATURE:
<221> NAME/KEY: exon
<222> LOCATION: (61822)..(62035)
```

```
<220> FEATURE:
<221> NAME/KEY: Intron
<222> LOCATION: (62036)..(62987)
<220> FEATURE:
<221> NAME/KEY: exon
<222> LOCATION: (62988)..(63125)
<220> FEATURE:
<221> NAME/KEY: Intron
<222> LOCATION: (63126)..(64298)
<220> FEATURE:
<221> NAME/KEY: exon
<222> LOCATION: (64299)..(64520)
<220> FEATURE:
<221> NAME/KEY: Intron
<222> LOCATION: (64521)..(64872)
<220> FEATURE:
<221> NAME/KEY: exon
<222> LOCATION: (64873)..(64995)
<220> FEATURE:
<221> NAME/KEY: Intron
<222> LOCATION: (64996)..(70290)
<220> FEATURE:
<221> NAME/KEY: exon
<222> LOCATION: (70291)..(70436)
<220> FEATURE:
<221> NAME/KEY: Intron
<222> LOCATION: (70437)..(70767)
<220> FEATURE:
<221> NAME/KEY: exon
<222> LOCATION: (70768)..(70923)
<220> FEATURE:
<221> NAME/KEY: Intron
<222> LOCATION: (70924)..(73571)
<220> FEATURE:
<221> NAME/KEY: exon
<222> LOCATION: (73572)..(73695)
<220> FEATURE:
<221> NAME/KEY: Intron
<222> LOCATION: (73696)..(78101)
<220> FEATURE:
<221> NAME/KEY: exon
<222> LOCATION: (78102)..(78236)
<220> FEATURE:
<221> NAME/KEY: Intron
<222> LOCATION: (78237)..(79438)
<220> FEATURE:
<221> NAME/KEY: exon
<222> LOCATION: (79439)..(79525)
<220> FEATURE:
<221> NAME/KEY: Intron
<222> LOCATION: (79526)..(81222)
<220> FEATURE:
<221> NAME/KEY: exon
<222> LOCATION: (81223)..(81387)
<220> FEATURE:
<221> NAME/KEY: Intron
<222> LOCATION: (81388)..(82196)
<220> FEATURE:
<221> NAME/KEY: exon
<222> LOCATION: (82197)..(82319)
<220> FEATURE:
<221> NAME/KEY: Intron
<222> LOCATION: (82320)..(83196)
<220> FEATURE:
<221> NAME/KEY: exon
<222> LOCATION: (83197)..(83369)
<220> FEATURE:
<221> NAME/KEY: Intron
<222> LOCATION: (83370)..(86499)
<220> FEATURE:
<221> NAME/KEY: exon
<222> LOCATION: (86500)..(86641)
<220> FEATURE:
<221> NAME/KEY: Intron
<222> LOCATION: (86642)..(87803)
<220> FEATURE:
<221> NAME/KEY: exon
<222> LOCATION: (87804)..(87877)
```

```
<220> FEATURE:
<221> NAME/KEY: Intron
<222> LOCATION: (87878)..(88470)
<220> FEATURE:
<221> NAME/KEY: exon
<222> LOCATION: (88471)..(88565)
<220> FEATURE:
<221> NAME/KEY: Intron
<222> LOCATION: (88566)..(91783)
<220> FEATURE:
<221> NAME/KEY: exon
<222> LOCATION: (91784)..(91863)
<220> FEATURE:
<221> NAME/KEY: Intron
<222> LOCATION: (91864)..(92802)
<220> FEATURE:
<221> NAME/KEY: exon
<222> LOCATION: (92803)..(93033)
<220> FEATURE:
<221> NAME/KEY: 3'UTR
<222> LOCATION: (93034)..(93203)

<400> SEQUENCE: 1
atttgaagtc ctcgttccac gccttctcat catcctgaac accgagctct gggactccgg       60
cggagaatct aaacgtaaag catcacccac ggtcgtgaac tgtaggctct cctggcatcc      120
gggatcttat tctggccttg gcggagttgg ggatggtgtc gcctagcagc cgctgccgct      180
ttggcttgct cgggaccatt tggctggacc cagagtccgc gtggaaccgc gatagggatc      240
tgtcagggcc cgcggccggg tccagcttgg tggttgcggt agtgagaggc ctccgctggt      300
tgccaggctt ggtctaggtg ggtggatcct tgtaagcagg attagcgagt cactccacgc      360
tcaggttctt tagcctgagg gcccgtgtgc cacagcatag ctaccccgcc cttccagcct      420
cgggtcccta atactgcctt gcttcggttc cagtttccgc cgcacaactt cactcattcc      480
aaatgttaat ttctgcgttt ttttcagcc ccaattctgt ttctccaaat cagggatgat       540
tgtcggcctt ccacagaccc tcgcgcttgc caggattagg gtgttcgcgc gcattgtggg      600 tagggtgtg gaggaaggga tccagaaatc ttaagtatta acttagatta gtgttagcaa       660
ggaagccgtc acatttttatt tagccgggac actctgacag tttgtgccga ctgctatttt     720
tgatcaaggc tattttgccc acttgtctat tttgtggccc aattgtctgt tttgctaaca      780
tcagaaagtt ataatgaaat aatctgcaaa aaatgtaagg tgctagaaaa ccaataatac      840
tgtgtacctt gaaatgcta atatacacct gttttgttac agaggtggag cacagtgaaa       900 gaattcaag atg cca cct aat ata aac tgg aaa gaa ata atg aaa gtt gac      951
         Met Pro Pro Asn Ile Asn Trp Lys Glu Ile Met Lys Val Asp
           1               5                  10 cca gat gac ctg ccc cgt caa gaa gaa ctg gca gat aat tta ttg att        999
Pro Asp Asp Leu Pro Arg Gln Glu Glu Leu Ala Asp Asn Leu Leu Ile
15                   20                  25                  30 tcc tta tcc aag gtgcttaatt ggtcaataat aatagatata tacattaact            1051
Ser Leu Ser Lys tatgattaat ttattaataa aatatgaatt tattttttc agggacaact ataattgtca       1111
caatctggaa gtgttcttat attttgcttg aaggttataa aatataaaac agttgctttt      1171
ctgtttactt ag gtg gaa gta aat gag cta aaa agt gaa aag caa gaa aat      1222
              Val Glu Val Asn Glu Leu Lys Ser Glu Lys Gln Glu Asn
                  35                  40                  45 gtg ata cac ctt ttc aga att act cag tca cta atg aag gtttgtatgt         1271
Val Ile His Leu Phe Arg Ile Thr Gln Ser Leu Met Lys
50                  55                  60
```

```
agtaggtttt aactataggt ttggctatta gtggaactat aaaaatctgt tcttatataa  1331
ggtaatcttt gtgaaaatac ctggtaatat ctacatcacc actaaaaaat gcaatatatt  1391
taaatgtgaa ttaagtattt tagtgtataa aacattgcta gtttctactt aaagtttcta  1451
aaagggtgtg taggggaaat agaatgagta tgttgaaaag taacataagg aaatatatct  1511
tgaggtccaa atgacaaatg cagacaatga ctgctatagg gatttgttaa gagggggaaat 1571
gatttaagag atgtcagaag acttcacaaa ggatcaatac tgaggagtag tgttagataa  1631
gtggaaggca atgcagtggt aagatagtaa gggaattcta gagctgttgg ttaccataaa  1691
taaatactga gaacaggaaa tatgtttatt ctttatattt gaggaaacaa ggtgcagcaa  1751
gtttgtagca gactgtagag aaaacaaatc ttgggtaagt actttgagat aggttgttga  1811
gggccttaaa ggtgtatttt atgctatcag caattgagaa ggcagtaaag gttttcgaaa  1871
cacaattgat aggtacaaaa atacacctta agaaggcaaa actgagtata ttatgtagga  1931
caaactgaag gaaattggag ctttgtagac atcacattat agcggagttt aaacctgaaa  1991
ttatggatta gaataatagc aattggaaca gaaaaaaagt agtggaaaga cattacaaag  2051
ggagatgttg cattactgga tataagactt gaggacttga ggtaaaaagg agaatcaaaa  2111
atgtttcatg ctattaaaaa tctagaaatt gtagtcttaa gtaagaaaat tgcctggcat  2171
ggtggctcac gtctgtaatc ccagcacttt gggaggccaa ggcaggagga ttgcttgagc  2231
ctgggagttc aagactagcc tggataatat agtgagtcct tgcctgtacg aaaaaatttg  2291
ccgagcatga tggcacacca agcatgatgg cacgccaagc atgatggcat gcacctgtag  2351
tcccagctac tcaggagact gagatgggaa gattgcttga gcccaggagg caggaggttg  2411
cagtgagctg agattgtgcc actgcactcc agcctgggtg acaaagtgag gccctatctc  2471
aaaagcaaaa aaaacaaaaa caaaaaccaa aaactattta ttcagcaaat atttactgaa  2531
cgtctccatg tgccagccat tgctggcact aaggatcata acaaataaaa cagaattttt  2591
attttcagtg cttacattcc agtataaagg catattgaaa taacctttt ttaatgttta   2651
g atg aaa gct caa gaa gtg gag ctg gct ttg gaa gaa gta gaa aaa gct  2700
  Met Lys Ala Gln Glu Val Glu Leu Ala Leu Glu Glu Val Glu Lys Ala
            65                  70                  75
gga gaa gaa caa gca aaa ttt g gtaagcacct tggaaaaagt ttattatggt      2752
Gly Glu Glu Gln Ala Lys Phe
    80
attaaataat gaattccatt tgttcattaa actgtagaaa attaaattat attctataaa  2812
atatatatat tcagtttatt tttaatatat aacatttaat aataaatatt tctagactcc  2872
tattttatgg atctgccata taatactttt tgttacctta taatcatgat ggactctttt  2932
aaaagaatta attttgttat tgaaatttat ttaaagtttt gttttgtggt aactaatcaa  2992
ttaaaacgtt tttctttttt tttaaaaaaa tag aa  aat caa tta aaa act aaa  3045
                                    Glu Asn Gln Leu Lys Thr Lys
                                       85                  90
gta atg aaa ctg gaa aat gaa ctg gag gtatgtcttt ttgtattccc           3092
Val Met Lys Leu Glu Asn Glu Leu Glu
       95
taggatgtaa ttgtcattaa tttttatttttg aattgttttc aaattttaaa attattgttg 3152
gctggaaaaa ttataaggat gattgtaatc atggttattt gtttattctg tatatgttct  3212
acatgcctat tatgtgcctt atatagtact aaggactgag catatggttg tgaacaaaat  3272
aagaagttaa ctgctggatg gagccttatag tcttgggaaa tatacagaaa gattactagt  3332
aactgaggtg gagggtgggt ggggatttga ggaatagtga cgaaagggtg ttatagaagt  3392
```

```
aatttttgac aaagctgaag gctaaaatat gaatgtattg ttgaagaaca aaatacattg    3452
agattcctga gaaggtagga atgtgataca aatggatcag cctttgaaag gaggaatacc    3512
cttttccttt gtgttaggag aggaggatga gtggatgagc gtgggaagag tggatgtgta    3572
tagaggcttt tatgtttgta ggcataatgc ttggaagttg aggggttggt gatgacatct    3632
tctgttaaaa agagtgggaa atggtgtggt cacattttaa ggaaattagg taaaatttga    3692
aatatattgg agacaggact ggagagttgg ggatctggag tcagacagat ttgagttcta    3752
gtcctgattc ttctactcgt taactctctg aacttggatg acctattgtt tttgattgta    3812
tatccagctc ctgggaaaat gccaagcact ttcaataaat actaaatgaa ttatggagtt    3872
ggatcagttc tgtgttagtg tttagctagg tagctgctgt agaatagaag ggtagcacag    3932
ttgaagatat tggtaggaaa gtggttgaag tgatgattat gaagtcttaa ctgaatagat    3992
aaaatcaaga ttggggttgg gtgggcagaa gggtagggat atggagggag aagatgaggg    4052
gttagagtgt cctgtgaggt cgaaggacag gcatagtggg aataattgaa agaatgttct    4112
ggttggacaa ggatctgatg tgggtgtggg agtgagagac tatagtgaat tcaagaaaaa    4172
aatagactag aacaaaagtt atgtggagat tgcttagtgg gcatttgata gacatctgtg    4232
ggccacatgc ttaaattccc agtgcatttt gcggagttac tggaaggttg gtggcttgtt    4292
tctaccatga gtaggtaaag atggagagca ggatattttg tgagaaagca gctgaagttt    4352
ctataggatg atggaggaat gataggaatg atcacctgaa gttgcagggt ggggtaaacc    4412
tagaagcacc aacaccttct tctgaccctc atgtatttgg aatctgaaag aatgagcacc    4472
ttccaattga aagagttcca agggcattag tatactaaag gatccaaatt gcagctaagc    4532
caaggagatg gaaaggagga ttcagtaaag aatctgagga tgtgaaatat taatttatct    4592
tggaagagaa ttttagagag cacaatgaaa tgcttttttgg aggagagaaa gagtaagaac    4652
aatttggtta aggtagagga ataacagaac tataaggtga agaaatgaat gtgagacaca    4712
ttagatgacc aaatgatttg atgttcttgg ccatgacctg aattaacaag actgtgaggt    4772
aaaatggatt taatcggcta caaatcttaa gataaccaaa acctgagctg tttaatatgg    4832
tagcactagc actaaccact tgtagctatt tatatttaca ttggttaaaa ttaaaatgaa    4892
aaatttagtt cttcagttgc actagccaca cttcaaatgc ccgaacatag ctacatgtag    4952
cgagtggcta ttgaactgga cagcactgac agcatgtcca ttatgctaga aagtcctatg    5012
ggacagcact ggtctaaaca gtgcatggta tgagagaaag ggcaggttaa ggcactcagc    5072
ttcactgact ggggtggaga ttctgatggt ttgtactcag gttccagatc cctgaggctc    5132
aggaaccttt gcagtttagt ctggttacct gtggcccagt ggttacaaca gaatgattaa    5192
cagtcaattc tttgcatctc tgggtggctc aggaaaaatt taaggagtta ttagctgtga    5252
actaaccttta agtaagttaa attaaaaaaa aaaagttct taagctaata tgattttaaa    5312
tatctgcact gaagtataat gcaaatttaa attcagcata attatttgct tgttgttgac    5372
tcatttgaac ctcaaaatat aatgggatta atttatactt tgggtttatt actttaag      5430
```

| | | | | | | | | | | | | | | | | |
|---|---|---|---|---|---|---|---|---|---|---|---|---|---|---|---|---|
| atg | gct | cag | cag | tct | gca | ggt | gga | cga | gat | act | cgg | ttt | tta | cgt | aat | 5478 |
| Met | Ala | Gln | Gln | Ser | Ala | Gly | Gly | Arg | Asp | Thr | Arg | Phe | Leu | Arg | Asn | |
| 100 | | | | | 105 | | | | 110 | | | | | 115 | | |

| | | | | | | | | | | | | | | | | |
|---|---|---|---|---|---|---|---|---|---|---|---|---|---|---|---|---|
| gaa | att | tgc | caa | ctt | gaa | aaa | caa | tta | gaa | caa | aaa | gat | aga | gaa | ttg | 5526 |
| Glu | Ile | Cys | Gln | Leu | Glu | Lys | Gln | Leu | Glu | Gln | Lys | Asp | Arg | Glu | Leu | |
| | | | 120 | | | | 125 | | | | | 130 | | | | |

| | | | | | | | | | | | | | | | | |
|---|---|---|---|---|---|---|---|---|---|---|---|---|---|---|---|---|
| gag | gac | atg | gaa | aag | gag | ttg | gag | aaa | gag | aag | aaa | gtt | aat | gag | caa | 5574 |
| Glu | Asp | Met | Glu | Lys | Glu | Leu | Glu | Lys | Glu | Lys | Lys | Val | Asn | Glu | Gln | |
| | | 135 | | | | | 140 | | | | | 145 | | | | |

```
gtaaagcact ttttttttcc atgaatcttc actgttcaag ttacctggct ttttattatt    5634
attggtaaca atatcaattt ttatattgta tgttatattt gaaaaatgat gtacacttat    5694
ctctaaggtt ttatatcact gttcattttg tcatcaccaa ttttaaaata taatggtact    5754
tctagtgaat atgacttgaa gattaattct ttatatttgg aagtacattt ttctcaggac    5814
atcaaacttg ttacctaaaa ttaatgcttt tgtctggaag attggtatca agtaactaat    5874
agattttcat aaagaagtga tcttctctagt gccatagttt attttgggta aaagttatat   5934
ttgttcattt caatgtattt atatgattag tagattcgca aatgaatctt tcgatatatt    5994
caataatggt taattaaata tcttgttttt ggttgtacct tattttatgt gagatatata    6054
tatatatgta tagttttga aaagttgtgt tcatgtcagc agtttataaa tcacatattt     6114
aaaataacat ttttaatgca tagtttttat tacctcgtta ttccttgtta taaactaata   6174
attcttgcag tgttcacttg aatttagttt taggaaaaaa gttttttgca gatcaacttg    6234
tatttcctgg aagaaaattt cctatttttac ctcagcttcc tatttaatgt attatttatt   6294
tatttactta acatttattt gttttttatt tcacctgaac tgttagtaaa cttagtaaaa    6354
tttggtgcct acatgtggta actgtcctgt cccttatact cagaaacgtt ttccacctttt   6414 gtgtccttta ggtcattgtt gtgttatatt ccatttattt tattttgtcc attgttctct    6474
cagaaattga gggtcataca ttttaagaaa acaatgatat gctatttaag agaatgtatc    6534
ataaattgat ttgtaaggaa aagtatcccc attcttcatg tatgtatttt actctaaaat    6594
gttgaagaat catatagaag ttagctatga aaacaatgtg gtagagaaag tatggatcga    6654
tgccacttaa atgttaggaa gaagctctta gagcattatc tgtttagcta actgcaaaac    6714
atagcagaca tgtggatttt ttaatagtca tcaaggatct aacttataat atacactggt    6774
agaattgctt aggggggatgt ctgtggtttt ctggactttt gttcttctat atagacctgt    6834
atcagttgac ttatcattca taccacacac ccttagctaa tcagaactac cttgtccatt    6894
tatatcttag actattgtct tttttcatag tcacacacag agaaacttg aatatatggc    6954 ctgtgttcct ttttggctgc tcaattcctt gagatgaaat atgggtatgg gttgctttgg    7014
caattacttc tttgccgtta accagtcatt cagttttatt gagtctttac agcataccag    7074
aggctgctag ttactagtga tatagtgggc aactatgttc tggttctcaa gaatattcat    7134
agtcaataat aagcataaca tagtgataat atgatactta gggagataca taaggtcata    7194
ttctggcata ctctggagag agataccgta atcagccttg aggtgcagga tgtgatctgt    7254
aaactgagac ctgaagtata gttagactgg taagaggaat gaggatatat atggtggtta    7314
ataaaagaac attctgggta gaagatatag catttgctaa gacctagagg taagagatgt    7374
tatggagtat ttaggaaact acagttattc attttgactg aaatataagt gaaaatagct    7434
ttcatagagt ccttactatg tgccaggcac ttcatatgca ttaattcatt attgcttatt    7494
tgatacttgt catatgagat agttgtcatt tctgccatga tacagatgaa gaaatggaga    7554
cacagaaaga gtaattgccc atggttgcac agcttataaa tggtaaaggt aggatttgaa    7614
aacagtctta ctcaagagtc tgtgctatct tgccttccca gttttatttt ttatgatcct    7674
ctggagagat aagcaagggc cagttcctaa tgaatttggt tcttttcctg aaaggagcca    7734
gtgaagagtt ttgagcacag gatatcatga tcagatctat actttaaaag tttactgtac    7794
tttgtagaga gtggattgaa aagggccaag actagtaagg aaacatttgt gttaattcag    7854
ggaagtgcta atgatggcat ttgcctgaga aagacaagtg tgagagaagt agatgtaatt    7914
```

-continued

```
ggatgtggtg aatgtaattg gttgttggag gagagggagg atggagagtc tgcctaattt   7974
tgtgggttgg gccactaaat aggtagatag tgccattcat taaggaggaa cacaagagga   8034
atttggaaag cttgagatta tttcagtttt gtagatgttg agtttgaggt tcttctgggc   8094
atattcaaaa agggtatctg tggatatgga attcacaaga gaccctgtac agatgatgag   8154
gatttatgaa tcatcaatgt agacattatt gaagccagag aagtgattgt aaggcacgtc   8214
tctgagaaat gtctaataaa gcaatgaaat aggaagagtg cttcaaggaa aagctcaaga   8274
aaggagaaac agagtgtgat gtttgagaag acaagggaaa aaacattaa tagcattaaa    8334 tgctttagca ttaagttctt ggcttctctt cttgtaaaaa tttcccaatt cagaacacag   8394
tgggattatt aactttcaat tgataataat aatgataggc aaacttctaa aatttgtatt   8454
gtagtttgca ttttattata aactttcttt aaattttat tttgaaaaat gtcatatctt    8514
cataaagatt gtaagaaaca cactgttggt gttaatgtaa attagttcaa ccattgtggg   8574
agacagtgtg gcaattcctc gaagatctag aagcagaaat accacttgac ccagcaatcc   8634
cattactggg tatatacccca aaagaatata atcattttc ttataaagat acttgcacac    8694
atatgttcat tgcagcacta ttcacaatag caaagacatg gaatcaaccc aaatgctcat   8754
caatgataga ctggataatg aaaatgtgga acatatacat catagaatac tatgcagcca   8814
tcaaaagaga atgagaggtc aagcgtggtg actcatgcct acagtcccag cactttggga   8874
ggccgaggca ggcagatcac ttgaggtcag gagttcaaga ccagcctggc cagtatggtg   8934 aaacccccatc tctacaaaaa caaaacaaaa caaacaaaaa ttaactggtc atggtactgt   8994
atgcctgcag tcccagctac ttgggaggct gaggcaggag aatgacttga acccagaagg   9054
cagaggttgc agtgagctga gatcgcacca ctggactcta gccttagcaa caaaactaga   9114
gtttgtctca aaaaaaaaaa aaaaaaaaaa ccggaacaag atcatgtcct ttgcagggac   9174
atgggatgga ggtggaagcc attatcctca gcaaactcac acaggaacag aaaaccaaac   9234
actgcatgtt ctcacttata agtgggagct gaacaatgag aacacatgga cacatggtgg   9294
ggaacaacac acactgggac ccgtcaaggg gtcggggtgg gagaacatca ggaagaatag   9354 ctaatgggatg ctgggcttaa tatctaggtt atgggttgat ctgtgcagca agccaccatt   9414
gtacacattt acctaagtaa caaacctgca catcttacac atgtaccccca gaacttaaaa   9474 gttgatggga aaagaaaaa caataaccac ccacataccc ttcatataga ttcaccagtt    9534
cttaatgttg tgccaacttt gctttatctt tttgtcagta ttttttacaca cacatgtatt   9594 tctctgtctc ttgtttgttc aatcacattt tttgctgagt catttaagag ctaattgcag   9654
atatgatact ttgcacttaa atatttcagc ttgtctgttt gaaaagaaa gatgttctcc    9714 tacaatgaac acaatataat tgtcatgctc aggaatttta atattgattc aacaccatta   9774
tctagtccat aatgagattt cttctaatgg cccaataata tccttcagtc tccccacctc   9834
caatatccaa agttctgtca aggatcacat actacatttg gttctttatt atagactttt   9894
taaatatcgt tgtataccat tgtgattcta tcgtctcctt taataaagag gagaaccaga   9954
aaaatgaaag gtcataagag gaatgaggtt tggagaatag gtgaaaaaag gcatcataat   10014
gtttataata atgtttgcct gttcagagaa acaagaatca cagataaagt cacttatatg   10074
tagataagag aatgctgtat tacttttgc tattctattc actgatcatt tttctaagaa    10134
ctctgtatgc ttcttgttta actcttatgt cagcatgtat gagaaaactg agttaaagag   10194
atgttaagta actcattcat gctttactag aaattggttg atgagggaca taaacctagg   10254
ccggtgtgat tttagattgc ttcttttaac cattgtgttg tattgcctta tatttctaag   10314
```

```
taatttatgt tcactgagag caaataatag tctagctatg acttagaaaa gtaaaataaa    10374
gatgttgggc agaaaaccat tttattaggg gttttttttgg aggagcagat taatttgttt    10434
ctgtattctt tggttagttt gtgtgtgtgt tcttttttaat tctttaaaat gaaactgttt    10494
aatccttaaa tccttaagtt ttgaaaattt tggcctatta tttatgtgtt aggttgatat    10554
taaatcctta atagctttaa cattttctac tttgttagag aggatttaaa atttaagtag    10614
ataagctgaa tatctggctt tatattaaat tactgctgat ggccaggcac agtggctcat    10674
gtctgaaatc ctagcacttt gggaggttga ggcagatgga tcacttgagg ccaggagttc    10734
aagaccagcc tggctaacac agtgaaaccc cgtctctact aaaaatacaa aaattagcca    10794
gttatggtaa tgcatgccag taattccagc tactcggtag gctgaggtgg gagaattgct    10854
tgaaccggga ggcagaggtt gcagtgagcc gagatcgcac cactgtactc cagcctaggc    10914
gacaaagact ttgtctcaaa aaaaaaaaaa attactgctg aatttttatct tcttcttatt    10974 tatttttttt ttttactatt ttag ttg gct ctt cga aat gag gag gca gaa    11025
              Leu Ala Leu Arg Asn Glu Glu Ala Glu
                  150                 155 aat gaa aac agc aaa tta aga aga gag gtaaaaaatt ttagtagttg             11072
Asn Glu Asn Ser Lys Leu Arg Arg Glu
    160             165 tggtggttca acaaaggtac ttattaaaat aagtacctaa gtttacataa atttatattt    11132
taaccaggac tggagtcttc taagtaactg atgttttcag actgattta tggtatgact    11192 ttgtctcagg gaaatagaaa acaaagcaaa atgtgaggcc attaagtatt acattcatct    11252
caggtctatg cgggtaaatc tttttttgtt gttttataag ccattctttg ctagttttct    11312
aattgaatag atgactggat ttctattctt atttctctta cccagaatcc tttaaaattt    11372
tttgttactt gtggaatctt ataaattctg attatcattt ggttctactg agccaaataa    11432
tgtttgtaca ttgtttattc tgatagaagt tcttaagttt ctaacataat tgaaatatta    11492
tttgttttgg tagataatta gtattctttc tttggttatt caagataata tgcatcattt    11552
tcccaaaatt ttttttgtttt ctttagtttc tgattattat ttttaattat gtattacctt    11612
tctcatttct aattaccgtt ttcctgtcct tttctgtag aac aaa cgt cta aag        11666
                                        Asn Lys Arg Leu Lys
                                                         170 aaa aag gtgaggcttt aagtgtggtg aaatcttggg aatttaaaat atgttgtgag        11722
Lys Lys agcactattt agaggatatg attttgttat tctgaatagt tttgtaattg aatgttgtgt    11782
ttggttacct tcag aat gaa caa ctt tgt cag gat att att gac tac cag       11832
                Asn Glu Gln Leu Cys Gln Asp Ile Ile Asp Tyr Gln
                                    175                 180 aaa caa ata gat tca cag aaa gaa aca ctt tta tca aga aga ggg gaa       11880
Lys Gln Ile Asp Ser Gln Lys Glu Thr Leu Leu Ser Arg Arg Gly Glu
185                 190                 195                 200 gac agt gac tac cga tca cag ttg tct aaa aaa aac tat gag ctt atc       11928
Asp Ser Asp Tyr Arg Ser Gln Leu Ser Lys Lys Asn Tyr Glu Leu Ile
            205                 210                 215 caa tat ctt gat gaa att cag gtaaaatggc tagaagtcaa ttcagagcaa          11979
Gln Tyr Leu Asp Glu Ile Gln
                220 tggttcctaa aaactttaat ttcattacaa tgtaaatata atatttagcc ctacatgtaa    12039 attccctggt ataatctgt cactatgtac ttgtaaaatg tgaaataaat tacatctttg     12099 aagttgcaac tttttagcca ttttttatatt tgcctgtctt ggtcattaag aacaattgag  12159
```

```
gtccttatgt actattttct tgattcaatt tgatttaatt ggtcaatgcc aattagtaaa   12219
ggtctataaa gaattctctt tttttctaga ggacacttat ggctgcgttt aattttaatt   12279
tggtttaaat ttcagttttt ttaaaattac tttttaatta tagtgtcttt aactttttta   12339 g act tta aca gaa gct aat gag aaa att gaa gtt cag aat caa gaa atg   12388
  Thr Leu Thr Glu Ala Asn Glu Lys Ile Glu Val Gln Asn Gln Glu Met
      225                 230                 235 aga aaa aat tta gaa gag tct gta cag gaa atg gag aag atg act gat    12436
Arg Lys Asn Leu Glu Glu Ser Val Gln Glu Met Glu Lys Met Thr Asp
240                 245                 250                 255 gaa tat aat aga atg aaa gct att gtg cat cag aca gat aat gta ata    12484
Glu Tyr Asn Arg Met Lys Ala Ile Val His Gln Thr Asp Asn Val Ile
                260                 265                 270 gat cag tta aaa aaa gaa aac gat cat tat caa ctt caa gtaagaatta     12533
Asp Gln Leu Lys Lys Glu Asn Asp His Tyr Gln Leu Gln
                275                 280 cttttagaat aacttattta ttcagacttc atattatctc attactattt atttgacact   12593
agaaagtact ttttctagga tgtgaatttt tgtctgtctt tttaatagtg taatatcttg   12653
tcatgttggt atatttgtcc atatgtgttt ctccaatcac ctcacaaaca ctaattttg    12713 caatttagga tatataaatg atacttgaat gaatgtgtag atagcagtca ttatgggggt   12773
ttctataaaa gactactgaa atcctgtgg atcataacat ttcattttat cttaaaataa    12833
atacattata aatgtattag aaaccaatac attgttcagt atttatgtgg attaaatttg   12893
tttaaaaggt agaataatgt ttaaaaataa aattttctag taatgaaaga taattatgca   12953
attataagat gcagaaacta ttaaatgtca cctataattc caggatgact tcaatgataa   13013
atacacatat gtaatgtaat gtatccgtat gtatgtgtat ataagtatga atacgtatgt   13073
gtgtgtatgt agatatattt atatatataa tgtatatgta aatatgcaca ggtgtaaata   13133
tatgttacat cagtttgcaa caactcttga ataactttg tcttttag gtg cag gag     13190
                                                     Val Gln Glu
                                                             285 ctt aca gat ctt ctg aaa tca aaa aat gaa gaa gat gat cca att atg    13238
Leu Thr Asp Leu Leu Lys Ser Lys Asn Glu Glu Asp Asp Pro Ile Met
        290                 295                 300 gta gct gtc aat gca aaa gta gaa gaa tgg aag gtatttttt tcaattgaca   13291
Val Ala Val Asn Ala Lys Val Glu Glu Trp Lys
        305                 310 taataacttt ttcttttgt atttagatt taaattttag tcttattttt ctttaaatgt    13351
cttatactgg tttataacac gtttattagg gttttaaaac ataagtttat tttatttatt   13411
ggttagaaaa gctctagaac tgtccttttt gatctctagc taatttgtta ttgaatgacc   13471
tctttcacat caatgagttt aactttaaac tttttgatag aagtctaact ccaaaatata   13531
tttggcatct aaaatatata attcgaaata taatttaaat tttttactt aactcatagt    13591 taccttatat acattagtta aatagttgca ggtttaattt tagttttct aactaaatgt    13651 caggttcatc agtgggaatg ggaataagca aagggatcag aataacttgg gaagcctttt   13711
caaaatacac ttttcttcct caccaccact ctccaacctt aaccaaattg tcaggcctta   13771
ccatattaga agctgggatt atgatggttg tatacttgaa aaacatcaga gattattctg   13831
aatgaataat tctaatttta aaaactatca cttctagagt cattgctttc tagtatggtt   13891
cacataaatc ttgtgggcag tttgaactg gttagcatct agggagctca gataacctat    13951
attttaaaca aaagcattag caatggaaat aaggcctata gaatcagtca tgtctccata   14011
aactttatat aaagggccag acagtgaata ttttagacca cctggtctct gctataacta   14071
```

-continued

```
aactctgctt atagcatgaa agcagccatt gacaatacgt aaatgagtga gcaaggtggt   14131
tttccggtaa aatttatttt acaaaagcag atgggaggcc agatttgacc tttgggccat   14191
agtctaccaa cccctggaaa aaacagttgt ctttaccaga ttgaatgttg gcagggtaaa   14251
tggtgacatg ttatatgtat tctgtacttt gttttgactt aataccattt cataattatt   14311
ttatatcagt acgtatagta ttgctgttct ttttaaaggc tatgtaattt ttcttttat    14371
acaggtgtta atttgataat ttgtgaagtt tatgaagttt ccaattttgg ggttgtaaac   14431
tgttttaatg aatatcctta tatatgttat tttgcaaatg tacaagtata tctgtggaat   14491
aaattgctgc aagtgttgta attgtcatgt atgttgcaaa tacattctaa cagtttgtca   14551
cttttttgc tttatggcat tttttgctgt gaaatatttc tttttatgct tagttaaatt    14611
tattatttt taatgacttt tgacattgt tataatgaga aaggcttctg agtataaact     14671
tgttttctca tctttctcc taatatcttg ttttgttttt gttttgttt ttgttttga      14731
gacagagtct cactcagttg cttaggctgg agtgcaatgg tacaatctca gctcactgca   14791
aatgccacct cctgggttca ggtggttctt gtgcctcagc ctcctgagta gctgggatta   14851
caggcatgtg ccgccatgcg cagctaattt ttgtagttt agtagacatg gggtcacact    14911
gtgttggcca ggctggtctt gaaccccctgg cctcaagtga tcctcctgcc tgggcctccc  14971
aaagtgctgg aattacaggt gtgactctgc ctggccttt tttacattta aatcttcgaa    15031
acatataatt cattttgatg taaggagtat catgtggatt caacagagct actctgttgt   15091
ccaaacatct tttattgatt atttcatctt ttattgaatt gattgatcta ttttctagca   15151
gtgtatactt gttttaattt gtgtatgttt taatatctaa aaacgttatt attttctgc    15211
ttttagactt ctttatgaat atttttaatg tgaattatag aactggcttg tccagttctt   15271
aaaaaatatc ttgtggattt ttattgggta tgtgttaaag ttataaattg ttttatagat   15331
tgatttagga taaaccttt tatgttattt ggtccttcta gctaaagaac acaagatacc    15391
ttttctttca ttcattcaag atattttatg cctcttggtt gcattttaat gcatacttca   15451
taaagatcaa ttgtataaaa cttttcacag ttgtatggaa gtacttcttg tttataaatg   15511
agttttgaaa ggttgaaata ttttttaaga ttgaattata aaaaaagaaa attcggtata   15571
tattttaaaa tcattttcta tttgaatttc aggttgtata tacaaaagga acagagatta   15631
tgccagtagt tgctcatact ttctcatttc aaataatttt tattttctgt atcataaatc   15691
tactaacggt gtttattatt tatgataatg aagaatgttt tattaacttt ccttttgcat   15751
aacagattct attgtgttta tttctag cta att ttg tct tct aaa gat gat gaa   15805
                                Leu Ile Leu Ser Ser Lys Asp Asp Glu
                                            315                 320
att att gag tat cag caa atg tta cat aac cta agg gag aaa ctt aag    15853
Ile Ile Glu Tyr Gln Gln Met Leu His Asn Leu Arg Glu Lys Leu Lys
    325                 330                 335
aat gct cag ctt gat gct gat aaa agt aat gtt atg gct cta cag cag   15901
Asn Ala Gln Leu Asp Ala Asp Lys Ser Asn Val Met Ala Leu Gln Gln
340                 345                 350                 355
gtaaaatctt aacagaattt tgtttatcaa ccagttttat tacagttgga actctgaacg   15961
atgtctttta tttattatat catcagtgcc tagtgtagcg gctggtacta ccaagtgtat   16021
aataatgtct tttgaaattt cttctaccac ctggtcccaa taaaaaatta gaattaagtt   16081
tagatcacgg attagactta gaactagagt tactgtgttt atttttctat gtttatgtgg   16141
atagtacaca cattgttttg gttagaaatt atttaacaag aaatgattaa aaactttag    16201
aaatttaaaa taatttttata ctcttttaag gtttatttta ctgtatctta gtcctaacat  16261
```

```
accctataca atgtgaaata agctaaaagc atggttataa tttgactgtg ctacctattt    16321 tattttttagt gaaaataacc caaataaaag gaagtaatac ttttattatt tgtgctgtag    16381
ttatagtcca caagtaagaa gatgatttga aaagtgtatg ctgaataaga acaattacag    16441
gggacaacat tttttaataa agtacgaaag gggaaaaagc taagttgaat aaaagagaaa    16501
gcacagagca aaacagaaac atacaaaatg gtaaaaggt ggaattgaat ggaggatgag      16561
gaaagtaaca tataaggaag tatagaagcc ataaacatta gggagttctg gaaatccctat   16621 tttccagagt gttagccatt atatccatct ttcagtattg gagtaacagc agtgtaccta    16681
tcattgtgta ttacagttga agtgtacaaa atggtaaaag gcatacttgt acccacaaga    16741
aaatatgttc tacagtcttg ttgaaaaaaa tcagacgtac tttttttcctt accttttttag  16801 gttaatattc atgaagggat atatattgtt ttaaaatatt ttatag ggt ata cag       16856
                                                  Gly Ile Gln gaa cga gac agt caa att aag atg ctc acc gaa caa gta gaa caa tat      16904
Glu Arg Asp Ser Gln Ile Lys Met Leu Thr Glu Gln Val Glu Gln Tyr
    360                 365                 370 aca aaa gaa atg gaa aag aat act tgt att att gaa gat ttg aaa aat      16952
Thr Lys Glu Met Glu Lys Asn Thr Cys Ile Ile Glu Asp Leu Lys Asn
375                 380                 385                 390 gag ctc caa aga aac aaa g gtatttttat aaatatatag ttattttata           17001
Glu Leu Gln Arg Asn Lys
                395 tacaattatg ttttttaacga ctttattttt attaaaataa aatgtcaagt caatattgag   17061 ttttctccat ttgaatttta tattttcaaa aaattgtaca agatatttat tattatactt    17121 atattactag tgcttacatt tgtaaatgat ggatgcattt tctattattt ttctcctctg    17181 gtgaaaatta cattaacgtt tattaccagg tcactggtat gaaagaaatg aaaaattgtg    17241 atacaattat ttttatttaa cttttttataa ttaacaaaga atggaagata ataaaatttt   17301 gaccagtgta acagcattgc agatagtttt cagaggtaat ttcacattaa tcttacccaa    17361 attaatgttt catcatattc tccttaccct gagccatatt acctttttta acacatcaaa    17421 ttctatgaat ataagttctt acaatatctg tgttgttata tttccatagc actacatact    17481 atagttatgc cagggcacac tagtgcgaac tgttcatggg aaattcatgg acatgtttat    17541 tataattggt gactatgtat atatgtatac actacatttta tacacacgcg catggaatca   17601 ctatttcttc ttcatgtcat atatatatac atatatacac atatatatac atgtcatatg    17661 tgtgtgtgta tatatatata tttgtatata tgacatgaag aagaaatagt gattccgtgc    17721 acatatgtgt gtgtaagtgt agtgatgtgt ttgcaggtac ggttgtaatt tcaaaaatga    17781 agcaaaagcc ttgctcagga gataattgaa ccaatactta aaggaagtaa aggagtgaaa    17841 catgcagatg gctctaagca gtgggaataa gttcaaaggc agtaaagcag gagtgtacca    17901 atcatgtctg agaacaacaa agaagtctttt ttggctggag tagagtcagc aagtgaggca   17961 gtgataagac cagagaggta aacagaggcc atatcatatg gggccttata gttcattgtg    18021 cagacttggc ttttaagtga gaagggacac cggggaaagt ttctgaagat agaaatgata    18081 taatttgact taggctgtgt ttgcagtaga ctgtaggagt ggtaaataag aatcaggag     18141 acctgttaga agactattgc aataatctgg agaaaagtga tggtggtttg gggcatggtg    18201 gtagcagtgg agttactgga tgcagcagtt ctggatgtat tttgaaagtg ataaaaatgg    18261 aatttgctaa cagatcagat gtaggatgtg agagagagag aactcttggt ctgaaccaaa    18321 agttttggtc atggtggggt tgtgggaaga gcaggttgag agataatcag gtacttaatt    18381
```

```
ttagacatgt taggtttgag atgcttatta gacattcaag tgaaggtgtt aagtaggcac    18441
ttgtatataa aagtttaagg tttaggacaa caatctaggc taaagatatg tttggtaact    18501
gtctctgtaa aagtaattga ataatgaggc tggctaaga tcaccaaggg agtaaatgta     18561
ggttaagaag aaaaatctaa agagcttcta ctttagcagc tggggagata aaaaggagct    18621
accaaaggag actgaaaagg aaagcccaga gagctaggag gaaaagcagg agtatggaga   18681
gccctgaaaa ccacatgagg aatgtaacca aggaagaaga aacaactgct ttcagagctg    18741
tgttcattgc tgctgatagg tcaagatgat cactaaaagt tgactattgg acttagcaat    18801
ggtcattttt ggttcaagag aaaatgggta gagaggaaat gtaataaaga aatataggaa    18861
cccttttcca ggactgtttc tataaagaga aggagaaaac aaggtggtag cttgagggga    18921
aagagggatt aagaaaacat ttttctcttt aagatggaag aaataactca tgattttagg    18981
ttaataggag agctccatta aagaagaaac attaatgaat caatgaagtg gagagagaga    19041
acttctggaa caataatatt tttaagaatg caatgggatg ggatcctagt gtgccagtga    19101
agaggttggc cttaactagg aacacagagt tcatccata ttgtagaaaa gaaggtagag      19161
tgtatagata tcgatgtagg tggcttggta gacatcctgg taatgggaat ttgtggaagt    19221
tctaaactgg ttgctgcttt tttctcagtg aacaagggag caaggttctt agctgaaggt   19281
gaggatagga gaagatgttt cataagtttg aggagaaaga agagaagtga agtataaaa     19341 tggtcatctg aaagattgaa gacgtggaga atgtggtatg actgttgagt aacttcaaga    19401
gcccacgata tatatatgta tttctattta tgtgtttatt atatttgtat cagaacactt    19461
tgaaagtagt ttaaactgct ttaaaaggat gactaatagt atggattgtg cgtattctaa    19521
ttactaggag aaaaagtggc aattgatctc tgctgtcaaa taaggaaaag gacttatctg    19581
ataacacttt agtcagtccg tagttatata atccctaaag ctcacagaag gtgtgtgtac    19641
tagactgtac tctacatctt gaacttaact tgtaaaacgt aatggctaat ggtattcttc    19701
cttcataaga ttaggattag gtttagttat caggaacaga gagctgaaga ataatggcaa    19761
aatcaagata gacatttatt tctcatctat gtaatggcct agaattaagc attccagggt    19821
gttgccttca tctgccccat ccaaaatgga tggaatgcag cttatctca tgtctgtgtc      19881 ccaaacagca agacagagga agaggggcaa gagttaaaag catgtgctga aggataggca    19941
ggtaaatata gtgtttattg tgtagggcca tgtggaagaa tgataggaga atagatatgt    20001
ggatggaagg gagaatagat actggggac aactcagcct gtgtcatgtt ccacagctta     20061
gatgttagct ccagacagct gtgctcattt cttaaaaact tttgtgatct caaacgtact    20121
agttttatgc ctaagtccaa tattaaatat ataacctata tattagtaaa tgcttataat    20181
gaatgagtgt gagaatgatc tgtcaatcaa ttttggaatg atagcaatat tatgttttgg    20241
tcttttaaca atttagtaag atattacaag taggcattta ggaagttttt agcttagttt    20301
ggattaaatt tagctgcaag tgacagaaaa atcaagcata atacaataat ttaaacaaga    20361
tagaaattta tttctctata atatagacaa agttgaagca actagggcag gatttgtgtg    20421
acagatgctc aaatatcccc tatcaggaac cctgtctctt gttgctgtgc ctatctcaac    20481
atgtggtttc taactcatgt gaagttgcca ccctcatatc catgtggatt tcagctagca    20541
ggaaggagga aagagaagag agattactcc tttattttaa aaacattttt ttttttttt     20601 ttgaaattca catatgaact ttgcgtttat attccattac tgacatgacc acacatagct    20661
gcttgtgtgt aagtggaaat ttagttcttt atttcaaatg ccacgtgtc aagctaaaaa     20721 tccatagttt tagtacagtg gacaaaaggg aggttaaata ttaggaacag ctagcagtct    20781
```

```
gtatcacaat gatcattttt tgtaaagcag tattttgcaa ccttttaaaa tccatacccc    20841
ttcagctaag aaggttttac tgaacttcag ttttttagta aattgtatta gtaaaaccaa    20901
aacaaaactt tcatcttaca aatataaaat gacaactttta aaggattttt ttttaatggc   20961 ataccactttt tcttgccacc atgttgggat cactgatttg aaggaataag tagtcaattc   21021
aattcatgat ttttgttttt actctgtag gt gct tca acc ctt tct caa cag       21073
                                  Gly Ala Ser Thr Leu Ser Gln Gln
                                                  400 act cat atg aaa att cag tca acg tta gac att tta aaa gag aaa act      21121
Thr His Met Lys Ile Gln Ser Thr Leu Asp Ile Leu Lys Glu Lys Thr
405                 410                 415                 420 aaa gag gct gag aga aca gct gaa ctg gct gag gct gat gct agg gaa      21169
Lys Glu Ala Glu Arg Thr Ala Glu Leu Ala Glu Ala Asp Ala Arg Glu
                425                 430                 435 aag gat aaa gaa tta gtt gag gct ctg aag agg tta aaa gat tat gaa      21217
Lys Asp Lys Glu Leu Val Glu Ala Leu Lys Arg Leu Lys Asp Tyr Glu
            440                 445                 450 tcg gtatgtattt ttatcttgtc attcaaggag cttagaatta ttcttgccat           21270
Ser tcacagacta ttctgtgcta tttactgcat accatttaaa aaacattcca taagtatctt    21330
ttgataaaga ttatcctcat taatttatac taaaactattg aaacctttga gcatttactt   21390
tttgccagaa ttgttttcaa acttttgatc acagtgattt gtccaaataa tcagttttgg    21450
tgaagcagca ggattacttt ttttattat ctgtgttcat tgggccacca tgtagatgtg     21510
acaccactgg ccaatttgac agaatttatg acaggaacat actgtgtcaa tacaacctgc    21570
tctccacttt ttatactttt tcattggtta caactaattc aagcaactaa tgacttactt    21630
attctactgg tattgctgat ttgctttttac taattctttt agtatttttgg taagtgtttt  21690 ttatatgtaa tgcatattca gagtcacttt gcctttagga tattatactg gaaagtttta   21750
actgttgcat attacatcat tattattact ggatttggtt tataaaagca caataaaaaa    21810
ccagtgtaat gatataaatt ataggcatat gtacattttc ctttagactt agtaaaaaaa   21870
aaatcatgaa cttgataaat ttattcaagt aaaccatgtt atattttaaa ttaaattgga   21930
tatttttcag gga gta tat ggt tta gaa gat gct gtc gtt gaa ata aag       21979
              Gly Val Tyr Gly Leu Glu Asp Ala Val Val Glu Ile Lys
                  455                 460                 465 aat tgt aaa aac caa att aaa ata aga gat cga gag att gaa ata tta     22027
Asn Cys Lys Asn Gln Ile Lys Ile Arg Asp Arg Glu Ile Glu Ile Leu
                470                 475                 480 aca aag gaa atc aat aaa ctt gaa ttg aag atc agt gat ttc ctt gat     22075
Thr Lys Glu Ile Asn Lys Leu Glu Leu Lys Ile Ser Asp Phe Leu Asp
485                 490                 495 gaa aat gag gca ctt aga gag cgt gtg g gtaagccatg ttttaagtta          22123
Glu Asn Glu Ala Leu Arg Glu Arg Val
500                 505 catagtttgc gcaacctgat ttacaagtct ttttttttaa tttaaattttt gtttattatt   22183 atttattaag tagtttaatg ctttttttcaa atgcttttat aaaacattta atacaaataa   22243
aagtggagct aacctgattg aagtggaatc agatttatg gggttggagt ggtgggtggg     22303
cagggctgga acattgcttt atttggtcta gcatctcctc agtaatagct gcttgtttaa    22363
aaagatgaaa gttattaat accacatatc agagattaac cttttttttt cccaacaaaa    22423
gtagggtctg tattacccat gtttgtttgc aaaatgctct tgtaacagat gagatattta   22483
aacttcttgc tctgtgttgt gattctcctg cctctgcctc ctgagtagct gggattacag   22543
```

```
gtgtgcacca ctatgcccgg ctaattttg tattttggt agagatggga tttcaccatg    22603
ttggctaggc tggtctccaa ctcctgacct taagtgatcc acccgccttg gcctcccaaa    22663
gtgctgggat aataggcatg agccaccgcg cctggcctgt taaaatcttt taaagatttt    22723
taagtacttg atttttataa tttagactac ttacgtttta ctttgttcga gtatttaag    22783 gagtaattag taatatagct tgagagttta tatttatt ttaataaata gcctattagt    22843
taatattact aatttgagtg ttatgatagt gcagactaag ttgctgcttt aaaatgaaaa    22903
taaatatcta aatatcaatt tcattattgc taaatttcat ttaatgcttt cttagttaaa    22963
aatgatcatt tgtaaaaact attatctaaa gaaaagacaa atagacaaat aagtatttta    23023
tacagatata tatgtgtgaa aagtatctaa cttggatccg tagttgtgct aggaccccaa    23083
attagacttc tgatcaactt ggactatcag atcacagcct tctgatcaac ttggactatc    23143
agatcacagc caagaatctg gaagttccta agatgactt ctggcccgtc taggtagctg    23203
tcatagacat catattttct gtgcttaaaa agctccaaat cttggtttat aatttcattt    23263 aggttttgt taggatttcc attaataatt gtgataaaat tttaacttgg gttacagttt    23323
aaatatctgg aaaattcttt cacagaaagt tacctcattc ttcagtgata ctggctaagt    23383
gaattataac cagttgcttg atggtatatg acatttttgc agcttattg aatgttttta    23443 agttttaat tatattgctt tctattagg gc ctt gaa cca aag aca atg att       23496
                                   Gly Leu Glu Pro Lys Thr Met Ile
                                            510                 515 gat tta act gaa ttt aga aat agc aaa cac tta aaa cag cag cag tac    23544
Asp Leu Thr Glu Phe Arg Asn Ser Lys His Leu Lys Gln Gln Gln Tyr
        520                 525                 530 aga gct gaa aac cag att ctt ttg aaa gag gcaagtgtgg tagtcagttg       23594
Arg Ala Glu Asn Gln Ile Leu Leu Lys Glu
    535                 540 attattttct tggctgaact atagagaaat actaataatt tatactttgc ag att gaa  23652
                                                           Ile Glu agt cta gag gaa gaa cga ctt gat ctg aaa aaa aaa att cgt caa atg    23700
Ser Leu Glu Glu Glu Arg Leu Asp Leu Lys Lys Lys Ile Arg Gln Met
545                 550                 555 gct caa gaa aga gga aaa aga agt gca act tca g gtatactcag            23744
Ala Gln Glu Arg Gly Lys Arg Ser Ala Thr Ser
560                 565                 570 ttattctaaa cctttaaaaa gaattattga taagtgagtt gtctggatat gaaattattt    23804
gtgtcttagc tgttttttgct gttctattgt ggatctgcta caaatttaat aaatgacaat    23864
aataacctga aggagataag tgagtgtcag tgggttcagt cctgaatctg aaatagacaa    23924
aaacaaaaca aaacaaaata acaaaaacca agcaaacaaa aagaaaaaa accttagaat    23984 tatggaattt ttgaaaagtt ttatagtata gtatttaat ttctagacag caccaatatg    24044
ttgttattaa taataataaa acttagtagt ttttatgtta atatatgtta ctcaacattt    24104
tcccttccct taaggactat gcattgaaaa gcttttcttg taagttatta ttattattat    24164
tattattaat atttgagatg gagtctgtct tgttctattg cccaggctgg agtgcactgg    24224
tgcgatcttg ctcattgcaa cctccgcctc ccgggttcta gtgattcttg tgcttcagcc    24284
tcctgagtag ttgagactac aggcgtgagc caccacgcct gacttatttt tgtattttta    24344
gtagaaacag ggtttcacca tgttggccca ggctggtctt gaactcctga cctcaagtga    24404
tccatccact ttggctcccc aaagtgctgg aattataggc gtgagccacc atgcctggcc    24464
ttaaattatt cttttctaag tgaaagtaat gttttattga atataaatta acatctttct    24524
```

```
tgggtttatt ttacttgagc taaagagaac agttggttaa gttttataat agccattgca   24584 gtgcttttt gtaagaagac cacacagaag gactgtcttt ttcacttgcc ccaaatcccc    24644
aagcacgtat atgagtaata gcagagtggt tcttttagc attatgattt ctataataca    24704
tccaaaactt tctcaagaaa aaacttcatg atttattagt acaataatca gtttactcat   24764
tactcatcat ttatatttac tttatatgtc ttttaactgg tgcttattaa gtagcacttt   24824
aatatagaat aggcaaagaa tggtagagaa gatgaaattc aaaaattagg ttctcacatt   24884
attaatagtt cattaaaagt gagctaaatg agaagcttgt attggctatg tagaattttg   24944
gagggatttt ggaaacaatt attctacctt tgcattaaaa cttgattgta ggttttaaga   25004
attaaagtgt tggaatagta ggagggttat tttaatgttt ttagtttgtt aattctctta   25064 tatatag ga     tta acc act gag gac ctg aac cta act gaa aac att tct   25112
        Gly   Leu Thr Thr Glu Asp Leu Asn Leu Thr Glu Asn Ile Ser
              575                     580 caa gga gat aga ata agt gaa aga aaa ttg gat tta ttg agc ctc aaa     25160
Gln Gly Asp Arg Ile Ser Glu Arg Lys Leu Asp Leu Leu Ser Leu Lys
585             590                 595                 600 aat atg agt gaa gca caa tca aag gtaatagtaa agtattgcaa agagagtaaa    25214
Asn Met Ser Glu Ala Gln Ser Lys
                605 ggaaaatatt ttttttttt ttttttttg agacggagtc tcgctctgtc tcccaggctg     25274 gagtgcagtg gcgcgatctc ggctcactgc aagctccgcc tcccgggttc atgccattct   25334 cctgcctcag cctcccaagt agctgggact acaggcgccc gccaccacgc ccggctaatt   25394 ttttgtattt ttagtagaga cggggtttca ccgttttagc cgggatggtc tcgatcttct   25454 gacctcgtga tccgcccgcc tcggcctccc aaagtgctgg gattacaggc gtgagccacc   25514 gcgcccggcc aggaaaatat ttttattgtg tttcatttc ttcccccttt atctcattct    25574 tgaacatcta atcttattat tgttgttaaa taagtagagg gaaatatttg cttatttaac   25634 ctgttgattc aaagattgat taatgagaca ttatttactc tgaatacaga ttaggagttc   25694 agataaagca gagctgctgc ataggagatc atcattcaat accccacagt cagatcagaa   25754 tgagacagaa gagaatatga ccataggatc attatcaaga atgttatctg aaattcacca   25814 tagtgtagaa agtggaatgc atccttttgt cccttttaact agactttctt catccatgca  25874 agttaaagag aattcaactc cagaaactat tacaataaga gagattttta aagcaccatg   25934 tctgcagtct tcaagaaatc tagaatcgtt agtcagcacc tttagtaggg aaagccatga   25994 agaaataaat gacatatgcc ttttttctga tgactgtatg aagaaggtgt caagaagcca   26054 tcaagcacta gagaagacta gttttgtaca aaaaagcaat tcatctttc atggcttatc    26114 aacagcttca gacataatgc agaagttatc acttaggcaa aaatctgcaa tatttttgtca  26174 acaaattcat gaaaatagag ctgacatgga taaatcacaa gtagcaacat tagaagaaga   26234 acaggttcat tcccaagtaa agtatgctga tatcaatttg aaagaagata taataaaaag    26294 tgaagtaccc ttacagacag agatattgaa aaataagctt aaggttaatc ttccagaccc   26354 tgtgtctatt actgcacaat caaaattatc tcagataaat tctcttgaaa atcttataga   26414 acagttacgg agagagctag tatttcttag atctcaggtg agttttctc caaattatat    26474 ttctgtggtt gttctttat gacgtctcta acaaagttct gtaacaatta tagttagaat    26534 atttttgttt gcacttaac atcagttata cacattgtac ttttaaaaat ctaaatgca     26594 gtacattgat atgaactcat tgacttgtct aattattaa atttttcttt agaatgaaat    26654 catagcacag gaattcttga tcaaagaagc agagtgtaga aatgcagata tagagcttga   26714
```

```
acatcacaga agccaggcag aacaggtagt gtaaaggcag aacattaaaa gagatgattg    26774
tggtactaaa gacaaaaacc gttatatctt tttgcctctt accatggatg ttgggagagg    26834
gagaaagtgg gattaagatc accatctgct ttactgttta gattttagtt tattttatg     26894 attgctgcta tgtcttcata gctcgttttt tttgttttgt tttgttatac ttaattgatc    26954
aaacttttct taacttgaaa attatagact tgtgatattt tgttgaaaaa aatcaatttt    27014
attctctctg ctttttttcag aat gaa ttt ctt tca aga gaa cta att gaa aaa   27067
                         Asn Glu Phe Leu Ser Arg Glu Leu Ile Glu Lys
                                 610                 615 gaa aga gat tta gaa agg agt agg aca gtg ata gcc aaa ttt cag aat      27115
Glu Arg Asp Leu Glu Arg Ser Arg Thr Val Ile Ala Lys Phe Gln Asn
620             625                 630                 635 aaa t gtaagttaca attatctttt acttttctgt tcttattttt cctatactta         27169
Lys aaatcatggg cctaaaaggg cgttaacaca ttctctgttt tctaatctgc tttactccta    27229
attacctctg tactgtatat acttcagtct gtcactatcc agttgatttg ccttgctgtt    27289
ttcattgtga gagaatgtta ctaatatgaa ttttttgtga aatatataa ctccttttc      27349 tgtgtgttc ttcaatcaaa atgaagttag aacaccaaat ttaaatact ttaatataa       27409 gcatagttta agtaaggca gaagtatgcc ttatatacgt gtgtatatgc acgtgatata    27469
aataggtctg tcatttaact caactattca cgttggattt atagttgaat tttttgtat    27529 gtttatttac atttggattt ttccaatgat gtctttggta tatgtgaaat atttgtcatc   27589
tgtatagcat agtgtaaatt gtgaaaaaga tctgatcatc caatgagaaa actgtgtaat   27649 tacag ta  aaa gaa tta gtt gaa gaa aat aag caa ctt gaa gaa ggt atg    27698
          Leu Lys Glu Leu Val Glu Glu Asn Lys Gln Leu Glu Glu Gly Met
              640                 645                 650 aaa gaa ata ttg caa gca att aag gaa atg cag aaa gat cct gat gtt      27746
Lys Glu Ile Leu Gln Ala Ile Lys Glu Met Gln Lys Asp Pro Asp Val
    655                 660                 665 aaa gga gga gaa aca tct cta att atc cct agc ctt gaa aga cta gtt      27794
Lys Gly Gly Glu Thr Ser Leu Ile Ile Pro Ser Leu Glu Arg Leu Val
670                 675                 680 aat gtaagttatt ttttcatgt taatgttttt cccctatcac tttagagaga            27847
Asn ttttctgctg tgtacagatc tccatagttt ctgatgagat attttagtc atttgaatca     27907 tgtttccct gtatgtaaag tgtagttttt cttgagctgc tttcaatact tttcttctac     27967
caattggata attgttatta atctgtcttc aagttcactg acatttcct ctttatctgt     28027 gttctttgg ttcaagggtc agcttgagac cttgaggagt ttttacacc gactttggag      28087 ctcgttttg ctgactcttt tcttattggg attttccttt cacttatccc atggctttgg    28147
gctgtatcct gtggttttct agatgagaaa gatgatagat ctctgcaatt gcaccctgcc   28207
ctatgactaa atcttaaaa atggcaaagt caatctttgc tggtcctgtc ttccgtattt    28267
gagggttttt ttcccaaaat ctgcttgctt ttgttcattt tctagaacat ctaggtagtt    28327 tttttcatt catttttat ttatgggagt gtagatctct taggaactta tgccatcaga     28387
agtattatga aatggcttta ttctaaatgt ttaaagattt actcattgct acaagaaaga   28447
tttagccatc actaatattc tatatatatt taccatatag ggacttgaga atttcacagg   28507
attcagtatc tgtatataaa cttgaataat atacacattt tagattgtta atatttaagt   28567
atatgtcatt tatgttatct gaacatattt agcgtacatt gtcatattat ttcccaaatt   28627
tgtgcttgat ttcaaatggg aaaaaaattc ttattattta ttgaattgtt tttttaaaaa   28687
```

```
aatcatgatt aatcagtaat tggatacttt ttaaaataac actataattg ttaacagaga   28747
atgagagtga tactggtatg ttaaaaactt cctgaggcaa gaaaataatt tgattcccat   28807
tatatctttc tcatactgac tttccttctc tgattggtga ttttgttttg cctctgccac   28867
tttgaatgtc taaaatgatt ctttatgctt tttttatgtg aacatctttt gtccgtgatg   28927
atgcccacta ctgatactgt gtcccagatc aaacttaatt ttccaagggc agctctactt   28987
agtgaccaaa tgaaaacaca gtgaatagcc caagaaatcc taacttctat ttatgttgac   29047
aatctctgga ccttcctgaa gccactgttt gcatagactt catttactt tatccgggat    29107 tgtcattgtt ttttcagatt cataggccct atctgaaatt cacaaatcac ctagcaatac   29167
ttctctaaga aatcttcaga atccatgaca atttagacca gacaatgctg gattatgcac   29227
ttcagttcac ttttgttac tacaaggtat ttttcagtgc ccccaacagc tatcttaact    29287
cattctcatt ttaccaaagt ccatgtagac acggcactat tcctcaatga gacaactaac   29347
tagaccacct tgttgtcagt cagagtacct tcctctacct acttttatct tccttatatc   29407
ctctttgagt tagtataagt tattactctg catgacctgc tctaatctcc ttcagggaa    29467 ggcttttaca aatctactac ctagagttaa acccccagatc accttcctga gtaggagatt  29527
gcatttggtt ctattcattt taccttattt ggcttctacc ttcactttt aagacttact    29587 ttgcctttaa cagttttttc catacagttc atctaaagtc caaatatatt tattagatgt   29647
gtgcattgtg tgtatatact tagatatgcc actgttggag atttcgggcc agtgatgcca   29707
ctctgataat attttaatat ttgacatatt attttgctt actcattatt cttagataat    29767
atcatgttat gataccttgc ctttattttt atttatgctt caactatgtg gagaggaagc   29827
actgaaaaat tcacttaatt gaatgttgta ttgatcaatt gttcaatatt gtattccatt   29887
cctttgcgca tgctttgaat gcaggtgcta tataatttca gagaaaaata cctcattttg   29947
actgtacaaa acccccatgt agggagcaga gctcacattg ttttcccctt ttagagacaa   30007
gaaaactaag atacagagaa tttaagtcac ttgcccagct gttaagtgac tgattaaaat   30067
ttgaaccctg gtcatcttat tcccgtctgg ttgttttct agtctaccag tctattaaga    30127
ttagctaggt gttttttaat tgttttaatg aagtaattac tatgcttggt aatgtaaatg   30187
aaagttttat agattcataa ataagaattt gaattggcat acttttatat catgcttggc   30247
aatgaaaata ggaaaatgct taaatgtcca ttttatttaa agacagactg tttttttacta  30307 tgatttact gttttctcc acatttctaa tatataatat aaatttgcta g gct ata      30364
                                                        Ala Ile
                                                           685 gaa tca aag aat gca gaa gga atc ttt gat gcg agt ctg cat ttg aaa     30412
Glu Ser Lys Asn Ala Glu Gly Ile Phe Asp Ala Ser Leu His Leu Lys
        690                 695                 700 gcc caa gtt gat cag ctt acc gga aga aat gaa gaa tta aga cag gag     30460
Ala Gln Val Asp Gln Leu Thr Gly Arg Asn Glu Glu Leu Arg Gln Glu
    705                 710                 715 ctc agg gaa tct cgg aaa gag gct ata aat tat tca cag cag ttg gca     30508
Leu Arg Glu Ser Arg Lys Glu Ala Ile Asn Tyr Ser Gln Gln Leu Ala
720                 725                 730 aaa gct aat tta aag gtgagaattt tattaaataa aagaaaatgc taaacataag     30563
Lys Ala Asn Leu Lys
735 aatgtagatt taataggaaa tttttaattt tttaaaaga atgctttatg agaaaatgcc    30623 ccttgaatta attcttccaa tattaagaaa ctggatttct cttataaaat tataagtgga   30683 aaataagtgc cttataagat tgaaaagaat acaaaaattc taaatctcat acctaggcat   30743
```

```
ttctaagcag aaactgaagt atggttgagg taaaattcct ggcagggcat tcacatatct    30803
gtcaatttgt ctttcttgg gtgtaagagt tgtgattctc attgctggat ttttttttcc    30863 ag ata gac cat ctt gaa aaa gaa act agt ctt tta cga caa tca gaa      30910
   Ile Asp His Leu Glu Lys Glu Thr Ser Leu Leu Arg Gln Ser Glu
   740             745                 750 gga tca aat gtt gtt ttt aaa gga att gac tta cct gat ggg ata gca     30958
Gly Ser Asn Val Val Phe Lys Gly Ile Asp Leu Pro Asp Gly Ile Ala
755             760                 765                 770 cca tct agt gcc agt atc att aat tct cag aat gaa tat tta ata cat     31006
Pro Ser Ser Ala Ser Ile Ile Asn Ser Gln Asn Glu Tyr Leu Ile His
                775                 780                 785 ttg tta cag gtattgaaaa ttttgttaca ggtattgaaa attttacatg             31055
Leu Leu Gln tgaataacaa aaatcattgg tagtatgttt ctttatgttt ttattttat tttacttat     31115 tttaatttt ccatcaccaa agcatgcaga tagtactttt ctcaatattt agtcttcatg    31175
tattcctgag ttctcaaaat agtaacagtg aaatatattt tttatggatt ttgatgttag   31235
atggattata aataaaagca atttatacca ttcattccat tcatctgcat gagcagcatg   31295
ttcatacatc ttgttcgcac acctgtcatt catgtgaaat atatggttca caagcagaac   31355
aacaagcagc tattataaag cagtgttaag taaatgagca cttttatttc ttgctgggtg   31415
gaaaacaaaa gaataaagtc tgtcaaggct ttttagtgtc atgatagaat tgttcccctt   31475
tttgcattca caagtaaaaa ctacttttt tttgagacag agcctcactc tgtcactcag    31535
gctggagtgc agttgcgcta tcttggctca ctgcaacttc cacctcctga gtttaagtga   31595
ttctcatgcc tcagcctcct gagtagctgg gactacaggc atgcatccct ggctaatttt   31655
tgtatttttt tttagtagag atggtgtgtc gtcatattgg ccaggctggt ctcaaactcc   31715
tggtctcaag tgattcgcct gccttggcct cccaaggtgc tagggttaca gacgtgagcc   31775
actgcacaca gccataagca aaaacttcta aaccaaatta ttcttcatct ttgtcttccc   31835
tttacgcaat aaaatgttaa tctaccacca aagaggaaag ggtactctac tatactacct   31895
gccctgggtt tctcagtttt gctgtctata taatggtcgt tatgaatgtc ctaatgacag   31955
atccttttca ttattttatt tgaaatttga ctatctataa catcacatac attataaata   32015
taattacaaa tatatgttca gaatcaatga aaatatattt ttgattatat gggccactat   32075
ttctctctgc taggtgatcc atttgtgagt atacttgagt tataattatt aagtactcat   32135 ttttatttg gaaattacag taattcatct ttttctcaat attgggatt ttattattat    32195 tttatgttgt ctaaggacag ccttaactac ttattagaat attgctttgt atgtgatatt   32255 attatttta aatgtataat tttaacatta ttatttctct tatttacctg aggtatagga   32315
acactatcag caaatattgg tagtatggca ttgtcgtatt tttgagata aaattcatga    32375 tttttaatct ttgtataaga aatatatcag aagtttgtag tagattagag agtaccaact   32435
gggagtctga aaagctgtcc aaagtggcaa acaggtact tagactctca atcctaaggc    32495
tgtatagagc tataaacgtg gcaagacctt tggagtcaga cagacccaaa ctcaaatgtt   32555
ggatccatgt atatgaaag cacctgacaa caagcctagc atatgtactt ggtaaaaatg    32615
attgccaagt gtagtgttaa tgagtttttg gatattgagt aagttattta aatttcaatt   32675
tcatctttaa aatgaaataa ttggaaagga taatttgagt gagggtatga aattatgtgt   32735
tcataagaga gggtatgtgg ccgagtgact agaggcgagt ttataactat tctatctaat   32795
aaaactttgt aatctggtaa tttgtgtgct aaaaataact ttacctgttg tatagtactc   32855
```

```
tttttttatg ccttaaacta aagtgttcaa aatatcatgg aaaaatgatc tgtgttgctt    32915
acagatttgg tgacttttaa cttcctata atgttgtcag aatatgaatt tatactttca    32975
aattcagcat ttattctatt gtgttttttt ttgcattctt atttctaaac cactttcag     33035
```

| gaa cta gaa aat aaa gaa aaa aag tta aag aat tta gaa gat tct ctt | 33083 |
|---|---|
| Glu Leu Glu Asn Lys Glu Lys Lys Leu Lys Asn Leu Glu Asp Ser Leu | |
| 790             795             800             805 | |

| gaa gat tac aac aga aaa ttt gct gta att cgt cat caa caa agt ttg | 33131 |
|---|---|
| Glu Asp Tyr Asn Arg Lys Phe Ala Val Ile Arg His Gln Gln Ser Leu | |
|         810             815             820 | |

| ttg tat aaa gaa tac cta ag  gtataggtat tagcaaaact ataaatataa | 33181 |
|---|---|
| Leu Tyr Lys Glu Tyr Leu Ser | |
|         825 | |

```
ttgcagtata ttcttgttaa ttgtgaaagt aacgtaagaa taatttatgt tttgttcttc    33241
ccttcttctt cttcctttgc aattgtattt ttttttactc tggtaactac tgttaggaac    33301
ttatttatgg agacagtgta gcttaatgat tacattaagc ctgggattat cctgcctggg    33361
tttgagtcat ttaacgtttg cttttgtaa gagcttgagc aagtcatctt acctatctgt     33421
gtctcagttt ccttatctgt aagttacttt gtaagtaata cccttttcat aggattattg    33481
taaaacgtaa atgaattatt agatgaaaat gctcggacta gtgtgtggca catgaaaca     33541 gtttgtaaat gttagctgtt gttagcatca ttcatcatca tcacaatcat cattgttcat    33601
atatgtttat agggaactaa catatttctc cttatttctg tcatctcatc taaatcaata    33661
gaatgatttc cttaatagga attagaatac ctaatcaaag gtgatttaaa cactaagaat    33721
aattattatc tgacctaacc agaaccacaa agctagttgt agggcaggtc atatttgaag    33781
gttgttgtta tcgcctatga tggttgtaaa atagctgcat gaattcaaga aagatgatgt    33841
gcccattgaa gaagaggagc atttttttct acatagcttt tattttttaaa taaacatttt    33901 tttctggtga tacctggcag acattgactc cgatctcatt tgctagaatt ggatcacatg    33961
tccaagtctg aaccattcag ttgcaaagag aatgataccg ctatactggg tttatgccaa    34021
gaacattaca catgtttgtg gaatgctcat gtgtagacaa cagtgtctta cacaacttca    34081
aaaaaataat ttatatataa atatgtttta aattactttt taaattcaca agaatttatg    34141
gtatacaaca tggtgttcta tatgtgtata tactatgcta tacaacatgg tgttctatat    34201
atgtatatac tatgctatac aacatggtgt tctatatatg tatatactgt ggaatggcta    34261
aatcaagcta cttaacatat gtattaccte gcatactttt tttttttttt ccttgagaca    34321
gagtcttgct ctgtcaccca ggctggagtg cagtggcgct atcttggctc actgcaacct    34381
ctgcctcctg gtccaagtt attttcttgc ctcagcctcc caagtagctg agattacagg      34441
catgtgccac cacgcctggc taattttgt attttggta aagacggagt tttgccatat        34501
tgtccacgct agtctcaaaa ttcctagcct caagcaatct gcccaccttg gcctcccaaa    34561
gtgctgggat tacagcatac ttcttcttat tttttttttt ttttgcacta agaacactta    34621
aaatttactc tcttagcaat tttaaagtat ataatatact gttattaact tggtcacta       34681 tttaattag acttaagatg tgtttgtatt caaattattt tgtaagcatt taacacccaa       34741
atttgagagt ggggtcagaa tgttggaatt tgatttctag aattagtata gggtattatt    34801
ttcctacttt ttttctgtgt tcaataaaat gtttataaga ttcagcttca attatattat    34861
aacccattta gtggtgaatc agggaagaat gaaaataatt tgataacttt gttgccttgc    34921
atttatttaa aaaattttta attctaggct aaacccttttt taaatgaaag tttaacttct    34981
```

```
tgtgttttca gatactgaat agctatgata cctcttgtgt tgagaaaact ttaaatttgc    35041
ataatctgaa gttatctttt cttataaaca ttttattagg tttacagtat tgtcttttg     35101 ttttgttttg tttttag t gaa aag gag acc tgg aaa aca gaa tct aaa aca     35152
              Glu Lys Glu Thr Trp Lys Thr Glu Ser Lys Thr
                  830             835 ata aaa gag gaa aag aga aaa ctt gag gat caa gtc caa caa gat gct     35200
Ile Lys Glu Glu Lys Arg Lys Leu Glu Asp Gln Val Gln Gln Asp Ala
840             845                 850                 855 ata aaa gta aaa gaa tat aat gtaagtaaaa catttttaac attagtatgc         35251
Ile Lys Val Lys Glu Tyr Asn
                860 aatattgtac aaagtaggat agctagattc aacaagtaat atggatgtgt ctttgtgcag   35311 aat ttg ctc aat gct ctt cag atg gat tcg gat gaa atg aaa aaa ata     35359
Asn Leu Leu Asn Ala Leu Gln Met Asp Ser Asp Glu Met Lys Lys Ile
        865                 870                 875 ctt gca gaa aat agt agg aaa att act gtt ttg caa gtg aat gaa aaa     35407
Leu Ala Glu Asn Ser Arg Lys Ile Thr Val Leu Gln Val Asn Glu Lys
    880                 885                 890 tca ctt ata agg caa tat aca acc tta gta gaa ttg gag cga caa ctt     35455
Ser Leu Ile Arg Gln Tyr Thr Thr Leu Val Glu Leu Glu Arg Gln Leu
895                 900                 905                 910 aga aaa gaa aat gag aag caa aag aat gaa ttg ttg tca atg gag gct     35503
Arg Lys Glu Asn Glu Lys Gln Lys Asn Glu Leu Leu Ser Met Glu Ala
            915                 920                 925 gaa gtt tgt gaa aaa att ggg tgt ttg caa aga ttt aag gtacatctga      35552
Glu Val Cys Glu Lys Ile Gly Cys Leu Gln Arg Phe Lys
                930                 935 ttcttatttt gcttttttctg actatgaaaa atttcaaata tgcagaagat aggatggtat  35612
caataatgct catcacctga attaatagtt aacatttatt aacattttgt cataattgct   35672
tcttctgatt tttgtgggat gtttgaattg cagacattcc tcccctaaat atttaatgta   35732
cccttttgaa aaaggctttt ttctttaact aaccatagta actttattat acctaacaaa   35792
atgacagtaa ttttctaata tcgcctaata ccctgattat agtcacattt tttacatttt   35852
ttgatcaaag aataagcatt tggatgttac atctcataaa tcttttttaat atagaatccc  35912 cttggttttc ttttttctcca aaaaatgttt gaagatgtat ctaacttttg tgtgtgtgtc  35972
attttacttg ttcctgtgtc ccttgtatta ctaaaagtta ggtcagaacc ctaagttaca   36032
ttcaggttta acatttttg gcaagaatac ttcataagta gtgttctata ctttatattg    36092
catcacttca agagtatctg gttgttccat gttttgtaat tgattactct gttaaggaaa   36152
agacaagcag accaagtatg gtggctcatg cctataattc caacattttg gaaggcccag   36212
gcaggaaaat ttcctgagcc cagaccagcc taggcaatat agtgagactc cgtctctaca   36272
aaaaatgttt tttttttttgt tgtttgttt ttaattagct tggtgtagtg gcacatgctt   36332
gtaatcccag ctacctggga cattgaggtg ggaggatcgc ttgagcccag aagttgggg    36392 gctgcagtga gctgtgatca tgtgccactg atctccagcc tatgtgcctg tataacagag   36452
cgagtctctc tcttaaaaga aaaaagaag aagaagaaga agaaaagata accatatacc    36512
tccattatta agcaatttag ctaactggtg atatttggt accatacaaa taacaaatta    36572
tttgtcagtc ctaatgattt tagcatctgc tgatgattgt tgcctaaccc aattattaaa   36632
agttgcaaac atcataattt tctagttata ttatgcactt acatttatta acagacatgc   36692
ttttgtaaaa taaatagcgt ttcctcatta gcccaggcta tttgtttatc ttgaagttta   36752
gctcctacta caaaggcaag ataaatgctt ttctctttaa ttaccagttt tcagaataca   36812
```

```
cacttggtgt actctgcact acctgctttt tttgtcccct ccgctttctc tttttttaagt   36872
atcagattag actcacagat ttttaaatat tccatgtgtt ttagttggag tcatattctt   36932
ttgtctcaac tttagccaaa gagagtcctt taaagttgac tcttatattg tcttgacaaa   36992
aattcattag tcttttgaac gaagcctcaa agcttgactt gttttctagc ataagatgtc   37052
ttagacttac ctacatactt catgcccata cttggaataa accatttctt taaagagccc   37112
aggttccttt tagtggggaa ggcatttaga taccaaaaac tggccactgg gcatcattgc   37172
tctcagagta tcattgccac tagtctctca gtagacaagt tagaaaaata tgtatatatt   37232
taaaccatga gttcatattg ttatttccag tttaattata acattatggg gtaagtaaat   37292
agtatcggat ttttactaag cttctttgat tttgcacttg tattttttc ttacatagaa    37352
aacctttatt attaacatta aaatatttgt tttatcctac aatatacata caataatttg   37412
aaaaataata cttgaattga tattaatagt aacaacaaca gcactgctgc caaacatagt   37472
ttaaagttt atttcaggtc ttatttctt cagaatatat cttgctgaga atgtataggc     37532
aaagtattct acacttactt gaaataattg tcttcatgcg gttatgttat acatttgata   37592
tatagttagg ctcatttgtt tttcattttt tttattttag ggattttttt cctttattga   37652
atttaatat atacaatatt tatatatgca aaatatttaa tcagagaaat cttaattctg    37712
gtcttacgcc tttcatatta ttctgctcca ccctctgtag gtaacttatt atctttctca   37772
tgtttccttt ttggaaacat aaacaaagac aagacaggtt acatgacatg tatacccttc   37832
tgcacctagt tttataccct accttgtagt ttattttaa gcatgtaaat gttcaatgtt    37892
catgactaaa tttggacagg atcataggaa cacagaattc aaagtgaaat taaaatgggc   37952
ttgggttctt tactttccac tttaaaggtt gtaatgggtg atgtcaggct aataaaccta   38012
ttttcagctt gatctaaagc ttaatactga gcatcaagaa attctttaat aaatataagt   38072
gatatttatt cagacatgta ataaggaaat gttcatgtct tattttttgtg ttagattttt  38132
ttagaatcta cttttgttag agttttataa atacagttag tgtttgagat agaaagagaa   38192
aagaattagt tttcttcctc ttctacctgc tcatgaactt gattttttc tcccaacaat    38252
tgaagagcca agaaaagggg agattcttaa gagatgggaa atagaatctc atctaccct    38312
gtttccccca gaacagtgaa actgaatctt aagggtaaga tagaatagtg tgtacttaac   38372
ttagatggag aagaaaggct gccaaaatga gatctgaagc gctattacaa atatttccat   38432
cgttactgta cttcagaatg aattacaacc gtaagttttt ttacttcctc attcataaat   38492
ttgattattc cttataccac ttctcagctt tcatcattct ttattgtact tttctatgta   38552
atgtttgcct attatacagc aacttaagag aactgtaagt ttggacattt cattttggtg   38612
ttgataatag aatatctttg aatagttcta tagttgatga gtagaaccat gaaccaagta   38672
acttaaagtc cttgatgtta tttattacag agaactataa tagaagctct cccgctaatg   38732
tttccatcat gtgtacaaaa agttttcttg ttattaaagc tagtccgttt aacttacaat   38792
aagcataaat agctaagctg tgaaagttac ctgtgataat gctaatttt ccatttatta   38852
aaaggcaagt tgttttccga tcataagaaa tttagaaaag ccatccaaag ataaattccg   38912
agtgatatat tcctgctgtt tgttatgttt tctcaaatta attgagtttt attttacaat   38972
gacaggagtt attaaagtat tttatttta ttatgattaa gatttcaaa gtaacatttc    39032
ttatatgaaa gaaattatgt taatgcatgt ttttcttaca tgggaaatca tatatttaa    39092
aaatgatttt aaaattcgtt ttactttaag ttgtattatc tttctcaaaa gtggctagtg   39152
```

```
cttgaccaga aaaaaagaca ccagcataac tcagtgtatc tttatttaca tag gaa          39208
                                                          Glu
                                                          940 atg gcc att ttc aag att gca gct ctc caa aaa gtt gta gat aat agt         39256
Met Ala Ile Phe Lys Ile Ala Ala Leu Gln Lys Val Val Asp Asn Ser
            945                 950                 955 gtt tct ttg tct gaa cta gaa ctg gct aat aaa cag tac aat gaa ctg         39304
Val Ser Leu Ser Glu Leu Glu Leu Ala Asn Lys Gln Tyr Asn Glu Leu
                960                 965                 970 act gct aag tac agg gac atc ttg caa aaa gat aat atg ctt gtt caa         39352
Thr Ala Lys Tyr Arg Asp Ile Leu Gln Lys Asp Asn Met Leu Val Gln
            975                 980                 985 aga aca agt aac ttg gaa cac ctg gag gtaagtttgt gtgattcttg               39399
Arg Thr Ser Asn Leu Glu His Leu Glu
990                 995
```

```
aaccttgtga aattagccat ttttcttcaa tattttgtg tttgggggga tttggcagat        39459
tttaattaaa gtttgcctgc atttatataa atttaacaga gatataatta tccatattat      39519
tcattcagtt tagtttataa tattttgttc ccacataaca cacacacaca cacacaatat      39579
attatctatt tatagtggct gaatgacttc tgaatgatta tctagatcat tctccttagg      39639
tcacttgcat gatttagctg aatcaaacct cttttaacca gacatctaag agaaaagga       39699
gcatgaaaca ggtagaatat tgtaatcaaa ggagggaagc actcattaag tgcccatccc      39759
tttctcttac ccctgtaccc agaacaaact attctcccat ggtccctggc ttttgttcct      39819
tggaatggat gtagccaaca gtagctgaaa tattaagggc tcttcctgga ccatggatgc      39879
actctgtaaa ttctcatcat ttttattgt agaataaatg tagaatttta atgtagaata       39939
aatttattta atgtagaata aaaaataaaa aaactagagt agaatatcat aagttacaat      39999
ctgtgaatat ggaccagacc ctttgtagtt atcttacagc cacttgaact ctatacctt       40059
tactgaggac agaacaagct cctgatttgt tcatcttcct catcagaaat agaggcttat      40119
ggattttgga ttattcttat ctaagatcct ttcacaggag tagaataaga tctaattcta      40179
ttagctcaaa agcttttgct ggctcataga gacacattca gtaaatgaaa acgttgttct      40239
gagtagcttt caggattcct actaaattat gagtcatgtt tatcaatatt atttagaagt      40299
aatcataatc agtttgcttt ctgctgcttt tgccaaagag aggtgattat gttacttttt      40359
atagaaaatt atgcctattt agtgtggtga taatttattt ttttccattc tccatgtcct      40419
ctgtcctatc ctctccagca ttagaaagtc ctaggcaaga gacatcttgt ggataatgta      40479
tcaatgagtg atgtttaacg ttatcatttt cccaaagagt attttttcatc tttcctaaag    40539
atttttttt tttttttttg agatggagtt tcattctgtc acccaggctg agtgcagtgg       40599
cacgatctcg gcttaacgct tactgcatcc tctgcctccc agattcaagc agttctcctg     40659
cctcagcctc tgagtagctg ggattacagg tgtgcaccac cacaccagct aatttttttt     40719
ttttttttttt tttttttgag gcagagtctc gctctgtcac ccaggctgga gtgcagtggc    40779
gccatcttgg ctcactgcaa gctccacctc ccgggttcag gccgttctcc tgcctcagcc     40839
tcctgagtag ctggtaccac aggcaccccac catcatgccc ggctaatttt ttgtattttt    40899
agtagagatg gggtttcacc ttgttagcca ggatggtgtc gatctcctga actcgtgatc     40959
cacccgcctc ggcctcctaa agtgctggga ttacagatgt gagccaccgc acctggcccc    41019
agttgtaatt gtgaatatct catacctatc cctattggca gtgtcttagt tttattttt     41079
attatcttta ttgtggcagc cattattcct gtctctatct ccagtcttac atcctcctta    41139
ctgccacaag aatgatcatt ctaaacatga atcctaccct gtgactccca tgtgactccc    41199
```

```
cgccttaaaa actgtcaaaa gctaccggtt acctgaaggg taaaagtcaa gtcccctact    41259
tacctcatgt catctagagc aagagatgaa ctagctgagt tttctgacca cagtgttctt    41319
tcttatgtat gttcttttgt acgtgctctt ttctatatat agggaaccat ttctctcttc    41379
cagttgtttt gctcagtgaa tttctattcc tgtttcaaaa cttgttcagg cattaccttt    41439
tttttcttaa gcatacttt tttaatggaa caaagtcact cctgtctaca ctagttctgc     41499
atcttataca taggttttgt acatagtaca tatttatatc acatcaaatt atatgtgttt    41559
acatatctgt cttccttaat ggaatataag tcttttgata taaggaacta tttaatttgt    41619
ttctgtgtgt tgagtatctc ctgtttggca cagagttcaa gctaatacat gagagtgatt    41679
agtggtggag agccacagtg catgtggtgt caaatatggt gcttaggaaa ttattgttgc    41739
tttttgagag gtaaaggttc atgagactag aggtcacgaa aatcagattt catgtgtgaa    41799
gaatggaata gataataagg aaatacaaaa actggatggg taataaagca aagaaaaac     41859 ttgaaatttg atagtagaag aaaaaagaaa tagatgtaga ttgaggtaga atcaagaaga    41919
ggattctttt tttgttgttt tttttttttga aacagagtct cactgtgttg cccaggctgg    41979
agtgcagtgg agtgatcttg gcttactgca acctctgcct cccaggttca gcgattctt     42039 ctgcttcagt ctcccgagta gctggaatta caggtgccca ccagcacggc cggctaattt    42099
agtagagaca gggttttgcc atgttggccg ggctggtctc aaactttgga tctcaggtaa    42159
tccgccagcc tcaacttccc aaagtgctgg gattacaggc atgagccact gtgcccagcc    42219 tgttttttt ttttaaagg agaccagtga agtttcagga ggagggaaag aaaatttaga     42279
gttactaggg agagagtgat gaagataaga gatgaaagtg gtaataaggg aaatagcaaa    42339
atatcagggt aggtgggaga aaaagagatt tgtaacaaac aataggatta tcctgtgaaa    42399
aaggatgaaa ggaagaaaaa aatggataga aagatatttt aaacaccctc agcctcctgt    42459
tttccctcct gtgtattcat agtatataaa actataatta tgtactttac ttaaaaaata    42519
tattattatt accttatcgt gcttatttaa tcatagcatg tcctcttttt agtctcatta    42579
ccctgtttgt attattcttc ataacactta atacctgaca ttgtattata tattggctta    42639
ttttccaggt actccactca aatataagtt ctaggatata atttatttat cactgaaatc    42699
cattgcttag agtacctggc atgtagtaaa taggcattct gttttttcaa ataaaaaata    42759
aaggaactta agatatatat ttatgttata tcgccagcct tttcctcac agctctattc     42819 tgttgtacag aattacctac tttacaattc ctgtgtttca aggggatctc aaatttaacg    42879
tgtccacaat gaactcctga tttctgtttc tctcctagtc attcttattt caatatatgt    42939
tcagttacct aaccagctag tcaaggcaga tactttagag ttattctgta gtcattcttt    42999
ttccctacca ttttgtttt ccaaatgtaa tttatgtgtg tcttcttcat cctcgcagct     43059
ctaacccttg tccaaaccag catcatcact catctggagt tccacaatgt ctttctggct    43119
agtttccctg atttctctat tgacccctt attctccaca gtgcagccag aatgattgtt     43179
taaaacttcc tccttaaaat ctttaaattg ttttctttta tacgttaagt taaattccag    43239
ttccttgtct tggcatgcca tgccctgcct ggtgtggccc ctgatggtct ctccaacttc    43299 atgtttact actattgact cttatttttg cttactctgc ttgggtgctc cagtcctcca    43359
aatcatttcc tgctccaatc atttcaatca tttttcctc tcagatctta tagtattcca     43419
aatgctttct tcctttggag catctgggtt tactaataaa tacttcgtac ctcacagttc    43479
agcttaaata tcaattattt ggtggttaag acatccttca accgctctat ctaaatgttc    43539 cttctatta ttcactggct cagtactctg ttttattt ctttctaaat gtcaacttt         43599
```

```
ttttttttga gtcagggtct cactgttgcc caggctcgag tgcagttgca caatcatagc   43659
tcattgcagc cttgccctcc tgggatcaag taattctccc acctcagcct ccaaaatagc   43719
tgggattaca ggtatgcatc accatgctca gctaatttt tgtgttttt tgtagagatg   43779 aggtctcact tgttgccca ggctggtctc aaactcctgg actcaagtga ttctcccacc   43839
tcagcctccc aaagtgctgg ggttacaggt gtgagccact gcacctggtc gatactgact   43899
tttttttttt tttgagatgg agttttgctc tgttgcccag gctagagcgc agtggtgtga   43959
tctcagctca ctgcaacctc cacctcccag gttaaaggga ttcttctgcc tcagtctcct   44019
gagtagctgg gattacaggc aagtgccatc atgactggct aattttttgta ttttttagcac  44079 tatgtttagt actgtgttgg ccaggcttgt ctcgaactcc tgacctcaag tgatccaccc   44139
acctcagcct cccaaagtgc tgggattaca ggtgtgagcc accgtaatcg ccaacattg   44199 acatttttag tagactttt gtttgtttac ttgcttatta tctgctgcct tccacactct   44259
ggcgaaatcc tgccacccac ccacacacac ataggcactg aatgggcaga actctgaagg   44319
ccagaatttt atatttcttt tcactgtaaa catcatcatc tgtcactgat ggcacactag   44379
gatgctcagc aactgtgtgc atgaaggaag taagcactag tttgtgaagg ctgcaaaact   44439
cttgagtatt ctaagagttt tggccaaaat gaatgtacag ctttagtggc agaagctaat   44499
actcagaaat tgaggccgta tattggataa cacaggattt ggatgattat tttaaaataa   44559 tatttttacat tgtatatatg tgtgtgtgtg tgtgtgtgtg tgtgtgtatg tgtgtgtgtg   44619
tgtatatata tatgtatgta tgtgtattag tccgttctca tgctgctatg aagaaatacc   44679
tgagactggg taatttataa aggaaagagg tttaattgac tcacagttcc acagagctgg   44739
ggaggcctca gaaaacttaa cagttatggc agaagggaa gcaaacacat ttttcttcac   44799
atggtggccg gaattagaag aatgtgagcc gagcaaaggg gaaagccct tataaaacca   44859 tcagacatcg tgagaactta ctattatgag aatagcgtgg gggaaaccac ccccacgatt   44919
caattacctc ccaccaaatc cctcccatga catatgagga ttatgggaac tatgattcaa   44979
gatgagattt gggtagggac acagccaaac catatcagta tgtatatgta tacaagtatt   45039
atatatatat gtatgtgttt gtatgcatac atgtattata tatggaggaa attctaattt   45099
tgtaaaaaac tggattgtga gttttaagga gatgttatat aaagttaaga caatgtcatt   45159
ttgtggtatt ggtctgaatt acaatgtagt ttcttagtga tatttttcct ttattcag   45217 tgt gaa aac atc tcc tta aaa gaa caa gtg gag tct ata aat aaa        45262
Cys Glu Asn Ile Ser Leu Lys Glu Gln Val Glu Ser Ile Asn Lys
          1000                1005                1010 gaa ctg gag att acc aag gaa aaa ctt cac act att gaa caa gcc        45307
Glu Leu Glu Ile Thr Lys Glu Lys Leu His Thr Ile Glu Gln Ala
    1015                1020                1025 tgg gaa cag gaa act aaa tta g gtaagtttta tgactctgat aatataaaat    45359
Trp Glu Gln Glu Thr Lys Leu
    1030 gattaacatc taataatgaa tatttcttat ttaaagttcc ttttttatgc tagattaaaa    45419 ggaagtattt tgactaaaaa aagaaagaac tttctgccta ataatttaac ttaggcagat    45479 gaataatcct gtacttaacc ccaccaaagt ttagttttca gtccttaagt tagatttgtt    45539 tctaatgaaa tcatatatgt taaaaattta tgactaagta ttagctactt tgaaccgttt    45599 aacaattaaa actgatgata ttttattaat ggtattatga gttctttcac tgagtgcaag    45659 ttatattagt tatatatcac ttgatatttt taaattaaaa gataccagga aacagcaaag    45719 aaaatgtgaa aagaagttgt atttctcata gttttactac tatattactg tatattttg    45779
```

```
ctcctatatg cttacatatt ttatatattt taaattatta taaacatggt tttatactgt   45839
atttagatag taatatcaaa aatattttta tggccggcgc agtggctcac acctgtaatt   45899
ccagcacttg ggaggctgag gagagcagat ccctgggt caggagttcg agaccagcct    45959
ggccaacatg gcaaaacccc atctctacta aaagtacaaa aattagccag gcgtggtggc   46019
agttgcctgt aattccatct actcaggagg ctgaggcagg agaattgctt gaacctagga   46079
gtcagaggtt gcagtgagcc aagatcatac cacagcactc cagcctaggc gataagagtg   46139
agactccgtc tcaaaaaaaa aaaaaattt gttttattca tcatacttat aaatacttat    46199
acaatagcct aatgtgtttg agtgattaaa tcactagctt tttatatttt tgctattgct   46259
tatagtgcca cagtgaacat tttcatgtat atctaacaga gatattactg tctcagaagg   46319
tattgaaatc tttgttgctc tcattagagt tttccatatt aattttttcaa acagttatat  46379 agtttataag attttcataa ttttatctca tatattgtgc ttcataattt tcaaataaat   46439
ttgctgcttt cgataatgta ttttcatgta tttgtttcct agacgttaga gctattcaag   46499 gttttttatta ctaaatagag ctgttctctt aaattggtaa tgagatactt ggtttagaga  46559
agcctaacac tgggaaatct tacataagct acttttagaa atgtaatttt tagctcaata   46619
agagattaaa tatgaattga cttttgtgta gtatttgcat ggaagaaggt accatttaaa   46679
tgaagacatg agagtattac gtacaatttt agtaggttct ttttatttta tcatctttat   46739
ttttaataaa tgctgaattc cctacagaaa ttctttaatt tttacatatc ttgatctctt   46799
tcatatatgg atttatatca ccgaagtttt aagagtgttt ccctattccc tgttgccctt   46859
atatctttgt ttaaaaatgt cacatcatta gcttttttc atctaggaat ttgttagtgt    46919
tgggctgttg tgctctaccc tctcttaag aaaactccaa acccaaaaac atacaagatg    46979
gctagtctgc ttcagccttt gtgatgtgct tttctcttct aatcagagtt agcacaata    47039 cagaatggag aaggactcct ttatatattg gtatttattg cagtattttt ctacatggtg   47099
cctaaggtta cttgaatgag tctttattcc ataatgaact gatttactaa tgcttttagc   47159
acctgttagt gatccattat tgttagttac ttgattactg cttgccacag ctattctaaa   47219
ataatacatt ttaaagataa atacagaaca taatgaagta ctttttaaaa ctgagataga   47279 gaccaattt tttttcagga aatgtatatt actttgagaa aactcagtta taaaacttga    47339
acttatgaag ctggaaaaac aggagggggc attattggta ttgtaaaagg ctgtttacaa   47399
agtgagttgc tgcttagttc ctttaagtaa ttggctaccc taaacacatc agttttaagt   47459
tgctgaaaag caaaacactc taccaaattt tgttttttt ctagaccatg tttacaaagc    47519
aaaagtatgt tttcttcccc cccctcaaa aaatgactaa tgcactcct atgcgatgcc     47579 tttttatggt aaattgaggc ttttagttct ctttccattt agccacagac ttttgtgtcc   47639
aaagacaagc tgcgtaactg catatataag gttaaggcat aactactaat aaaagaatgt   47699
aaaatatttg atattaggtc tgtacaaaga ccaaataata ctcatgatta gacaagatta   47759
tatttggtag aatctatcca tcatatggct tcagatttta cttttcagct tggctttgtg   47819
agactttaaa aatcaagtca ttgcacttat attcacaaag tcacattgct ttactgcatt   47879
gcttctcata cagtttatct cctttcagta aaatgtttac ttgccatttt taaaatttct   47939
tatatgtgac acttctacac taagtccttt atgttgttag ttccacaatt ctgtgaggaa   47999
taggtttttt tttttaatca tttgattgat gaagaacatt aagttccaca gagattaaat   48059
ggtacaggca tcacacaggc aggaagtaac agagctaaga ttagagtcca ggtctgatgg   48119
```

```
aattcagaaa gctaatgtgc tttccatgga actataatgc tttctaatat acagcatcta    48179
aaatatctga ggtaatttta atataaacag catgagattg acttaaatat tattgcatgt    48239 ag gt   aat gaa tct agc atg gat aag gca aag aaa tca ata acc aac      48285
   Gly  Asn Glu Ser Ser Met Asp Lys Ala Lys Lys Ser Ile Thr Asn
   1035             1040                1045 agt gac att gtt tcc att tca aaa aaa ata act  atg ctg gaa atg         48330
Ser Asp Ile Val Ser Ile Ser Lys Lys Ile Thr  Met Leu Glu Met
1050            1055                1060 aag gaa tta aat gaa agg cag cgg gct gaa cat tgt caa aaa atg          48375
Lys Glu Leu Asn Glu Arg Gln Arg Ala Glu His Cys Gln Lys Met
1065            1070                1075 tat gaa cac tta cgg act tcg tta aag caa atg gag gaa cgt aat          48420
Tyr Glu His Leu Arg Thr Ser Leu Lys Gln Met Glu Glu Arg Asn
1080            1085                1090 ttt gaa ttg gaa acc aaa ttt gct gag gtttgatatt ataagtttta            48467
Phe Glu Leu Glu Thr Lys Phe Ala Glu
1095            1100 tcatacaatt atagaataaa gaattagttt tggtagacat tgtattattg ttaagtggtt    48527
tgtctggatc tctgaaatat cttattaata tagtgcctat gttttgtgta ataataaat     48587 aaaagattta aatctgaatt gtttaaaagg aaagcagata tttctgtaag ttttttctcac   48647 caatgttata ttattagatt taatttatga aatgttattt actaaacaat ggaattgcct    48707
ttcaccacca tcccttcatt taacaaatat ttattcattg cctattacat gtcagaccct    48767
gtgttgggac tggcagtata gcaagaaaca aaatagacaa taatctctac tttcagggac    48827
tttacattct aattggtggt tttatatatt tttgatgtgg tcagaatcat taaactgtgt    48887
ggcagtaaat atagtttgca agtatttaac aatttatgat taaacacaac tcttacagtg    48947
tttgcttacc ttgagattta atatattttc aaagcattta tatcattttt gttttaacta    49007
tgtcactaaa tctatatgag taagatttta ttaactcatt tggatttatt tatagatgat    49067
acaattgaag taaatatataa tgagcagatt gcattctaag caaagtaaga atattgcaag   49127
ttcagatatt attagataat gagttgccta ataaaaatga cttttggtgg attggaatat    49187
aaccagagtt tccatagttt gtttctgatt ctttcatatt ttttaccctc cttcagtctg    49247
ttcttaacac ttcacactta atataatatg tgaactaagg ccaagtaaag aggattgcag    49307
tactttaaaa gctaaattac aaagaaaacc tcaccaaaaa ttgatgtatc tgaacatttt    49367
ttgttacatt tccttag ctt acc  aaa atc aat ttg gat  gca cag aag gtg    49417
                   Leu Thr  Lys Ile Asn Leu Asp  Ala Gln Lys Val
                                 1105                  1110 gaa cag atg tta aga gat gaa tta gct gat agt  gtg agc aag gca         49462
Glu Gln Met Leu Arg Asp Glu Leu Ala Asp Ser  Val Ser Lys Ala
1115            1120                1125 gta agt gat gct gat agg caa cgg att cta gaa  tta gag aag aat         49507
Val Ser Asp Ala Asp Arg Gln Arg Ile Leu Glu  Leu Glu Lys Asn
1130            1135                1140 gaa atg gaa cta aaa gtt gaa gtg tca aa gtaagtgcat ataagcattt         49556
Glu Met Glu Leu Lys Val Glu Val Ser Lys
1145                1150 tagccatttg actagatgta tcttctttaa tttgtcttta agaaacccaa ttacaggtat    49616
acaattctta gtagtaattg atactgatttt cttttataa gaacaggatt aagtaatatt    49676
aagatcggtt ttaacagggt taaataataa tattgacgag aataaattg ttaaagagga    49736 agtgacctct caagatttgc atttttttaga gttcaggaat attattgcag aaaggtccag   49796
ttcctccaca tattgatttt tggggaagg ggtgatggag gaggaatggt tgtttattgt     49856
```

| | |
|---|---|
| atttaaactt aagtttcttc attttaataa gggagtaata gtacctcttc tacctgtttc | 49916 |
| ataaggttgc tgtaagaata taataaaaaa ttcagattttt gatttagttt acatttatcg | 49976 |
| ggcatctact atgtactagt cacggtgcaa ggtattaaac atatattgac ttgtacaatt | 50036 |
| atacttaacc ttgaggttat attttttgttt tcatttttaca tgaagaaata tgcccagcta | 50096 |
| gtttagaaca caaaatatat ataaggagta aatactgcgt gctggctggg cgtggtgaca | 50156 |
| tgtgcctgta gccccagcta ctcgggaggc agaggcagga gaatcgcttg atcccgggag | 50216 |
| gtggaggttg cagtgagccg agatcgcgcc actgcactcc tgcctggtga cagagcgaga | 50276 |
| ctctgtcaaa caaacaaaca aacaaagaaa aacaaaacaa aaaaaccgtg tgccagctat | 50336 |
| atgctgtatt ttcattctct tttgtaatta ggtgatattt cagtagaaaa gtataaggag | 50396 |
| cacttagtta atctgtcaag cataaatagt aaaaatattt tatggcctac tcataaaaat | 50456 |
| ataaccattc ctttggagcc ttgatagttc tcttgggaat atcagttttt gacatctttt | 50516 |
| tcactatgaa agacccttttt ttttaaaaaa attgatcctt tcttctcatg gacctctttt | 50576 |
| gatataaact aacttataat agttcattttt aatcatattt tgttaatcat gcaactggca | 50636 |
| atgagagcct ctcatcagta tgaggaaacc tgccttatct ataatactga actaaaatta | 50696 |
| ttctaaccca agcaaagaa actttacatt ttgcttttgcc tgtattagct tatcacagta | 50756 |
| ttcatgaggg aatttgaagg acttattacc attaggctat ctcttttttt ttttttttgt | 50816 |
| aattttatta aatgcatgtt ttgtttcttt tcacattact gataacttgt agattaaaac | 50876 |
| aaatcaaaac atgcattaat ccatctaagg atcctagaaa ttttacattt ctgtgttctt | 50936 |
| aactgtgtga tggtcttaga taaatgtact aaataccttta tcctagcata ttccaaatta | 50996 |
| tgacaataaa tgttttatgg aaaaaagtat gggaacagaa gttctttggc tatatacatt | 51056 |
| tggaaaatac tatatagtaa gtatgatttg agataattat atatgataga acctctggga | 51116 |
| gcactgaata tatgttagga atattcaaga gggaggaggg atgttgagaa tgaagttttt | 51176 |
| tttatatagc aaacatgata acctctgatg gaattatgtt tcatgaaaca gtttaggaaa | 51236 |
| tcctgtttta atatttcata caaagaagag atagatgctg aaaacgaatg gcttttttgaa | 51296 |
| aaagggtcta gaaattttga attttggcat ttacttagaa agtgtactta attgttcctg | 51356 |

| aaataccttta tcatttccta g a ctg aga gag att tct gat att gcc aga | 51405 |
| | Leu Arg Glu Ile Ser Asp Ile Ala Arg | |
| | 1155 1160 | |
| aga caa gtt gaa att ttg aat gca caa caa caa tct agg gac aag | 51450 |
| Arg Gln Val Glu Ile Leu Asn Ala Gln Gln Gln Ser Arg Asp Lys | |
| 1165 1170 1175 | |
| gaa gta gag tcc ctc aga atg caa ctg cta gac tat cag gtatgtgcag | 51499 |
| Glu Val Glu Ser Leu Arg Met Gln Leu Leu Asp Tyr Gln | |
| 1180 1185 1190 | |

| | |
|---|---|
| tattggctct tctacataga atccactttt ttccctaaat ttacattaga tgttgggagt | 51559 |
| gggatatgtt atacttttttg tttgtttcga gatagggtct cattctgttg cccagggtgg | 51619 |
| agtgcagtgg tacattcaag gctcattgca gccttcacca cctgggttca ggtgatcctc | 51679 |
| ccacctcagc tcttagaca gctgggacta caggcacgtg ccaccacacc taatttttttt | 51739 |
| gcatttttttg tagagacagg gtttcaccat gttgcctagg ctggtcccaa actcctgggt | 51799 |
| taaaatgatc tgcccacctt gacttcccag aatgctggga ttacaggtat gagccaccat | 51859 |
| gctgggccat tgttacattt ttaatcaaaa gatataccaa ccagaggctg ttattcttgt | 51919 |
| tagttggaac ctgattagaa agctctttaa tttgaaatat tgttcagtaa tccagtacag | 51979 |
| catttaaatg cctatagatg aattatgctg ctgatcaaaa ttaggacact gagaattgta | 52039 |

```
gttagtaaat ctttaataac aatattttct cttgtattta tatgtaactt tttacatatt    52099
cttacgttat atatgttggg aattataaaa acatacacat tgtcctgatc agtattatgt    52159
tacttgcaat ggaggttaaa aaaaaactgt aacagtcagg catggtggct cacgcctgta    52219
atcccagcac tctgggaggc cgaggcaggc ggatcacgag gtcaggagtt cgagaccagc    52279
ctgaccaata tggtgaaacc ccgtccctac taaaaataca aaagttagcc aggcgtggtg    52339
gcatgtgcct gtaatcccag ctacccagga ggctgaggca ggagaattgc ttgaacccgg    52399
gaggtggagg ttgcagtgag ccaaaatcac gccattgcac tccagcttgg gtgacagagt    52459
gaaactctgt ctcaaaaaaa aaaaaaaaaa acaccagtaa catacccact gttattcagt    52519
tacatttgga tttttaagttt gtttgattct aggttttttc ttttacagtt ctttggtaat    52579
tatttgtatt aaagcaaagt tacatttttg tagatctcat gtgccactgt gttaaaactt    52639
tgcttagtaa attgtgaatt ttaaatctgt gataactttc actggaaaaa tttgaaactt    52699
actacaaata tatattttt ttaatatcag gca cag tct gat  gaa aag tcg ctc    52753
                                Ala Gln Ser Asp  Glu Lys Ser Leu
                                                 1195 att gcc aag ttg cac caa cat aat gtc tct ctt  caa ctg agt gag         52798
Ile Ala Lys Leu His Gln His Asn Val Ser Leu  Gln Leu Ser Glu
1200                1205                      1210 gct act gct ctt ggt aag ttg gag tca att aca  tct aaa ctg cag         52843
Ala Thr Ala Leu Gly Lys Leu Glu Ser Ile Thr  Ser Lys Leu Gln
1215                1220                      1225 aag atg gag gcc tac aac ttg cgc tta gag cag  aaa ctt gat gaa         52888
Lys Met Glu Ala Tyr Asn Leu Arg Leu Glu Gln  Lys Leu Asp Glu
1230                1235                      1240 aaa gaa cag gct ctc tat tat gct cgt ttg gag  gga aga aac aga         52933
Lys Glu Gln Ala Leu Tyr Tyr Ala Arg Leu Glu  Gly Arg Asn Arg
1245                1250                      1255 gca aaa cat ctg cgc caa aca att cag tct cta  cga cga cag ttt         52978
Ala Lys His Leu Arg Gln Thr Ile Gln Ser Leu  Arg Arg Gln Phe
1260                1265                      1270 agt gga gct tta ccc ttg gca caa cag gaa aag  ttc tcc aaa aca         53023
Ser Gly Ala Leu Pro Leu Ala Gln Gln Glu Lys  Phe Ser Lys Thr
1275                1280                      1285 atg att caa cta caa aat gac aaa ctt aag ata  atg caa gaa atg         53068
Met Ile Gln Leu Gln Asn Asp Lys Leu Lys Ile  Met Gln Glu Met
1290                1295                      1300 aaa aat tct caa caa gaa cat aga aat atg gag  aac aaa aca ttg         53113
Lys Asn Ser Gln Gln Glu His Arg Asn Met Glu  Asn Lys Thr Leu
1305                1310                      1315 gag atg gaa tta aaa tta aag ggc ctg gaa gag  tta ata agc act         53158
Glu Met Glu Leu Lys Leu Lys Gly Leu Glu Glu  Leu Ile Ser Thr
1320                1325                      1330 tta aag gat acc aaa gga gcc caa aag gtaaacattt aaacttgatt            53205
Leu Lys Asp Thr Lys Gly Ala Gln Lys
1335                1340 ttttttttta agagacagta tcttgatctg tttcccaggc tggagttcag tggtgcaaac    53265
atagctggaa ctcctgggct caagggactc tctagcctca gcctcctgag tagttgtagc    53325
tggcagtaca ggtgcacacc accataccta cctaatttt taaattttt aaattttttt      53385 gtagagacaa ggtctcactt tgtcacccag gctggccttg aactcctggc ttcaagtaat    53445
cctcctgctt tggtctctca aaagtgctga gattacaggc atgagccact gtgcccagcc    53505 aatttttaaat tcattatctt caaaagagtt acatgataat ttcttaatat atgcctatat   53565
gaaaaatgct taagatacaa attccaatta tgattcatta atttagattt tataacttag    53625
```

-continued

```
cagtgttggc tatttgaatg tctattatac gtaaaaataa aattaggctt ttctaaccaa    53685
agattttagt gggaatgttc agattgtata atagcaaaga attttaatta ctataggaaa    53745
atttatatta attaaacact aattattata tttaaacatt gtagtagtta tcagttgatt    53805
tctactgttc ataattatct ttgatctaca agtagtgggc ccacatttac ttttaatatg    53865
gtttaatctt catttagaaa gaattaaatg aaaataatt atcttgcaac tacatcctgt     53925
tctctaggct agaaacattt aggatttctg tttttgaaag taataccaaa gttccaatga    53985
cctgcttata gtcagtgttc aataaacgta taacaaatga aagtgaatat tagtgatgtc    54045
cattccaaca taatttgaag atttttattg taaaatccca catatttgta gaaaagtcta   54105
tggaaatcct aaataagatt ttgtcatgta gtttgacaaa agataacatt gtgtcttatt    54165 ttatttaga atggccatta cttttcaatta aaatcattat catcaatgga ggaatgttat    54225
ttgttaatat agcatttata tttgtgtata taaattgtaa atcttag gta atc  aac    54281
                                                   Val Ile  Asn
                                                   1345
```

```
tgg cat atg aaa ata gaa gaa ctt cgt ctt caa gaa ctt aaa cta           54326
Trp His Met Lys Ile Glu Glu Leu Arg Leu Gln Glu Leu Lys Leu
        1350                1355                1360 aat cgg gaa tta gtc aag gat aaa gaa gaa ata aaa tat ttg aat           54371
Asn Arg Glu Leu Val Lys Asp Lys Glu Glu Ile Lys Tyr Leu Asn
            1365                1370                1375 aac ata att tct gaa tat gaa cgt aca atc agc agt ctt gaa gaa           54416
Asn Ile Ile Ser Glu Tyr Glu Arg Thr Ile Ser Ser Leu Glu Glu
                1380                1385                1390 gaa att gtg caa cag aac aag gttttatttt atatttattt catttttttc         54467
Glu Ile Val Gln Gln Asn Lys
                    1395
```

```
cctaagtttt tttttttttt tttttttttt gagatggagt ctcactctgt cgcccagact    54527
ggagtgcagt ggcgtgatct cggctcactg caagctctgc ctcccgggtt catgccattc    54587
tcctgcctca gcctcccaag tagctgggac tacaggcacc cgccaccgtg cctggctaat    54647 ttttgtatt tttagtagag acggggtttc accatattag ccaggatggt cttgatctcc     54707
tgacctcatg atccgcccgc ctcggcctcc caaagtgctg ggattacagg cgtgagcccc    54767
taagatttta aacaagaata ttgcacaaat gactatgtta tccttctaat taagtgcacc    54827
ttccattact aattgattat ataataattt gttttttatt ttctaaacta ttctaaaaat    54887
tcatatttat ttagctttta taacagtagt cttaatctta aaaacggcaa tacataagca    54947
acctcatttg gtaagttaat ttttattttg atattggtta tttgactttt cacagttcca    55007
cgtttctact ggctctcact gatagagtaa gaagtcagct tcttatagaa taaagtatat    55067
acttcagaga cagatgaaat tcgtcaaaca tatgactgtc tcagagattg ttccccctgc    55127
ttaaattgtt cttaccctag atacctttgg tatttacact gtcagtgcct gcaggtctta    55187
gctcaaatgt cttaccttat cagtgtatcc ttcaccagcc acctaatata caacagtaaa    55247
tcctactatc cagattccta aatagagatt aattaactta attttctcc aaagtgcttg     55307 taaccttctg acgtattaca tacttactgg tttattattg actgtctttc cttcgccaga    55367
atgcaagttc cgtggtgaca cggacttggt tttgtttact gccatgtttg tatttcctag    55427
aatgatgctt ggcacataat atatgtcatc aaatatcttt cgtatagctg aacggatgga    55487
tggatggatg gatggatgga tgatagact gaaatcctta cttcacatct gcctttgtga     55547
tcttacacaa gttacttcac ctctctgagt ttgtatttt ttccataaaa ggaaaataat     55607
tacagtttct tcaatgtgtt gtgaggatta gataagaaaa tatatataaa atgcctgtta    55667
```

```
tgtgcctgat gtcttcgtgt atgtgtctga cacaaattgt cctttttta g ttt cat      55724
                                                        Phe His
                                                            1400 gaa gaa aga caa atg gcc tgg gat caa aga gaa gtt gac ctg gaa          55769
Glu Glu Arg Gln Met Ala Trp Asp Gln Arg Glu Val Asp Leu Glu
                    1405                1410                1415 cgc caa cta gac att ttt gac cgt cag caa aat gaa ata cta aat          55814
Arg Gln Leu Asp Ile Phe Asp Arg Gln Gln Asn Glu Ile Leu Asn
                1420                1425                1430 gcg gca caa aag gtatgaatga ttaatcttgt ttgttactct gtagcatagt          55866
Ala Ala Gln Lys ctagagtgtt aactcacaga atatttcct gtatcagatg taattttaat tgatgttata     55926
ttgtatattt aaaatataag aggggtttaa tctatgtttt atcatacagc tgtaaaaatt    55986
aatagttact ctcaatgctg caactgcttt ttaaaaaac atactatttc ttaatag        56043 ttt gaa gaa gct aca gga tca atc cct gac cct agt ttg ccc ctt          56088
Phe Glu Glu Ala Thr Gly Ser Ile Pro Asp Pro Ser Leu Pro Leu
1435                1440                1445 cca aat caa ctt gag atc gct cta agg aaa att aag gag aac att          56133
Pro Asn Gln Leu Glu Ile Ala Leu Arg Lys Ile Lys Glu Asn Ile
1450                1455                1460 cga ata att cta gaa aca cgg gca act tgc aaa tca cta gaa gag          56178
Arg Ile Ile Leu Glu Thr Arg Ala Thr Cys Lys Ser Leu Glu Glu
1465                1470                1475 gtaattagaa gaatttgcat tttgattagt gtattatttg gtatgtttgg ggggctttct    56238
aaataatatt tctttatgag ggcaatgcat agaatgatga atctattgct aatttcacta    56298
tttttctatt ctcctataat gtttctaata gccataatg aacagcagat atagttaatt     56358
tgaattcact atttaattat tagttggtac ctttcggtac actgaatatg aaaggaaata    56418
aaaagcattt aattgtagtt ctatgagcaa tatattctct tatatgatct ctttattctt    56478
acttttttgg ttttattttg aagtgcatgt tacataatct atgaatcaat ttcagttca     56538 ttgcctttaa tgcatggtta aagggttgaa ggtaaattag aaattacttt ctgttttaac    56598
ctagatcttg aatttgatta gtaggtgatc aaatctgtca tcttcattaa attattcaga    56658
aaataatgta aactgaatgt gttttcatt tagttttcat ctaaataaac tgcaaataca     56718
tttaaaatat acataaagaa gttttcaag taaaactgta catttttaat catttcagga     56778
aacgtagatt tcttcagta atttaagat ttgtcatttat tgtgaattgc cattgaatta     56838
cttaatttaa aatactcacc ttaatcctct tgaagagtaa aaattttct gttttttct      56898 ctttgtttta ataagctgcg gatttatat tcgtaattta ttgagttggg cctctaaaat     56958
tccagttttg tacttaactg acttatagat tagtctccta atgctctgct agtcaatgga    57018
ccaaaataaa agaaataatt tattacatat tcttcctaaa tctagtacca ccatacatgt    57078
ataattctaa actgtaatat ctcaataaag taccttaatt aaattttatg ttcatcataa    57138
caatgaagtt tctagcatat gtaatagtct tataaataag catgcaaata actgctgtca    57198
attagaatta gtcagtttaa ccttattaag tatcaaatgg ctattgtaca tatgatgtga    57258
aaaataaagt gaattttttt tggctaataa ctaatctaaa attcagatga agcatttaa     57318 agggaaaaag atactttaat gatttattat aatttaatca ttgcag aaa cta aaa      57373
                                                    Lys Leu Lys
                                                        1480 gag aaa gaa tct gct tta agg tta gca gaa caa aat ata ctg tca          57418
Glu Lys Glu Ser Ala Leu Arg Leu Ala Glu Gln Asn Ile Leu Ser
        1485                1490                1495
```

```
aga gac aaa gta atc aat gaa ctg agg ctt cga ttg cct gcc act          57463
Arg Asp Lys Val Ile Asn Glu Leu Arg Leu Arg Leu Pro Ala Thr
        1500                1505                1510 gca gaa aga gaa aag ctc ata gct gag cta ggc aga aaa gag atg          57508
Ala Glu Arg Glu Lys Leu Ile Ala Glu Leu Gly Arg Lys Glu Met
        1515                1520                1525 gaa cca aaa tct cac cac aca ttg aaa att gct cat caa acc att          57553
Glu Pro Lys Ser His His Thr Leu Lys Ile Ala His Gln Thr Ile
        1530                1535                1540 gca aac atg caa gca agg tta aat caa aaa gaa gaa gta tta aag          57598
Ala Asn Met Gln Ala Arg Leu Asn Gln Lys Glu Glu Val Leu Lys
        1545                1550                1555 aag tat caa cgt ctt cta gaa aaa gcc aga gag gtattttatt               57641
Lys Tyr Gln Arg Leu Leu Glu Lys Ala Arg Glu
        1560                1565 atattatgag ttatgctgtt atccattagt ttttttaagc aaatgctaaa tattatttta    57701
ccctaaagtg gtatttcttt tcttgctttc aaatgattct atttaagaat tgttacttgc    57761
atgtgattgg attacacctc tgtcagtaaa actggaagtt tgtgtacatg tatctttcta    57821
ttatacactg actaaaccac gagtagctat catggtgaaa tcatatgatt ttgaaaaata    57881
ttttaattga gtttataggt gaggattgag gcaatagggt ggaatgaaat atcacacc     57941 ggtaatcagt agaaatcaga tttgttagaa cttcgtgggg gaaagctaac atttaatttt    58001
ttctagaagt aagttaaaag atgatagata catgtcattc taatgttaag aataaattat    58061
gaactgaggc tgggcttgtc aacttgaaca ttgtctgagg ggacatgcat accagtctag    58121
atacatacat atatggagat actgtttctt cctcatctca aaggaatttt agaagattga    58181
agagaaaata tataaggtct tcaaaatgtg aatttgtttt aatcacaatt taagatatag    58241
tttcgatttt ctgtaaaaca g gag caa aga gaa att gtg aag aaa cat gag     58292
                        Glu Gln Arg Glu Ile Val Lys Lys His Glu
                                1570                1575 gaa gac ctt cat att ctt cat cac aga tta gaa cta cag gct gat          58337
Glu Asp Leu His Ile Leu His His Arg Leu Glu Leu Gln Ala Asp
        1580                1585                1590 agt tca cta aat aaa ttc aaa caa acg gct tgg gtaagattct              58380
Ser Ser Leu Asn Lys Phe Lys Gln Thr Ala Trp
        1595                1600 aagaactttg ttccattctt tattgatttt tgtgaccatg taaattaaaa ttcagctctc    58440
ttcttttttg gaatggaagt taccctttt gttgccaaaa taatcttctg aaaacatagc    58500
tctgatcatt cttcctcctg tagctcaccg ctgttcacaa aattatattt ataattctta    58560
gccatgtact caatctgcta tgaacctacc tgcctttctt ttcaaattct actcactgtg    58620
agtttagcta tatctaactt ccagaattca gctcatattt gcctcttttg accattctgt    58680
tccatatgta tgaaatgaca tgtctttcat ctttaatgt gtaaccttag catatttgag    58740
cattacctcg ttaattcggt caacacttat tgatctcctg ctacgtgcag acattttgct    58800
agctattgta aatacaaata ataaagtctg catttcctgt cttctttaag ccttcattgc    58860
ctattaaatc attcatttt agattagata ttatattttg atcatttgag gaaccaaatt    58920
aaaaatatgg aataagtatg gcattgaatt atacatgcct attgctaata tattcatatt    58980 ttatag gat tta atg aaa cag tct ccc act cca gtt cct acc aac aag      59028
        Asp Leu Met Lys Gln Ser Pro Thr Pro Val Pro Thr Asn Lys
            1605                1610                1615 cat ttt att cgt ctg gct gag atg gaa cag aca gta gca gaa caa          59073
His Phe Ile Arg Leu Ala Glu Met Glu Gln Thr Val Ala Glu Gln
        1620                1625                1630
```

```
gat gac tct ctt tcc tca ctc ttg gtc aaa cta aag aaa gta tca            59118
Asp Asp Ser Leu Ser Ser Leu Leu Val Lys Leu Lys Lys Val Ser
    1635                1640                1645 caa gat ttg gag aga caa aga gaa atc act gaa tta aaa gta aaa            59163
Gln Asp Leu Glu Arg Gln Arg Glu Ile Thr Glu Leu Lys Val Lys
    1650                1655                1660 gaa ttt gaa aat atc aaa tta ca  gtaagtcttc gaaatgtatt                  59206
Glu Phe Glu Asn Ile Lys Leu Gln
    1665                1670 gtaaaaatag gcaaatgata agtgatataa tgaagataaa cataagtgtt tgctatgcca      59266
ggcactgttc taagactttt aagtatattg tctcattttt atcctcagga ctgctggtta      59326
catatgttat cattttcccc attttaaaga gaggatatgg cctcaggaat gcttaatagc      59386
atgtctgggg gtagatggga aagccataat ttgaaactag tcagtctgac tcaaaagcca      59446
atacaaattc ttttccagaa tctcattttt accttctttg agcctcagtt tcatcttatt      59506
tatttatttt tattttgag acaaggtctg gctctatttc ctaggctgga gtgcagtgac       59566
ataatctcag ctcactgcaa ccttgacctt ccaggctcaa accatcttcc cacctcagcc      59626
tgcagagtag ctggcactac aggcaggtgc caccacacct gggtagtttt tttgtatttt      59686
tgtagagaca aggtttctcc atgttgccca ggctggtctt gaactcgtga gctcaagtga      59746
tccgcccact tcggcctccc aaagtgctgg gattacaggc ctgagccatt gcacccagcc      59806
tcatcatctt taaaatggaa ataataatac ttaccctggc cctttcaggg tggttatatg      59866
aaggtcaaat tataccgtgt atgaaagtaa tttgaaaact gtaaaataac atacagatag      59926
aaaacttttg attacacact tataagagtg tctgtcatat aatagagatt ctaaacattg      59986
ttcaaccact ttatcagaac gtagatttta aactcaaaat aggtttatag ttaggtagtt      60046
tctaatcatt ataatattat ctctatgggc ctaaatttta ttatctgaaa aaacatgaga      60106
aaattgaact gcttgactta taattccatt tcagctctca agccctgct agagtctttg       60166
attctttact cacttattca aatgcctctg acagaattaa cactattttt gctttgctaa      60226
ggagctgcca ctgttaagaa attactctct aaaagaaaga aaattggcaa cagcatatgt      60286
gtattttcag tctcttttcc tcactctatt aaattttgta caagagatgt tattttttggt     60346
ctagtaaatt tctgtcatgt tttggagtat aaaattactt gtgcttttgc atctaatttg      60406
tgggtgtaga aaatcataat cttttgaaat accttatata atacattttt ttgccacagg      60466
aaatacttga agttattgtt gtgtaccta cgtcatttta gtccaaaatt atacttgtgt       60526
tctctgtgtg catattttga tatgtattag gagattatgg atctgtgtga tttcttaagt      60586
aaatcctgat attttcacaa tttgatgatg actctttaaa gttagactta agttttgcca      60646
aaagcaagaa gcctcaaaga gtaacatttg ttcatgtctt aacactatct ccctcttatt      60706
ggtcagaatc tcagtatgga tgcagtgtcc atatgcacaa caatatatta attcagttta      60766
acagacttaa tgctgaataa gcaataagat taattgaatt aactaaatct tttgatagta      60826
tccacttcca tatatatagt tatagatata atgctagtga atttgaacca taaacaaatt      60886
aataatacat gtgatttctg tgaaaattta tattagtctt ttcaatatgt caatataggg      60946
cagtatttct caaatataga ggatcagttt ttcaccattg tccctcttgg ggacatttgg      61006
cgatgtctgg agacattttt gattgtcatg gctcggggt gctactggta tccagtgggt       61066
agaatcaaaa gatgctgcta acatcctat catgcacaag gcagccccac caccaacaaa       61126
gaattatcca gtcaaaaatg ttactagtag tatggttagg aaactatcat atagaggaag      61186
caatcacatt ttacaagagc cataatattt aaaatgcctt tttgttcatt ctctgtatat      61246
```

```
ttgactagag tcacaaaata acttgataag attgttgcca aaaatattag aaactagaag    61306
aaaaatgtgt tgttaagtct aagagtagtt aaatgaaata aagaattatt cttctttgga    61366
tttggatgcc tgcatcaaga tttagattgt aaggatactt aggactgaac atttgctcta    61426
tatgaaattt gtattaatca aggtatgaat tgcagcaacc actctattaa ttacatatgt    61486
ttggccaggt gtggtggctc acacctgtaa tcccagcaat tgggatgcc aaagcgggct     61546 tatcacctga ggtcatgcgt tcaaactggc ctggccaaca tggtgaaacc ccatctctac    61606
taaaaataca aaaattagct gggcctgatg gtgcacgccc gtagtcccag ctactcagga    61666
agttgaggca aaaaaatcac ttgaatctgg gaggcagagg ttgcagtcag ccgagattgc    61726
gctgctgcac tccagcctgg gtgacagagt gagactgggt ctcaaaaaaa ttaaaaatta    61786
aaaaacacac acacacatat gtttatttac atcag g ctt caa gaa aac  cat gaa    61840
                                       Leu Gln Glu Asn  His Glu
                                                        1675 gat gaa gtg  aaa aaa gta  aaa gcg  gaa gta gag gat tta  aag tat      61885
Asp Glu Val  Lys Lys Val  Lys Ala  Glu Val Glu Asp Leu  Lys Tyr
             1680          1685                         1690 ctt ctg gac cag tca  caa aag gag  tca cag tgt tta aaa  tct gaa       61930
Leu Leu Asp Gln Ser  Gln Lys Glu  Ser Gln Cys Leu Lys  Ser Glu
1695                 1700                              1705 ctt cag gct caa aaa gaa gca aat  tca aga gct cca aca  act aca        61975
Leu Gln Ala Gln Lys Glu Ala Asn  Ser Arg Ala Pro Thr  Thr Thr
1710                 1715                             1720 atg aga aat cta gta gaa cgg cta  aag agc caa tta gcc  ttg aag        62020
Met Arg Asn Leu Val Glu Arg Leu  Lys Ser Gln Leu Ala  Leu Lys
         1725                    1730                 1735 gag aaa caa  cag aaa gtaagtaaca acagaaaatt atcaacattt aggaaaaata     62075
Glu Lys Gln  Gln Lys
             1740 tgtggtagat tgcttttaga gaagatttgt aaatttataa aagatggtag tataaatctc    62135 cgtgttgtaa taaaaagtat gagctttatc ttatgctgtt aaacaaggta ttttagacaa    62195 tgctgttttt gtgggcagat atagtccaat ttatcttttt atgttttcgt caatctgatt    62255 tgtgaattat ctatatgaag ttaggaaaaa tcttaatgta cattacaaaa atataatata    62315 tattacattg tattttcttt ttttctactg gaattttatg ctactgaggc tattttttaac   62375 aaatgaacaa ttttgaacaa tttgagggat tgagggaagt atgataatga caaaaaggga    62435 tgaaaaaagg gggtcataga gatgtttttg tgagaaggag ttggtcagtg tattctgatt    62495 tattagggtt tttttttagtt tatctccagat ttgatctatt taaattgttt tagaagatgc  62555 tggtgttttt ctgtgctagc tatgaaattt atgggtaaac tttaagcctt tcctagtcct    62615 tttgttgtct acctaaattc aattaatttc atatggaagg atgtagtaag tgagtaatat    62675 aaatatctaa aattggatgt tgaaaacaa acatacctg ttttttgtaa tagcttgatt      62735 taatgctgag ttctcaaaat cattattaag attttgaact ttcacattca atgtggaaag    62795 aattgagtgt aattacaaaa gatttatttg aaaagttga gttgttaatt tgtgaaatat     62855 gttccattaa actcataata ttttagaaaa atagtaggaa gtaataaagc ttgtttattt    62915 tttatatcat atattcatat aaaatgtcag ttttcctttta aaattacat tttttttttg    62975 gttaattttt ag gca ctt agt  cgg gca ctt tta gaa  ctc cgg gca gaa      63023
              Ala Leu Ser  Arg Ala Leu Leu Glu  Leu Arg Ala Glu
                  1745                          1750 atg  aca gca gct gct gaa  gaa cgt att att tct  gca act tct caa       63068
Met  Thr Ala Ala Ala Glu  Glu Arg Ile Ile Ser  Ala Thr Ser Gln
1755                      1760                 1765
```

| | | |
|---|---|---|
| aaa gag gcc cat ctc aat gtt caa caa atc gtt gat cga cat act<br>Lys Glu Ala His Leu Asn Val Gln Gln Ile Val Asp Arg His Thr<br>1770                               1775                      1780 | | 63113 |
| aga gag cta aag gtgaacatca acacgtgtta atgtaacaaa atttctgata<br>Arg Glu Leu Lys<br>1785 | | 63165 |
| attcctattg gaagagaatt cactatgata tatagtaatt ttgttgatga atagggaatt | | 63225 |
| tataatgcac tgttggtggc tagacataga cacacacatg catttttcaa caataagtct | | 63285 |
| ctttatgata ctcatttact gattatcatc ttggggatta ggaaaggata ggccattatg | | 63345 |
| aactactgtt tctaatgaaa ttaaatttaa gaaatatttt acttaggatt ttttttaaga | | 63405 |
| ctttattatt ttttagagc aatttaggt tcacagcaaa attgagagga aggtacagag | | 63465 |
| atttcctgta tatctcctac cctgaaagtg gtacatttgt taaaattgat gaacctatat | | 63525 |
| tgatacatca taatcaccca aagtccaagt ttacctctat tttagctctt ggtattttac | | 63585 |
| actctgtgtg tttagacaaa tgtataatga tatgtatcca tcattatagt attatacagg | | 63645 |
| gtattttcac tgccctaaaa atcttctgtg cctctcttct tcattccttc ctctgcacct | | 63705 |
| caccaaaccc ctggcaacca gtgatctttt tactgtctcc atagtttcac cttttccaga | | 63765 |
| atatgttata gatggaaaca tacagtgtgt ccccatcatt ctcaccatag gacagctagg | | 63825 |
| aactcctttc tagtggcata catattgtct agtattgtaa gttaccctt tatatcttat | | 63885 |
| ctttgtaaac taggttagaa attacttcaa gtcagagatt tgttctgtac tactcttatg | | 63945 |
| cttcatagtg tttaaaacgt tgtcatatat attgttatat acttgtttgt ttaattaatt | | 64005 |
| cagccaaaat gaaacgtgca tatttgataa aattttgttt gtgggtgttt gttgaagatg | | 64065 |
| aattgcttta cactagttttt ttttttttt ctcaaagtcg acttttttcc tcaaggtaga | | 64125 |
| cttgacatga atatgaaaa atatatgtag tttgtggtta tttttttct cttgtgtact | | 64185 |
| taaaaattca gactgaattt ttcttataat ggtatatttt ctgttttatg ttccttttat | | 64245 |
| cattgatact tcttgaagag tcatgaataa tacctttctt tttctcttat tag aca<br>                                                                                             Thr | | 64301 |
| caa gtt gaa gat tta aat gaa aat ctt tta aaa ttg aaa gaa gca<br>Gln Val Glu Asp Leu Asn Glu Asn Leu Leu Lys Leu Lys Glu Ala<br>1790                               1795                              1800 | | 64346 |
| ctt aaa aca agt aaa aac aga gaa aac tca cta act gat aat ttg<br>Leu Lys Thr Ser Lys Asn Arg Glu Asn Ser Leu Thr Asp Asn Leu<br>1805                               1810                              1815 | | 64391 |
| aat gac tta aat aat gaa ctg caa aag aaa caa aaa gcc tat aat<br>Asn Asp Leu Asn Asn Glu Leu Gln Lys Lys Gln Lys Ala Tyr Asn<br>1820                               1825                              1830 | | 64436 |
| aaa ata ctt aga gag aaa gag gaa att gat caa gag aat gat gaa<br>Lys Ile Leu Arg Glu Lys Glu Glu Ile Asp Gln Glu Asn Asp Glu<br>1835                               1840                              1845 | | 64481 |
| ctg aaa agg caa att aaa aga cta acc agt gga tta cag gtaatttat<br>Leu Lys Arg Gln Ile Lys Arg Leu Thr Ser Gly Leu Gln<br>1850                               1855                              1860 | | 64530 |
| atttaactct gataatgtct gatttacaat atagaggtag tagttatttt ctactttatc | | 64590 |
| attttatcta tggtatttgt taaaactgac tttcaaatca cttgattaa tgtaattaat | | 64650 |
| ttcttttgtg acttctattg tgtttatagt tctagagtag catattagta tgttgtatta | | 64710 |
| aaatgcagaa gcagctacca gattatctta tgtattaagt gtcatttaga aagtatggtc | | 64770 |
| agtgatagct tcagaaagtt gctattatat aattgaaata tttactgtct attttgtttt | | 64830 |

```
acatttattt gtaaaaatat aaagttacat tttattttt ag ggc aaa ccc ctg        64884
                                              Gly Lys Pro Leu
                                                      1865 aca gat aat aaa  caa agt cta att  gaa gaa ctc caa agg aaa  gtt       64929
Thr Asp Asn Lys  Gln Ser Leu Ile  Glu Glu Leu Gln Arg Lys  Val
            1870                      1875              1880 aaa aaa cta gag  aac caa tta gag  gga aag gtg gag gaa  gta gac       64974
Lys Lys Leu Glu  Asn Gln Leu Glu  Gly Lys Val Glu Glu  Val Asp
            1885                      1890               1895 cta aaa cct atg  aaa gaa aag gtatgtgaag aaacatactg acttatatgc        65025
Leu Lys Pro Met  Lys Glu Lys
            1900 ttaaggtagt gacagagtaa gttaaataca tagctgatta acagttaata tactgcctta    65085 atttgatgac ctggctgtat taattctgta ttaattttga ggactataag cagtattgaa    65145 taacgtagaa aagtctaagt ttctgttctg taggaattta gagtctactt gaggagatac    65205 ctataatgta actcttattt ggaaattact acatcaattt cattcatctt tctgacatta    65265 gagtacctct gaagttcctt cacaccttaa catattcaac tgtgtatcat ttctctccaa    65325 agtaatcatt tacacaggtt ggtgcttttg acttttggga cagaaagata gacattttaa    65385 gatacccac tttgacccaa ataggtcctt tttaatcctt caggagacta ggctgttatt     65445 tcagatagca aagttatttg gaatatcttc agtatttgca gtaataatca gtaaccaatc    65505 tgctcataga ttaattctgt gggagaaatt gcttaaaatt ttatagttca tagtaaactg    65565 ttttgtaata aaaattactg attgaaataa ccccaaaaaa aactaaaatt ggctaaaatg    65625 cgtgtaatta aatttgttat ggacaataaa ttggagataa cttgttggta acattcaaaa    65685 tatcgaaagt gaactgggaa atgttgatgt tagcagtaat atttgccatt gaagaaaatc    65745 agtatggagg agctatggtt aggaaaattt ttattataaa atttacccag aaaatatttta   65805 atgtctataa aataatttca atcacatgaa aatggaaaag aaaattctgt ctttaaaggc    65865 attgaataga aaataggtaa tggaattcaa atttcttaat agagtatgct cccaaaatta    65925 ttttctatga aaattcatta atgtcagtgt aatttattga cactatttgc gtggagtcac    65985 aacatgcttg ctgtcagaag ctttgctggt gaaaactgta agatcaaagt gtccttaatc    66045 ttttggattt ccatctttct aactccctaa ttggggatag gcctgatctt atccctaaat    66105 ggggataggt tagaaactgg tatgtttgtt cctaactggt gtgtttctat accagtttct    66165 aacctgattc ctatcagaat gttttaagag ccttgtggct ttgcctggac tcttctatgc    66225 tacagtttat ttagtttatt tattcagttt attcctcctt aaagtgggaa taatactatc    66285 tgtattgcca gtttctcagg attattttac ataaaatgat atgatatgcg gaagtctttt    66345 gtaagccatc acatccatag cagtataaga tattactact aactagaaag agaaaacagg    66405 ggtctatgcc cagtattaaa aattggcattc aggaatctag tgagaatatt ttttcaggtt    66465 cattgcttgg gcatttctaa tttatactca agaaatgctt tcatattgtt tggaaatttt    66525 agtacccttt tctctgtaaa cagaatttgt agtctaccta tgtaacaaaa cccacccctg    66585 tgccttgcat ttcattctcc ttagcattta ttactatctt aacatactag acatgtactt    66645 gtcttttgtt catcttttt tttctttt ttattagacc ataaactttg atggcaggaa       66705 ctttgcctat tttatttatt attgtattcc cagcacctag aacaatcgct ggcacatagt    66765 agatgctcag tatttgttga atgaatataa attttaaat gttataataa tattattctg     66825 aaatctatgc atacgaagct tttggtacag aaaacatgaa aagagaacta ctgccttatc    66885 atccagtctt cttccctctt ctcattcagt ctagaacata acctgttttg gaaaaagttc    66945
```

-continued

```
tcaaaccata tgtttatctt gccctcaaac cataacaaca atcaatgcaa aagacttctg    67005 tgaccccag aatatgtggg gatttctcca catcagcaag caagcagttg gttttgtagc    67065
agacaccaac tgggtgtcgt ccaattcaat tcatcatcta cctggagata gtgtcagatc    67125
ccacagatat cttacttcga tcaaatcaca agtccaggcc tccgtgactt ccgaagttcc    67185
cacatcccca gcccccagct ttgggtttga ttaatttcct ggagtggctc acagaactca    67245
gggaaacatt tacttacatt taccagttta aataaaggt tattacaaag gatacaggtt    67305
aagagatgtg taagaagaga tatgggggaa ggggtgtgga ccttccatgc ctttctgggg    67365
tgccaccttc ctctagaaac ctccacatgt tcagttctcc agaacctctc tgaacccagt    67425
cctcttggtt tttagggaag cttcatgaca tcagtatttc ttctcctagg gtatgggca    67485 ggaccccctc gtattagggt tttaagaccc acagtcagaa aggcagggga agattacagt    67545
cctgccttag ggcaggtgaa aggaggatgg gagaaggtca gagagactct tttctgaggt    67605
gtgctcggaa ggcctaacac actcaatatt ataactaaag atgaggacaa gggctatgag    67665
agttataagc caggaaccat ggaaaaaagc ctatatgtaa taacaccaca atacccatgg    67725
taccattcac gtttgttgtt tttctgtttt tcaattgttc tttcagtctt ggttccctta    67785
atcttaattt agcaagtaat gccaggtggg ataaaattgc ccaaacccaa caaagtactg    67845
tgtgctgcag gattatttaa tgacatacct tatgtccccc actagtattt acatttctgg    67905
gagtacagaa aaattcttgt acatatttca gaaaaaatga aattaataac tatcaaccac    67965
ttagtgaagt ttttactttt tttttgaga tggagtttta ttcttgtcac ccaggctgga    68025
gtgcaatggc gcaatctcag ctcactgcaa cctccgcctc ctgggttcaa gtgattctcc    68085
tgcatcaacc tcccaagtag ctgggattac aggtgcctgg caccacgact ggctaatttt    68145
tgaattttta gtaaagatgg ggtttcacca tgttggccag gctagtctca aactcctgac    68205
ctcaggtgat ctgcccgcct tggcccccca aagtgctgga ttacaggtat gagccaccac    68265
acccagactg aagtttttac attttttaaa gggcacttat tagctgaatt aaataaggta    68325
aaaaattgac tagtattaga gacaagaatt ggagaatata gttctctagt attcgagaaa    68385
gtcgttttga taggacaact aatccttagtg agaatttggc tttatttcat attttttaa    68445 tttttttgaga tgacgtctta ctatgttgcc ctggctggtc tttgaactct gggctcaaac    68505
aatcttcctg cctcggcctc ccaaagtgct gagattataa gcatgagcca tctccccagg    68565
aatttgactt taaaccatgg ttctcaaccc tttcagattc aacattccct ttaataaaaa    68625
atataatgtt tcataatttc ccctttacta ttataattga aatgcatagt taacataaac    68685
tctacctact tacataattt caaaaatgtc attatgaatg tcctaaatga aatatatagg    68745
gggaacataa aaggaatatt catatttcaa catgtaaatg ctttggcatg actccattgg    68805
aaaatataat gaactagtca tgtgcttgca ccttcattaa tgtgagttca aagctacgat    68865
tgcagactga cacaaatgtg ttctattggc aactgatggg tcatgatggt attgccattt    68925
gtaatttgat ttccaaaatg gtaaacaaat tgttggtgca gttctcagca aaacaatgtc    68985
tataatctta ccttttataa gactgttgta ttcctagaaa acttagtgta tagtaaaacc    69045
attaaaaaat tacttagtgt gaatatgtta gttggagata aattcttagc tcagaccagt    69105
gtaagcagaa ttttttactg tattaatatc cagtagaaca tttgaaagtt gttcagtgca    69165
tgagactatt ctgcattgga taggctttct ttggctcctt tatcatagtt ataataaacc    69225
atgacaccta cccctgaaat gccctaattc ccttccgttt cttttctttt tttcttttta    69285
gcacttaaaa ctagctaact tactacaaaa tagatttaga tttatttctt gttttgttat    69345
```

```
ctgtatcgtt tgctcccttc tccccaatct atctaaccaa ctagtataaa ctagatagta    69405
agattcatga agatacactt ttttatctga ttttattcat ttgttctatt cctattgcct    69465
ctagagtagt acttggcaca tggttagcac taaataagta cctgtcaaat gagtgaagta    69525
atgtgcattg aagacttgaa ggggctctga tgctaggaaa ttgtcatggg ataatagatg    69585
aggttggtcg tttgtacaga ggattcttgt tagaagctta ctctagtcat gattgtatta    69645
gaatcttcat ttaaaggctc ctgaagggtg ttggcattag tcagaactgt ctcccagaat    69705
tttatttgtc ttgtgataga ataaagcata gttagcctaa agagcagttt tcctaatagc    69765
tcggcatgcc caaagattct aggagttata caggttgaac atctaatcca aaaatctgaa    69825
atgctccaag atacaaaatt ttttgagcac caatatgatg ccacaagtgg aaaattctga    69885
tgtgacctca tatgatgagt cacagtcaaa acacagtcaa aactttgttt catgtacaaa    69945
attattaaaa aatattgtat aatactacct ccaagctatg tgtagaaggt gtatgtgaaa    70005
cataagtgaa ttttgtgttt ggacttggga cccatcccta agatatctca ttatgtatat    70065
gcaaatattc caaaaatatt ttttaaaaaa atccaaattc taaaacacgg ctggttccaa    70125
gcgtttcgta agggatactc aacctgtata gcaaaatgaa catatttaca tattctctag    70185
gaaatattag tttacaattt ttctaggcaa attataattg ataaatcata aagaaaattt    70245
aaaataacac tggtaatttt cctacctcct tcgttattgt tacag aat gct aaa       70299
                                                  Asn Ala Lys
                                                          1905 gaa gaa tta att agg tgg gaa gaa ggt aaa aag tgg caa gcc aaa          70344
Glu Glu Leu Ile Arg Trp Glu Glu Gly Lys Lys Trp Gln Ala Lys
         1910                1915                1920 ata gaa gga att cga aac aag tta aaa gag aaa gag ggg gaa gtc          70389
Ile Glu Gly Ile Arg Asn Lys Leu Lys Glu Lys Glu Gly Glu Val
         1925                1930                1935 ttt act tta aca aag cag ttg aat act ttg aag gat ctt ttt gcc          70434
Phe Thr Leu Thr Lys Gln Leu Asn Thr Leu Lys Asp Leu Phe Ala
         1940                1945                1950 aa  gtgagtttaa atatcattat aaaactaatt atgtgtaaaa tcctttagtg           70486
Lys acctggaaat tatatagctt tatcatagtt gataaatga gaaatggtct agtttaaatg     70546
atcatttatt atctatgatt tacttacttt ttattttctt taaaatctgt tttaaatata    70606
ttgtaacaat tatagatgga ttttcctgtg atctcgttgt aaattagctt atgacaaata    70666
tagggtgtta caattattgt aatttggttt ggtaatgagt atgcaattga aaagccaaac    70726
actgaatggt atatttcatg attctatatt aaattccaca g a gcc gat aaa gag      70780
                                              Ala Asp Lys Glu
                                                      1955 aaa ctt act ttg cag agg aaa cta aaa aca act ggc atg act gtt          70825
Lys Leu Thr Leu Gln Arg Lys Leu Lys Thr Thr Gly Met Thr Val
         1960                1965                1970 gat cag gtt ttg gga ata cga gct ttg gag tca gaa aaa gaa ttg          70870
Asp Gln Val Leu Gly Ile Arg Ala Leu Glu Ser Glu Lys Glu Leu
         1975                1980                1985 gaa gaa tta aaa aag aga aat ctt gac tta gaa aat gat ata ttg          70915
Glu Glu Leu Lys Lys Arg Asn Leu Asp Leu Glu Asn Asp Ile Leu
         1990                1995                2000 tat atg ag  gtaagctatt atgtggaaat gtgccaccca ttgtaatgaa              70963
Tyr Met Arg aaactggttg accctagaa attgaaataa taaatgtgtg ttgtcttaag cttgggttat     71023
gttttctttt cccatgtgaa ttgagatatt cctggttctt catatgccac ataattttgg    71083
```

```
tgtattttg atcttttgaa tattatattg tgagactctg gttcttgttt aaattctatg   71143
ggaaaatgta gatacttttg ttttagcatg caatcggtct aattaggttc aggccacaag   71203
ttccaacctc atttcttggg ctgtggttcc atttttcaaa gccttttcaa tactcttcag   71263
atctgtcctg cctgtgtacc tcacaatagg tgatctggta tgtgagctat gtaccattag   71323
ttcagttctt agaaactttg gtattctgat taggatcgat ccatacattt gcagctcaag   71383
agtgagccca gaagttcata aacaaccttta tagggtccct ttcttgagct cctccctctt   71443
tgccatctct ctgatacttt gtttccctag ggatttccat ttgggctttt agttacccag   71503
tgatgccatg tacttcagga attgcacact tctgcagcca agcaagcaag aggagagtag   71563
aaagaggaag aaaaaaacga cttttacctt accctcttag tatcatagct ctaccaattg   71623
gagatttccc tcccaaaaaa tattagcttc tgtgagttcc cattgcagcc tctattacca   71683
ctgctatggg atggcttaag ggttggggca tgaaagaaca gatagaagaa aaaaaaagtg   71743
aggtgttttc atattgtctc ttgagtgtta aaagattccc tttctctttta ctcgagctag   71803 aattagaagg tttacctgga gctctctctg tcagtgcaga cacccatctt caggtttcaa   71863
ataatgttgt cttcagggca ggcagtaaca gaataaaaga aaaggtaaat tcatcacctg   71923
tttgctgcta ctttaagtcc tggtattcta ttgtaatctg ccttctactc ctttgcaaag   71983
tcctcaaatg gttgctccat gcatttagga gagagaagat tgaatgtatt tactccattg   72043
tacctggaac cagatgccct tgccctgcat cacccccatgt catttcttag cagagccttt   72103
gagatttttg tgtgtgtgtg ctttacaatc tctttccaag ttatatcttc tgatacagtc   72163
atggtcgtga aaagcaaaat aaaatcatgt gttaacattt aaaactttt aatttattc    72223 tgacaacagc taaaactatt taatcttctg tttcgctcat ttcttccaag gtaaacttca   72283
gttggtttta cgtgatttgc tatttcttct tctttgcatt tacaaatgat ctgtgatcat   72343
attactgatc tttgtaaagg gctaatatct acctgcaaca tttggatatg acagtattta   72403 cccttttgtaa atacacattt tctatttatc ttcaaaaatt accattcatt agtctgtgtt   72463
aatgtctgtt tactattgtg tcattatgaa tgtgatgtga acatacgaag ttgaacttat   72523
ttaaacgaac actctcatga gcttctaatc cacattcctt cctttccctt ctaagttacc   72583
atttcttaaa aatctttttag aagtttcctt gatagggaaa acacaaatta ttgaggaatt   72643 tttcttctc ttgacatctg tttatagtta ctctcttgtt ccagcagtgg atatttcccc    72703
tccatgtttt tctttgtcta aacatatgtt caaaacaaaa cacttttatt cttctttgca   72763
ggttttacaa ggatcaactt ttagttttga aacctgctat tacttttaga ggccattttt   72823
tttttctcta ataatgtgag ttcatgcggg ctgaagtaat tggaatactt tatagaaaag   72883
attgaatttg tcttctctct gaactctagt ttgaatttct aaattttatg aatcatctag   72943
atattaaaga ggagggggcat atcaaagagg agaaccctag cagagataag aggcaagagt  73003
aaatgtttca tgtatgggta agagtggatt tgtatttacc taagtaaagg tagaccctgg   73063
acaataaggt tggatagatg tggaggtggc aaaccatgga gggtcttgta ggtcaagtgg   73123 atgttttag acttgaagtg ttaaattatt atctgaaatc attaagagtc ttttagatc     73183 cttgagcttc ttgagaagac catggatatt atgcagttat tatataatgt tttaaaatag   73243
taagtatttt agtttaactg tcttatgtaa ttccatataa atggatgcat gttctttaaa   73303
aatgttaatg tatttcagta aatcaaaata tactttttga ctcatcattt aaaggaggcc   73363
ttcagtgaat gctctgtaga ggattatttt ataatactaa ttttgatatc ctaatttatt   73423
```

| | |
|---|---|
| tgttataaag tttagaaggt ttgaagaatt taaaatatag tgttaataaa cacactgaac | 73483 |
| ttttctttt ttatcttgta tttttatata gtacaacaga aaaaagatga aatgtgaata | 73543 |
| gtaaagagtc tgtgattgtt gttcatag g gcc cac caa gct ctt cct cga<br>                                                       Ala His Gln Ala Leu Pro Arg<br>                                                       2005                   2010 | 73593 |
| gat tct gtt gta gaa gat tta cat tta caa aat aga tac ctc caa<br>Asp Ser Val Val Glu Asp Leu His Leu Gln Asn Arg Tyr Leu Gln<br>            2015                   2020                   2025 | 73638 |
| gaa aaa ctt cat gct tta gaa aaa cag ttt tca aag gat aca tat<br>Glu Lys Leu His Ala Leu Glu Lys Gln Phe Ser Lys Asp Thr Tyr<br>            2030                   2035                   2040 | 73683 |
| tct aag cct tca gtaagtgtat atctttatt attttttct tttttccatg<br>Ser Lys Pro Ser<br>            2045 | 73735 |
| ttaaaatgca tgaaagtgaa atcaacttct ttcttaatct ggccaaaagc attacatctt | 73795 |
| tctcattaat agtaatacag taaattcaac tttattttt aacaggtagt gatgtgtaat | 73855 |
| aatttattta atccttttta acataataac agtaaactta agattcttaa gcttttcata | 73915 |
| aagctcataa atgatttcta gaatttttaa atatgtagtt atcattatgt attttgctgt | 73975 |
| agcagcagta tacagttaaa taaaatagga aaacatgttc caagactgtt ttcattcaaa | 74035 |
| tatttatgct atatttttag cttataaaaa ctcattaatc attaatgtaa aattatttgt | 74095 |
| tggattttt aaatatttag tgtattattt ttgtttcttt tttctttcca tgtttcttca | 74155 |
| ttcttccacc ttaagcagaa tcaggtgtgt gacacaacta tgttttctat ccttgttacc | 74215 |
| attattaata aatacaaggg catgatattt ttcacaaaag aaaactttg ttcagaacca | 74275 |
| aaaaagatca tggcaacagt cagaattaaa aatggtaaaa gactaggtgc caaagatgac | 74335 |
| ttacataatt gggtacctag aaatattcta tggtattaca gtaatgatga aaaatacaaa | 74395 |
| ttagaacaca ttttagatcc tattgagtta aataaatcag agtcaagacc aaacaataaa | 74455 |
| taaagtcaat ttacgtcaac aaatggtaag ttggcagatt ttaactccct ttttgaaaat | 74515 |
| gaaccatgat cctaaggttg gtaaaattaa tcaagaatgt tgtcaaaatg ataaagataa | 74575 |
| aaatgaggaa gagaataaga taggcaagag tgagaaagga aagagacaca tagctgaaaa | 74635 |
| tgtgagtcac aacaactaca tagatccgta gaatctgcta tggaggactg tgattatgtg | 74695 |
| acagttgctg atgccgtggc ttagtgagct gagggtgatg cacaggcagg cgatgtaact | 74755 |
| gatgcgtcag tccagccaag aaaggacgcg tccctggttt ggctacgtgg ccgtccttta | 74815 |
| tttctttgtt aactgaattt tcttatagta agtagcttac gtacatatat agtgcaaatg | 74875 |
| ggaaagtgtg taagatttag aaaaagcatt aactattagt aaactttatc ttaagctcta | 74935 |
| acttttgatt agttcctaca aaattagtg aatatgcatt ttctaattta gtgcttttt | 74995 |
| ttttttaca attggtgttc acttaatgtt atattagata aatgaatagc aaaaataagg | 75055 |
| tactttagag ttgattgttt tgccttacaa acttctaatc catccagctg tatttagaag | 75115 |
| taagatctca ctacagcgaa ttatatcagt aaaatttgt tacagtgttg tgcagtgtcc | 75175 |
| taagatgtat actaagttcc ttcagtggct ttttttgcca tgtttataa cagataattt | 75235 |
| tgttataatg agaaaaggaa acttggatgt gttgctgtct atattgtgtt aggctcaggc | 75295 |
| aggatgctgt ggcttactca tttaatcact ttgggaggca ggggcaggaa gattgcttga | 75355 |
| ggccaagagt ttgagatcag cttgggcagc atagccagac cctgtctcta caaaaaattt | 75415 |
| agacagatgt ggtggaacac atttgtagtc ctagctatta gggaggctgt ggtgggagga | 75475 |
| tcatttgagc ccaggagttt gatgttacat tgccctattg cactccagac tgggcaacag | 75535 |

```
agtgagacct gtctctaaaa taataataat gataatgata aatggtgtta ggctctgtgc    75595
ctaagtatat ttttcacata ggctgggtaa agtggctcat gcctgcaatc ccagcacttt    75655
gggaggccaa ggcagcagga gcatttgagg ccaggagtca aagaccagcc ttgagagacc    75715
ccatctctac cagaaaaaaa aaaaaaaaga aacaattagc tgggtgtgat tgtgcacacc    75775
tgtagtccta gctactcggg aggcagaggt gggcagatca cttgagccca ggagtttgag    75835
gttatagtga gctaagattg tgccactgca ctccagactg gcaacagag caagactgtc     75895 tcaaacaaaa acaaacaaac aaaaagcact ttgcagaata tcagtctaac tctacagttt    75955
atggactttt tatgtacgta ctacttttgg ctagcttaca ttgagataca gaataaaagt    76015
ttgttcatag catttatcgt ttttttcttt atactgtcca cctgagatat tccagtcacc    76075
taagtcatgg aaacatcaac taaaattaaa tatctatgtt aagagaaaat ggctgaaagt    76135
gatttaattc ataacacttt ttttcacatg ctaataaata agagtttgag acttccacta    76195
ggcattatct ctaactccta tccactaaga atttgatttt aagtagttga tggcttttaa    76255
ccggattatt cttctgtaag agtttggaag tctcgtgaag ttcgttatac aagaattctg    76315
tttacaagag agcattacat tagaatttgt ttttcagaaa tttggactat ctcaacgaat    76375
acctttagtt ttattatttc aaaatgcaag ggaaaaaatg agccataatc actaatagta    76435
actgcatcat attttagtga gaaatgtgtt aaaaatatcc tcatgtgaga tcttccttag    76495
atagaattac cctctactct aatatttaat atattttata tctaccaatc agtgatatta    76555
ataggtgttt atcatttgct gaatcaaata ggtacaacag aagacaggaa gtttgggaga    76615
tagaagagct cagggacagg aaatcacaga tgtccatatc tgaaataacc ttaaaagtta    76675
tcctgtctaa tgccttcact tataaactgt agtggtagaa tttgcctagt attaacctaa    76735
tagtggtaga tttgaatgta tacttgggct ttcttattaa gtggaaatgt attcctgtga    76795
tttacatata tcaacaaaaa tgtttgtctt ctttttttg ctacgacata tgtgcatgtg      76855
cacacacatc tcctcaaaca aaaatcagat ggacacatgc agtcattgga tctaaaagat    76915
gttataaagt tgtgtataat aggtatttta taataatata ttttaagacc cataatgtcg    76975
gtggagtaac tgactttaca gcccatcaag ccaatagaga gagaaaggag aaaaaaatga    77035
aagttgtgct gaataattaa aaaaaattat ttcctatgat gcttataaca gtcctatgag    77095
gtaggtggta ttctaatttta tagaaaaaat gcatagaaaa atataattaa gcacagttaa   77155
aaaaaataaa gtttagaatg agaagtaaca acataaataa tgacccaatg tagattcagg    77215
tcaaaagaaa tgaaaatata atattaatgg ttttcaaaga gggaaccatt actttagctc    77275
aaagaatgaa ggagggcttt ccgaaggagt aaagaattat ggcagttctt ttgtagccta    77335
gtgtattcat ttgctaaggt ggctgtaaca gactactaca gatttggtgg cttaaacaat    77395
agaaatttat ggtcttagtt ctggagacct agaagtccaa aatcaagaca tcagcagggt    77455
tgatttcctc tgcacaatca gagggaaaga tctttcccaa tcctctctcc ttggcttata    77515
aatgtccatg ttttccctgt ttcttttat catcttcctt ctgtacatgt ctctgtgtct     77575
aaatccccaa attttctctt ttcataagga taccagtcac agtcgaatag ggtttaccct    77635
gaaatctcat tttaacttga atacctctgt aaagacccag tctccaaata aagtcacatt    77695
ctgaggtact ggaaattatg actttaatat ataaatgtgg agggtaaggg gaacacagtt    77755
caacccataa cggttagata acaatcgtgc tttattttgg actagtaaaa ccaccataga    77815
tcagtttaac cattatgaaa ttatacatga aggcattata tgtatggaca ttattaagtc    77875
atacttgctt tgcttccatt gtaattaaaa caaaccatac tacctttgtt ctgcaagttt    77935
```

```
tgtattctaa cttatttatt tttggctttc accagaacac tccgattttc tcatattcct      77995
ttgaggaaaa aaagttacct tttgacagta ttttcttatc cagtatgtct tttatggctt      78055
ttatttatta aactttaaaa atattcctaa tttcatttcc ctgaag att tca gga          78110
                                                  Ile Ser Gly ata gag tca gat gat cat tgt cag aga gaa cag gag ctt cag aag            78155
Ile Glu Ser Asp Asp His Cys Gln Arg Glu Gln Glu Leu Gln Lys
    2050                2055                2060 gaa aac ttg aag ttg tca tct gaa aat att gaa ctg aaa ttt cag            78200
Glu Asn Leu Lys Leu Ser Ser Glu Asn Ile Glu Leu Lys Phe Gln
    2065                2070                2075 ctt gaa caa gca aat aaa gat ttg cca aga tta aag  gtgaatttaa            78246
Leu Glu Gln Ala Asn Lys Asp Leu Pro Arg Leu Lys
    2080                2085                2090 tgttttttat taggaaatct aatgcctaaa actccttcct tagttgttat gtttactttt      78306
attagcttat taagaagtca aaaatgcata ttcctaatat atcatggtga tggtatactt      78366
tatacatttg ctctttagca tttatttgtt gaaggcctac tttatattaa acactcctcc      78426
agatgctggg aaacagcagt caaaaaattc cttatactca taggacttac gttctagtgg      78486
agaagactga caataaacaa gtcactaaat agtatgtcat ctgatgttag tgctaaggag      78546
agaaataaag catgattggt gtaaagagta tggggagaga aagggtgt aactgaaaat        78606 agagtagtaa gggaggtctt ccttaataag atgatatatg aacagagagc taaggagggg     78666
taaaggaagt gagtcataca gatactagaa aaataattac agacaacaga aatagcaagt     78726
tcagatgtcc taaggtggga ggatgcgtgg tatatttcat taaaaattat cacactgtaa     78786
aatataagaa taatttgttt cttttagaaa ttttacttta ttctgatatt aataatgatt     78846
ttttaatctt tggttttcca agtcttaccc tatttatggg aatctttttt ttcttttggc     78906
tagctaattg cttcagtttt gttttctaat ctagaatgtt agcaatctgt taattccact     78966
ggtaatgata tagttaagct atgtcttgct tctcacactt tatttattta tttactcagg     79026
gcactaatct gccatttttt cgcactttt ttcctttttt tttttttgg tactgcttct       79086 tattctggtt tttacattga tagaaccaat gttagacgtt catttgcctt ttgctgtgta     79146
tatttgggta aggatctata tgtgcaatat atgggacagt taaaatcaga attctaaatt     79206
tgtattattg catcaggcaa taatgtggga aataccttga catttcatat acacaatatt     79266
cttgtattaa tttaacgtct tagttcaaaa tcttccttgt taatatagag accctattat     79326
ttggtttggc aatacagttg aagagattga tggttcttat gaattgtttg ccttttcttt     79386
tcaatggctg tagctatgtt aaattattac atgtttgctt gttatcttc ag aat caa      79444
                                                         Asn Gln gtc aga gat ttg aag gaa atg tgt gaa ttt ctt aag aaa gaa aaa           79489
Val Arg Asp Leu Lys Glu Met Cys Glu Phe Leu Lys Lys Glu Lys
    2095                2100                2105 gca gaa gtt cag cgg aaa ctt ggc cat gtt aga ggg gtatgtgaga            79535
Ala Glu Val Gln Arg Lys Leu Gly His Val Arg Gly
    2110                2115 atttaccata catttgtttt ggtttcagca gtgataagcc agaaatgaaa agtttagata     79595
tgttgtaaaa gtactgatat gcctctacaa gtgccctgta gttcagtgt ttattctgca      79655 tctgtaatat aaaacagtaa gcatttctat gtgtctcaaa gtatttatc atctgttata     79715 ccttacatac tttcatctct cttttttattg aatatgcctc catacctgta aaacatttaa    79775
cttccaggaa tccttttgtt tatggaggta actgctaact ggtccttggt ccaatgctgc    79835
cattttgtaa ccatttgtta tgatatcttc ccagcttggt ataatgtttt ataattacat    79895
```

```
tgttcctccc cctcttttt tgtgttcttg taattttctc cctatgttat tttgtattca    79955
ttttatataa tgaataaatg ttgcttatga ggtcaaggcc aaagacttaa gctcctgttg    80015
atttcatgtt gctgagtgtc ataaatggaa gcaatcataa tgcagagtca ttctggtagt    80075
aatattaaat atatgatgga ttcagtgaaa atattatgtg ttattagaaa atattcaga     80135 acaggccggg ggcagtggct cacacctgta atcccagcaa tttgggaggc cgaggcgggc    80195
agatcactgg aagtcaggag ttcaagacca gcctggccga catggtgaaa ccccatctct    80255
actaaaaata tgaaaattag ctgggcatgg tggctcatgc ctgtaatcct agctactcag    80315
gaggttgagg caggagaatt gcttgaacct ggcaggcgga ggttacagtg agccatggtc    80375
acacaactgt actccagcct gggcgacaga gcgagactcc atcttttaaa acaaaaaaaa    80435
aaaaggaaaa atattcagaa cagtatcttg ctggcagcaa catttgtttc atcaatgaaa    80495
atatgtgtta atttgacctt ttctatctaa gttaattatg aaagtgcata ctaaaatgat    80555
gtaaagtttt atatttcagg attattctta ttcatggatg attaactaaa atgcaaaaag    80615
aaattaagca tactgtttgg ctaaactgtt aaaaattatt tttatttta  atgataagca    80675 gttaaactta ttaagtgatg actcatctct gctgatatat ttatgcaagg ttttttattt    80735
cagataactc ttctatttat attaaacaga aactgtattt ctaagcaata gcatttctta    80795
gagaaaattg cctctattat gttgcaatta aatttaatt actcatgagc tctttaaaga    80855
cacaatttct cttgtgtggt tttatttcat ataagaaaa actctgatat actggagaga    80915
acattagcta aatagactat ttagacttaa tcattttgat cagacatcaa ggctagacta    80975
tttaagctgt tacttattag ctgcatgatt ttaggaatgt caaatttcct aagtcttggt    81035
tttcttgtat ttaaaatgga aattataatt cctatctcat agaattgttt taaggatgaa    81095
ttgaattaat acagttttga cttcaaatat taggaattat tgagtataat aagcctgttg    81155
tattgttggt acttcgtatt atacttacta aaatatttga ttaaagattt aacatattct    81215
```

| ttcgtag tct ggt aga agt gga aag aca atc cca gaa ctg gaa aaa | 81261 |
|---|---|
| Ser Gly Arg Ser Gly Lys Thr Ile Pro Glu Leu Glu Lys | |
| 2120 2125 2130 | |
| acc att ggt tta atg aaa aaa gta gtt gaa aaa gtc cag aga gaa | 81306 |
| Thr Ile Gly Leu Met Lys Lys Val Val Glu Lys Val Gln Arg Glu | |
| 2135 2140 2145 | |
| aat gaa cag ttg aaa aaa gca tca gga ata ttg act agt gaa aaa | 81351 |
| Asn Glu Gln Leu Lys Lys Ala Ser Gly Ile Leu Thr Ser Glu Lys | |
| 2150 2155 2160 | |
| atg gct aat att gag cag gaa aat gaa aaa ttg aag gtaattttt | 81397 |
| Met Ala Asn Ile Glu Gln Glu Asn Glu Lys Leu Lys | |
| 2165 2170 | |

```
ttaatgtgat cattttagg ggaatatttt acgttttgtt actatttagg aaaatttcaa    81457
atatgctcat tactatataa aatggcttta atgaatacaa tacatatttt ataaatatag    81517
aaaaaaactt atgagaggca aggctaaggg ttatagagta ggtctacctg atctttcttg    81577
ttatttcaag accaatactt ttcacttttc tctctgacag catagattaa ttacctgtgt    81637
ctctcttttt tttttctttt gagatggagt actgctttgt cacccaggct ggaatgcagt    81697
ggtgcaatct tgactcactg caagctctgc ctcccgggtt catgccattc tcctgcctca    81757
gcctccccca gtagctggga ctacaggtgc ccaccaccac gcctggctaa cttttcgtat    81817
ttttagtaga gatggggttt caccatgtta accaggactg tctcgatctc ctgacctcgt    81877
gatccgccca ctgcggcctc tgtgtctctt tgtgaaaata cagatgccca agctcccatc    81937
cctgaaattg atttaattat tttagggtgg gtcctgacac agatatgtat gttgttgtta    81997
```

```
ttttaagtca tcaatttatt ctaatatgta gccaacgttg ggaacttcgt tctcactaat    82057
attcaaatga agactttaat tctaatcata tcaaatatgg tttctaaaac tactttgaag    82117
atttatgagt ttataagatt atcttttatt tccttgtttt gataatgtat actttttatt    82177
```

| ttg ttt gttt  | ttt tac tag | gct  | gaa  | tta  | gaa  | aaa  | ctt  | aaa  | gct  | cat  | ctt  | 82226 |
|---|---|---|---|---|---|---|---|---|---|---|---|---|
| | | Ala | Glu | Leu | Glu | Lys | Leu | Lys | Ala | His | Leu | |
| | | 2175 | | | | | 2180 | | | | | |

| ggg | cat | cag | ttg | agc | atg | cac | tat | gaa | tcc | aag | acc | aaa | ggc | aca | 82271 |
|---|---|---|---|---|---|---|---|---|---|---|---|---|---|---|---|
| Gly | His | Gln | Leu | Ser | Met | His | Tyr | Glu | Ser | Lys | Thr | Lys | Gly | Thr | |
| 2185 | | | | | 2190 | | | | | 2195 | | | | | |

| gaa | aaa | att | att | gct | gaa | aat | gaa | agg | ctt | cgt | aaa | gaa | ctt | aaa | 82316 |
|---|---|---|---|---|---|---|---|---|---|---|---|---|---|---|---|
| Glu | Lys | Ile | Ile | Ala | Glu | Asn | Glu | Arg | Leu | Arg | Lys | Glu | Leu | Lys | |
| 2200 | | | | | 2205 | | | | | 2210 | | | | | |

| aaa | gtatgacttt tatgactgat tataactttt gatttttatt ttacttaata | 82369 |
|---|---|---|
| Lys | | |
| 2215 | | |

```
cctcttggaa aaactggaag tagatccttg atgagagtgt ctgtaaaggt agatattaag    82429
agattgagga attgtgtttc tatgcctgct gtcatcacat tccaccatga aaacattga     82489 taataaaagt taatacattt aggctgggca cggtggctca cgcctgtaat cccagcactt    82549
tgggaggcca aggcgggtgg atcacgaggt caggagatcg agaccatcct ggctaacacg    82609
gtgaaacccc gtctctacta aaaatacaaa aaattagccg ggcgtggtgg cgggcgcctg    82669
tagtcccagc tactcgggaa gctgaggcag gagaatcgct tgaacccggg aggcagaggt    82729
tgcagtgagc cgagatcgca ccactacact ccagcctggg caacagagcg agactccatc    82789
tcaaacaaac aaaaaaaaga aatgatctac gttgcttaca cataccttat gcttatagct    82849
aggtctcgta agcattagga agtcaaaaca aagaatcttt tacatgtgta aaggtataaa    82909
ctatcccatt tttctaaaaa tatagaggaa caaagtgtca aatttaaagt aatcactagt    82969
aactaaatat attcctctga cctcattttc gtgatctgtt gttctaatta ttattggcca    83029
tattgctgct ttaaaggaga gatgttgaat ttgttgaaat tttaatcagc atttagagcc    83089
ccaggttatt tttgtttttcc aatttgtaat gataatttttg aatacactga atctatgaga   83149
```

| acagtattat gttttctcat aaaatactaa ttagcattta atgatag | gaa | act | gat | 83205 |
|---|---|---|---|---|
| | Glu | Thr | Asp | |

| gct | gca | gag | aaa | tta | cgg | ata | gca | aag | aat | aat | tta | gag | ata | tta | 83250 |
|---|---|---|---|---|---|---|---|---|---|---|---|---|---|---|---|
| Ala | Ala | Glu | Lys | Leu | Arg | Ile | Ala | Lys | Asn | Asn | Leu | Glu | Ile | Leu | |
| 2220 | | | | | 2225 | | | | | 2230 | | | | | |

| aat | gag | aag | atg | aca | gtt | caa | cta | gaa | gag | act | ggt | aag | aga | ttg | 83295 |
|---|---|---|---|---|---|---|---|---|---|---|---|---|---|---|---|
| Asn | Glu | Lys | Met | Thr | Val | Gln | Leu | Glu | Glu | Thr | Gly | Lys | Arg | Leu | |
| 2235 | | | | | 2240 | | | | | 2245 | | | | | |

| cag | ttt | gca | gaa | agc | aga | ggt | cca | cag | ctt | gaa | ggt | gct | gac | agt | 83340 |
|---|---|---|---|---|---|---|---|---|---|---|---|---|---|---|---|
| Gln | Phe | Ala | Glu | Ser | Arg | Gly | Pro | Gln | Leu | Glu | Gly | Ala | Asp | Ser | |
| 2250 | | | | | 2255 | | | | | 2260 | | | | | |

| aag | agc | tgg | aaa | tcc | att | gtg | gtt | aca | ag | gtaggaacag agttttaaac | 83389 |
|---|---|---|---|---|---|---|---|---|---|---|---|
| Lys | Ser | Trp | Lys | Ser | Ile | Val | Val | Thr | Arg | | |
| 2265 | | | | | 2270 | | | | | | |

```
ttgtacaaag tttaatcatt tcaaattttg gcattgtttt aaaagacaac actattctgg    83449
ataacctggt ttcttcctga tgaacagttt gttttggttgt tgtttaaaca taatactttt   83509
tttctgttgt agtattgttg gagactttt cttccttgaa atgtttaact tgtttaacct     83569
tgtttgggtg gcagggcatg gaacagtgta gagctgggc tgggcgaagg agttggagct    83629
gtgtgtgcgt catgaagctg tcatcagcta tgagcctggg ctgaggctgc tcagcttctc    83689
ctgggtgcta ttttctctcca actgcagctt cagcttcttg attgtataat ttgcttcctc    83749
```

```
aagtatgagc caggaataat tgagctgtct tgtcacaatg tgtggcatac tggatctagg   83809
ctgtgctgca atgctttag agttatatcc tgggcaactt tctcttcaga tagccccaag   83869
agatgaattc agcaccagct ttgatgtttt actagcttct gctttctggt acttgatttt   83929
ctcccacccc gaacacatgg gattccaacc tgtgaaacta attttttgtgg ctatgaaaga   83989 ggtagtggta gtttatgagt aaacattcag tctgttgcca ctatcatcat gtgtggttca   84049
tcatgactgt gatgagtagg taaaaggctc tttgtgtcat tctcatttcc aattttaagc   84109
agctgcttca aggagtctgg aagtcattga ccagtgggat cctgcctgtg tcttttccca   84169
ttaaagccat cctgtatgaa gtggtatcct ttaccatcta gcacatctgc cgcccccatt   84229
tcaaaaggca tactcatctt tatctcaaca ttctcataca gttccttatg tccatgcacc   84289
tccaatgtcc cctttgatgt ctttgaggtt ttcatcttcc atgtctgcta tttggaatgg   84349
tcttgatggg aggcaagata gtgatcacta caactaggat gggagtctta gtaccgtgag   84409
gctacagcaa gtcccacaga gggcctgctg cactgtactt gcctctgtca accaagtcta   84469
aggagaaaga ttaagcaggc atattaaagg acagcccaga tggacatgaa gtcctggagg   84529
aggccttggt tcctgtccta atactaaacc tagagtaccc agaatccaca cttctccact   84589
ctagctctca cttttcccat ctacacactg ggaaaaatta ttctgtcaga aagccagtgt   84649
caaggtgaga acaaataaca aatgtgatga tatggagtgg gagaaggggt ctcttctact   84709
gtcttattgg accctagcag tggctctgag ccagcagtcc tgtcagttga tttcttggtc   84769
gttcctttgt tttcttctat aatcacatgt ggactcagaa tgaattttga gttactctga   84829
aatctattta ttcaacagat atttacttag tacctcctat tgccagactc tgctttatgt   84889
tggatattat ttttaaaag cccaccttgc ctagatttcc tcaaaggacc aggtggcttc   84949
cctggttttg aaagacccta attcttacta tgatcttaag taaattatat cctttctgtg   85009
ggctcaagtt ctttctaaga gggctctttg gggctacaaa agaaattgtt agtgcaaaaa   85069
gagtttataa ggtttataaa tggttagtag aggtgatgat gatatttaac cataattgaa   85129
gatgactttg cattttagat catatacgtg ttttttcgtct gagaacgata caggtcactg   85189
agcataccat aagccttcag taaatcattt gcagaagaca ttgcagaaga cataagtcta   85249
agtagaaatc tcttgacaga gagaaggctc gttttgatcc ttgacctcaa atttaggttc   85309
cctaaatcca ttaaaaaga gaaagaaaaa gaaaaaaagt tactaaagtt taaatctggg   85369
aggattatat acccttctca ataaagcagt ttagagagat ctcttttggg acccatgaca   85429
caggtcttgc tcatgctgac atctttatag ttgcttatt atttattcaa caaacttagt   85489
aacacgtatt ctatgtcagg ccttttcctg actactggga caaaccaggg tgatgtgggg   85549
gctgttttag atagggtgat cagaggaggc ctctctgttt gggtggcttt tgaatagaaa   85609
attagatgaa gtgaaggagt aagcttctga tatttcactg tttacttgtg gtagatctgt   85669
gataatctct gtcaggttaa aaacattccc ttctaatcta agtttctaag atctatcaaa   85729
agctgtttga atatatttag acaatcataa ttttcctttc ttgtattatc ctagcagatt   85789
ttgttgccaa agctatactg gccattttaa cttagaatgc agtctttcta ttcatttctc   85849
tggaaaagtt tggatattgt aagcattatt tttcttagg tatgatgaac ctgcagaact   85909
gtttggttca attatgaatt ttttttttct ggagtctgta ttttttgaa ctattaatca   85969 tttctttaat gattataat ctattcagat ttttacaagc tttatccctc tcccatcata   86029
cactattttt cttacccatg cttttgcaca atttttcct ctcccttagt gttttcctac   86089
ctagatacct cctatgtgtg tctgtgtatg tgagaaaagc ttttattg ccatctttat   86149
```

```
atttctaaga atatctagta atacagaatt ttatattctg aagaatttta ctttgcattt    86209
tcttattttg tgattgaaaa aaggtattaa ttttaaaatg gtcaaatcag gctccatcct    86269
tggaaaatac ccaaatcctt tatttttgatt gggccatctg ttaattaggg ataccttatc   86329
tcttgccacc acttttttaat gctaaataaa tatgtagcta aaactttgac tagaagaaac   86389
agtaaaataa gatattcttg cttattttta gtacagttat ttgaactgac ttttaaatca    86449
gtgacataaa ttatttgcca tgtctatact ttttttcctt atactttttag a atg tat    86506
                                                          Met Tyr
                                                          2275
```

| | | | | | | | | | | | | |
|---|---|---|---|---|---|---|---|---|---|---|---|---|
| gaa | acc | aag | tta | aaa | gaa | ttg | gaa | act | gat | att | gcc | aaa | aaa | aat | 86551 |
| Glu | Thr | Lys | Leu | Lys | Glu | Leu | Glu | Thr | Asp | Ile | Ala | Lys | Lys | Asn | |
| | | | 2280 | | | | | 2285 | | | | | 2290 | | |

```
caa agc att act gac  ctt aaa cag ctt gta  aaa gaa gca aca gag        86596
Gln Ser Ile Thr Asp  Leu Lys Gln Leu Val  Lys Glu Ala Thr Glu
                2295                 2300                2305 aga gaa caa aaa gtt  aac aaa tac aat gaa  gac ctt gaa caa cag        86641
Arg Glu Gln Lys Val  Asn Lys Tyr Asn Glu  Asp Leu Glu Gln Gln
                2310                 2315                2320 gtaagtaacg taatttttct ttacatgata aataatgca taatatcgca agatgttcct    86701
tgcattgtct tatatagata aaaatggact ctattaagaa gacccatcta actgaagggc    86761
accccattca cccatttgct taagccagaa actttggatc atcaacgact tcattctttt    86821
cattctccac atttctatc attaaatcat gtcagctcta ttttcaaact atatcctaaa     86881
tatgaccact tcttggtatc ttgagacatc actaccagtc ttgtccaagc tattgtttta    86941
tacctgaata actgcaataa tttccaagct ggtatctcag cttccactct tggattattt    87001
caccctattt ctatttctgg gctgtctcca cacagttgcc aggtaaccct tttaaaacat    87061
aaagcacatc acaaagcaca aagtcctatc ctcagaatct tccagtggtt ctccatcacc    87121
ctaaaataaa acttaaaagt tcttttcata tcccaaaaca acatatgagg tctggcaccc    87181
agttttcttc ccaatctcat cttctactac ttttcccttc atttcattca caatgtttta    87241
accacagtaa ccttctttca gtactttaaa caatccaaac tcgtttaagc gtcaagtcct    87301
tatacttgtt tcctttgttt agaatactgt tcacccaaat attctcatag cttgctccca    87361
gacttcatgt ctctgctgaa atagaggctc cttagagaga ccttccctaa ccctaaccct    87421
aaccctatac tacttgccat cactctttat cctcttaccc tggattattt tttcttgata    87481
gctcttccta ccatctggca ctatattaca tcatatcata ttaaacacac attctttgtg    87541
cttccccact aaacaaggac catgcaagat ggaacattgc cattttgttc actgctgtta    87601
gcctctgtgc ctaggacaat gccagttatg cagtagttac tcaatacttg ttgaatgaat    87661
ggtgaataga acatagaaat ttgcctatgc gtgcttttga aaaccatatt ttaatattac    87721
gctttgttaa aaatgtgtat ctttataaat cctcatattt ccatggcaaa ccttatcttc    87781
taacttttca ttgtcctcaa ag att aag att ctt aaa  cat gtt cct gaa        87830
                         Ile Lys Ile Leu Lys  His Val Pro Glu
                                         2325 ggt gct gag aca gag caa  ggc ctt aaa cgg gag  ctt caa gtt ctt        87875
Gly Ala Glu Thr Glu Gln  Gly Leu Lys Arg Glu  Leu Gln Val Leu
2330              2335                  2340 ag  gtacatcatg tattcatatg actactttgt ttttttcttt aaaaaaaaaa           87927
Arg
2345 ttattagttt ttatatactc cgaattgcta caactagaga caagcatttt tcgactttac    87987 tgcctaacag gcttattagg tccttatttc ttccctctaa tgctaatcac tcttttttcat   88047
```

```
aatacacact agaaaaaaag gataaaccca actctaagtt tccagtttgt aatttagttt    88107
aaacttttct aagagcatag aatgagttaa accttagctt cccagaggaa aatactaatg    88167
aaagagaaca agtaattttt ttactttcag gggtctctgt agcctgcttt cattaagctc    88227
ctcttataac gaaaccacac ttgcaaatgc catcaggtca gatattaaga aaaacgtgaa    88287
ggcttttgta ttccaggctt tttgtttgag aatggtgaca ttgtagcatt gagagtaaat    88347
gtttacttcg ataaaggcta gcttgttctg attactgtac atcactagtt cataagaaat    88407
gcccatatat tttatgaagc aatatctgct ttatttttt aacacattat cattgtgttc     88467
```

| tag a | tta | gct | aat | cat | cag | ctg | gat | aaa | gag | aaa | gca | gaa | tta | atc | 88513 |
|---|---|---|---|---|---|---|---|---|---|---|---|---|---|---|---|
|  | Leu | Ala | Asn | His | Gln | Leu | Asp | Lys | Glu | Lys | Ala | Glu | Leu | Ile |  |
|  |  |  |  | 2350 |  |  |  |  | 2355 |  |  |  |  |  |  |

| cat | cag | ata | gaa | gct | aac | aag | gac | caa | agt | gga | gct | gaa | agc | acc | 88558 |
|---|---|---|---|---|---|---|---|---|---|---|---|---|---|---|---|
| His | Gln | Ile | Glu | Ala | Asn | Lys | Asp | Gln | Ser | Gly | Ala | Glu | Ser | Thr |  |
| 2360 |  |  |  |  | 2365 |  |  |  |  | 2370 |  |  |  |  |  |

| ata | cct | g gtaatgtatt ttaaaaaaca tgttagctac ccccaagttt tgaatttgg | 88615 |
|---|---|---|---|
| Ile | Pro |  |  |
| 2375 |  |  |  |

```
gtttgccttt ttttttttt tttggctcag atttctgatc attgtctccc tgtaaaatcg     88675
aattcctgat aagctttggg tcttttgtct ctctgtgcta ttaatataaa aatattccca    88735
tttttctctt tgtgttgttt atactataga gtagcaagta cccaagtgtt cttctctttg    88795
ttctccatct gggtgttaca gatttaatca caatacagtg ctaagcaatg aatactaaat    88855
ctgttgcttc cagtttctaa gtataggctc tttcaagtcc tctgaacatt tttaaaaact    88915
gcaaataagt aaatactgcc tatatttttt tccgtttaca agtaaaaag aaaatctttc     88975 tgctcccttc cattcccatt caaaagtgat tactaatcat tcctcattcc tgcatataca    89035
tacacacata ttttgtatac atatatatca cacatatgca tacatgtgtt tgtatgttca    89095
tatgtacaat gtacatatcc tcattatttg tggattctgt attttctaaa tcacctcctc    89155
actaaagtgt gtatgtaatc ccaaatcaac actcgcagca catttgcaaa catccacaga    89215
gccttggaaa gtttgaataa tccaacctac atgtccccag cagaagtcca acaaggcagt    89275
gctcagtatc ctcatttcag ttttcataga gaaatgagca gaggatggag acagtagagg    89335
gcagcacagc atagtgcaag aagctgtggc tctggggcct ggtggaaggg atttgaatcc    89395
caattctgag gcttgttact gctctagcct taggagagtc atgtaacact tctgaatctt    89455
gttttcttat gtaaataaat agaatttacc aggatgagtt atctttagga tttaagatta    89515
tcatctgtgt gagatatgta ggtgtatgta tatatatgcg tgtatgtata tatatgcgtg    89575
tatgtatata tatgcatgtc tgtacatatt tcccgtagca gcagtggttt gatattcact    89635
aattgggcta actttataga ccaaaactac tatggataga gaatactttg tttgcattta    89695
cgtatatata ttttcttggc aagtaacata aaattgaact aatactatac acatttctag    89755
catatttgcc tttaacagtt tatcatggac atcttttgag gtctgttcat aaattatctc    89815
atccatttaa taattccata gtgtattatt gcatgtataa gcacatcgaa ccatttatgt    89875
tttgatggat atttagtttg cttccaagtt tctgcttcta taaaatatga ttaatctatt    89935
gacctaatta tgccattgtg ataggatgat agagatgcca ttctctccaa aggattatac    89995
caatttatat ctgaactatc tttgactatc tcttgtagct ttttcagtat gctatgtagt    90055
cctattacta atttgtaata aaagccatca tgtgtgagtt gtactagaca ctatgctaat    90115
tgccttacaa gcattctata tttacaacca tatatgatag gtattactgt ctccatttta    90175
tgtgataaac aaattcaaag tggttaagta accattccct aagccagcta ggaaatagag    90235
```

```
gcaggattaa aatctaaatg tatgaaactc cacagctcct tggcattcct agtccttaac    90295
ccgctatgct atgctacgtc ttggtaacta aaagtacata ttaaatactc tcaaaatatg    90355
tctcatagca gccagcttgg tatgtacact agacacagta ttaatgctgt tgatgtgagg    90415
aaaattttat aattttcctt ccatccatat actaaccagg cccaacagtg cttagcttct    90475
gagatcagag atcaggtgca tgtgcattaa gggtcatatg gccatagata gttctctaat    90535
ctttccattc ctcagtttct taagggaatt tctgaaccct caaaattcct tatttcctaa    90595
gtagacagat tacctgtcat ttttcaaaga ttaaggctta agatcaaacc agaactgttt    90655
tggaaattct aaatcactgt ctatataaat ggcaagataa cttttaagat atttatacca    90715
agcccagtac agtagcacac cacacctgta atcccagcac tttgggaggc tgaagtgggt    90775
ggatcacatg aggtcaggag ttcgagacca ctctggccaa catggtgaaa ccctgtctct    90835
actaaaaata taaaaattag ccaggcatgg tggcacttgc ctgttatccc agctacaagg    90895
gaggctaagg caggagaatc gctttaacct gggaggcagt ggttgttgca gtgagccaag    90955
attgcaccac tgcactctag cctgggcgac agagtgagac tgtctcaaaa aaaaaaaaa    91015 aaaaaaagat acttgtccca gccatgaaaa tgtttgctgc cccttacttt cgcaaacttt    91075
tagtatttta ttatttttca atggctgtaa aatatgactt attaaatgta gtataatata    91135
aagaaaagag atatctagca aagatagcat taaagcaaaa atcctatttg cctgctgata    91195
aagttagagg tgttaacttg gagggtgaat ccaataaatt agaactttg tgctatattt    91255 ggagactttt gttttcctac caaagtatca gggctatgtc ttacttatct ttgtattaca    91315
cagcctgcat gacacgtttt gcacatagta attgcacagt aaatgtgtaa taacctacat    91375
ggaatagcca gtgttgtgtt ggatagcggg agcatttggc tagcttatgg ttatagtccc    91435
ttacccaaca gtctgctttt cttctgttgt acttttagta cctaacaagt ttccctggct    91495
ttaggatttt ttccatgtaa aatttctatc atgtgaagaa aaaataactt ggcctacact    91555
tctaataccg agcacatacc tctttctgcc tgctatgaaa ttataatact tgatggaggg    91615
aggcagcatt aagtgtttac atcctgaagt atttcagcca taacatccag tgttttccag    91675
gttctaggtt tcataaaatg tatctctgtt ctctagaaca aatccattac cttgaactca    91735
ttcgtagtgg gaaaaagctg agtctaattt gtatgacttt ttcaacag at  gct gat    91791
                                                        Asp Ala Asp caa cta aag gaa aaa ata aaa gat cta gag aca cag ctc aaa atg          91836
Gln Leu Lys Glu Lys Ile Lys Asp Leu Glu Thr Gln Leu Lys Met
2380            2385                2390 tca gat cta gaa aag cag cat ttg aag gtaatatta attatatttt             91883
Ser Asp Leu Glu Lys Gln His Leu Lys
2395            2400 agtatcgttt tgtgaaaaca gctgttgaaa actattttca ttaccatctt taactacgta    91943
tcctaaaaaa ttcagtaata acatcttata tttgaccttt atattgcaaa gttaattatg    92003
ttcatctgac tattcctaac atattagagt taacaaaaaa ttcagactca acataggatt    92063
aagtagtaaa tttattttt aattgtaaca aatatatgcc attagtatgt tcttaagttt    92123
tgggtcacat tggcaacagt gtctttattt ttttttgaa attcttttca ggaatcctaa    92183
ggttatagtt cccttaaaaa aatatttgct gttttacctc ttttaagact gtaaacagga    92243
caaaaaggca tggatatgag aattagctag tgatcactgg ctattctaaa tagtcactaa    92303
ggcttgaatt gtctcttcac cagatgcctg tcagaagtcc caaggtttc cctgatcata     92363 ttaataactt tataaaaaat tgatcattat tcattaaata ttagatatta gtaaggaaaa    92423
```

```
tataaatgaa gtctaaacca aaactcttaa ccagactaac ttcaatgtta tgaatcacaa    92483 aatcttttg attgattgct ctattgacaa gctcttatat gcttttagag aaagattaag     92543
tcccattata agagatgata aattttagtc aaagactaga acacaactta cagaatacat    92603
aactggactt gacagttaac aacttagtta tttacactgt acaatggaac aaagaaaaat    92663
cttaattctt ctgcctttat tgctgtattt gaccattcag gaatactttg gctttcatat    92723
ttacaattaa atctccttgt tcaaacgtaa aatatgtata tttcctatat gcaactttta    92783
```

| aagataatgt ttccattag | gag gaa ata aag aag ctg aaa aaa gaa ctg<br>Glu Glu Ile Lys Lys Leu Lys Lys Glu Leu<br>       2405            2410 | 92832 |
|---|---|---|
| | gaa aat ttt gat cct tca ttt ttt gaa gaa att gaa gat ctt aag<br>Glu Asn Phe Asp Pro Ser Phe Phe Glu Glu Ile Glu Asp Leu Lys<br>      2415            2420            2425 | 92877 |
| | tat aat tac aag gaa gaa gtg aag aag aat att ctc tta gaa gag<br>Tyr Asn Tyr Lys Glu Glu Val Lys Lys Asn Ile Leu Leu Glu Glu<br>Tyr 2430           2435            2440 | 92922 |
| | aag gta aaa aaa ctt tca gaa caa ttg gga gtt gaa tta act agc<br>Lys Val Lys Lys Leu Ser Glu Gln Leu Gly Val Glu Leu Thr Ser<br>     2445            2450            2455 | 92967 |
| | cct gtt gct gct tct gaa gag ttt gaa gat gaa gaa gaa agt cct<br>Pro Val Ala Ala Ser Glu Glu Phe Glu Asp Glu Glu Glu Ser Pro<br>    2460            2465            2470 | 93012 |
| | gtt aat ttc ccc att tac taa aggtcaccta taaactttgt ttcatttaac<br>Val Asn Phe Pro Ile Tyr<br>    2475 | 93063 |

```
tatttattaa ctttataagt taaatatact tggaaataag cagttctccg aactgtagta    93123
tttccttctc actaccttgt acctttatac ttagattgga attcttaata aataaaatta    93183
tatgaaattt tcaacttatt                                                 93203

<210> SEQ ID NO 2
<211> LENGTH: 7972
<212> TYPE: DNA
<213> ORGANISM: Homo sapiens
<220> FEATURE:
<221> NAME/KEY: CDS
<222> LOCATION: (345)..(7781)

<400> SEQUENCE: 2
atttgaagtc ctcgttccac gccttctcat catcctgaac accgagctct gggactccgg     60
cggagaatct aaacgtaaag catcacccac ggtcgtgaac tgtaggctct cctggcatcc    120
gggatcttat tctggccttg gcggagttgg ggatggtgtc gcctagcagc cgctgccgct    180
ttggcttgct cggaccatt tggctggacc cagagtccgc gtggaaccgc gatagggatc     240
tgtcagggcc cgcggccggg tccagcttgg tggttgcggt agtgagaggc ctccgctggt    300
tgccaggctt ggtctagagg tggagcacag tgaaagaatt caag atg cca cct aat    356
                                                   Met Pro Pro Asn
                                                    1
```

| | ata aac tgg aaa gaa ata atg aaa gtt gac cca gat gac ctg ccc cgt<br>Ile Asn Trp Lys Glu Ile Met Lys Val Asp Pro Asp Asp Leu Pro Arg<br>5              10              15              20 | 404 |
|---|---|---|
| | caa gaa gaa ctg gca gat aat tta ttg att tcc tta tcc aag gtg gaa<br>Gln Glu Glu Leu Ala Asp Asn Leu Leu Ile Ser Leu Ser Lys Val Glu<br>         25              30              35 | 452 |
| | gta aat gag cta aaa agt gaa aag caa gaa aat gtg ata cac ctt ttc<br>Val Asn Glu Leu Lys Ser Glu Lys Gln Glu Asn Val Ile His Leu Phe<br>      40              45              50 | 500 |

```
aga att act cag tca cta atg aag atg aaa gct caa gaa gtg gag ctg      548
Arg Ile Thr Gln Ser Leu Met Lys Met Lys Ala Gln Glu Val Glu Leu
        55                  60                  65 gct ttg gaa gaa gta gaa aaa gct gga gaa gaa caa gca aaa ttt gaa      596
Ala Leu Glu Glu Val Glu Lys Ala Gly Glu Glu Gln Ala Lys Phe Glu
70                  75                  80 aat caa tta aaa act aaa gta atg aaa ctg gaa aat gaa ctg gag atg      644
Asn Gln Leu Lys Thr Lys Val Met Lys Leu Glu Asn Glu Leu Glu Met
85                  90                  95                 100 gct cag cag tct gca ggt gga cga gat act cgg ttt tta cgt aat gaa      692
Ala Gln Gln Ser Ala Gly Gly Arg Asp Thr Arg Phe Leu Arg Asn Glu
            105                 110                 115 att tgc caa ctt gaa aaa caa tta gaa caa aaa gat aga gaa ttg gag      740
Ile Cys Gln Leu Glu Lys Gln Leu Glu Gln Lys Asp Arg Glu Leu Glu
    120                 125                 130 gac atg gaa aag gag ttg gag aaa gag aag aaa gtt aat gag caa ttg      788
Asp Met Glu Lys Glu Leu Glu Lys Glu Lys Lys Val Asn Glu Gln Leu
        135                 140                 145 gct ctt cga aat gag gag gca gaa aat gaa aac agc aaa tta aga aga      836
Ala Leu Arg Asn Glu Glu Ala Glu Asn Glu Asn Ser Lys Leu Arg Arg
150                 155                 160 gag aac aaa cgt cta aag aaa aag aat gaa caa ctt tgt cag gat att      884
Glu Asn Lys Arg Leu Lys Lys Lys Asn Glu Gln Leu Cys Gln Asp Ile
165                 170                 175                 180 att gac tac cag aaa caa ata gat tca cag aaa gaa aca ctt tta tca      932
Ile Asp Tyr Gln Lys Gln Ile Asp Ser Gln Lys Glu Thr Leu Leu Ser
            185                 190                 195 aga aga ggg gaa gac agt gac tac cga tca cag ttg tct aaa aaa aac      980
Arg Arg Gly Glu Asp Ser Asp Tyr Arg Ser Gln Leu Ser Lys Lys Asn
        200                 205                 210 tat gag ctt atc caa tat ctt gat gaa att cag act tta aca gaa gct     1028
Tyr Glu Leu Ile Gln Tyr Leu Asp Glu Ile Gln Thr Leu Thr Glu Ala
    215                 220                 225 aat gag aaa att gaa gtt cag aat caa gaa atg aga aaa aat tta gaa     1076
Asn Glu Lys Ile Glu Val Gln Asn Gln Glu Met Arg Lys Asn Leu Glu
230                 235                 240 gag tct gta cag gaa atg gag aag atg act gat gaa tat aat aga atg     1124
Glu Ser Val Gln Glu Met Glu Lys Met Thr Asp Glu Tyr Asn Arg Met
245                 250                 255                 260 aaa gct att gtg cat cag aca gat aat gta ata gat cag tta aaa aaa     1172
Lys Ala Ile Val His Gln Thr Asp Asn Val Ile Asp Gln Leu Lys Lys
            265                 270                 275 gaa aac gat cat tat caa ctt caa gtg cag gag ctt aca gat ctt ctg     1220
Glu Asn Asp His Tyr Gln Leu Gln Val Gln Glu Leu Thr Asp Leu Leu
        280                 285                 290 aaa tca aaa aat gaa gaa gat gat cca att atg gta gct gtc aat gca     1268
Lys Ser Lys Asn Glu Glu Asp Asp Pro Ile Met Val Ala Val Asn Ala
    295                 300                 305 aaa gta gaa gaa tgg aag cta att ttg tct tct aaa gat gat gaa att     1316
Lys Val Glu Glu Trp Lys Leu Ile Leu Ser Ser Lys Asp Asp Glu Ile
310                 315                 320 att gag tat cag caa atg tta cat aac cta agg gag aaa ctt aag aat     1364
Ile Glu Tyr Gln Gln Met Leu His Asn Leu Arg Glu Lys Leu Lys Asn
325                 330                 335                 340 gct cag ctt gat gct gat aaa agt aat gtt atg gct cta cag cag ggt     1412
Ala Gln Leu Asp Ala Asp Lys Ser Asn Val Met Ala Leu Gln Gln Gly
            345                 350                 355
```

```
ata cag gaa cga gac agt caa att aag atg ctc acc gaa caa gta gaa     1460
Ile Gln Glu Arg Asp Ser Gln Ile Lys Met Leu Thr Glu Gln Val Glu
            360                 365                 370 caa tat aca aaa gaa atg gaa aag aat act tgt att att gaa gat ttg     1508
Gln Tyr Thr Lys Glu Met Glu Lys Asn Thr Cys Ile Ile Glu Asp Leu
        375                 380                 385 aaa aat gag ctc caa aga aac aaa ggt gct tca acc ctt tct caa cag     1556
Lys Asn Glu Leu Gln Arg Asn Lys Gly Ala Ser Thr Leu Ser Gln Gln
    390                 395                 400 act cat atg aaa att cag tca acg tta gac att tta aaa gag aaa act     1604
Thr His Met Lys Ile Gln Ser Thr Leu Asp Ile Leu Lys Glu Lys Thr
405                 410                 415                 420 aaa gag gct gag aga aca gct gaa ctg gct gag gct gat gct agg gaa     1652
Lys Glu Ala Glu Arg Thr Ala Glu Leu Ala Glu Ala Asp Ala Arg Glu
                425                 430                 435 aag gat aaa gaa tta gtt gag gct ctg aag agg tta aaa gat tat gaa     1700
Lys Asp Lys Glu Leu Val Glu Ala Leu Lys Arg Leu Lys Asp Tyr Glu
            440                 445                 450 tcg gga gta tat ggt tta gaa gat gct gtc gtt gaa ata aag aat tgt     1748
Ser Gly Val Tyr Gly Leu Glu Asp Ala Val Val Glu Ile Lys Asn Cys
        455                 460                 465 aaa aac caa att aaa ata aga gat cga gag att gaa ata tta aca aag     1796
Lys Asn Gln Ile Lys Ile Arg Asp Arg Glu Ile Glu Ile Leu Thr Lys
    470                 475                 480 gaa atc aat aaa ctt gaa ttg aag atc agt gat ttc ctt gat gaa aat     1844
Glu Ile Asn Lys Leu Glu Leu Lys Ile Ser Asp Phe Leu Asp Glu Asn
485                 490                 495                 500 gag gca ctt aga gag cgt gtg ggc ctt gaa cca aag aca atg att gat     1892
Glu Ala Leu Arg Glu Arg Val Gly Leu Glu Pro Lys Thr Met Ile Asp
                505                 510                 515 tta act gaa ttt aga aat agc aaa cac tta aaa cag cag cag tac aga     1940
Leu Thr Glu Phe Arg Asn Ser Lys His Leu Lys Gln Gln Gln Tyr Arg
            520                 525                 530 gct gaa aac cag att ctt ttg aaa gag att gaa agt cta gag gaa gaa     1988
Ala Glu Asn Gln Ile Leu Leu Lys Glu Ile Glu Ser Leu Glu Glu Glu
        535                 540                 545 cga ctt gat ctg aaa aaa aaa att cgt caa atg gct caa gaa aga gga     2036
Arg Leu Asp Leu Lys Lys Lys Ile Arg Gln Met Ala Gln Glu Arg Gly
    550                 555                 560 aaa aga agt gca act tca gga tta acc act gag gac ctg aac cta act     2084
Lys Arg Ser Ala Thr Ser Gly Leu Thr Thr Glu Asp Leu Asn Leu Thr
565                 570                 575                 580 gaa aac att tct caa gga gat aga ata agt gaa aga aaa ttg gat tta     2132
Glu Asn Ile Ser Gln Gly Asp Arg Ile Ser Glu Arg Lys Leu Asp Leu
                585                 590                 595 ttg agc ctc aaa aat atg agt gaa gca caa tca aag aat gaa ttt ctt     2180
Leu Ser Leu Lys Asn Met Ser Glu Ala Gln Ser Lys Asn Glu Phe Leu
            600                 605                 610 tca aga gaa cta att gaa aaa gaa aga gat tta gaa agg agt agg aca     2228
Ser Arg Glu Leu Ile Glu Lys Glu Arg Asp Leu Glu Arg Ser Arg Thr
        615                 620                 625 gtg ata gcc aaa ttt cag aat aaa tta aaa gaa tta gtt gaa gaa aat     2276
Val Ile Ala Lys Phe Gln Asn Lys Leu Lys Glu Leu Val Glu Glu Asn
    630                 635                 640 aag caa ctt gaa gaa ggt atg aaa gaa ata ttg caa gca att aag gaa     2324
Lys Gln Leu Glu Glu Gly Met Lys Glu Ile Leu Gln Ala Ile Lys Glu
645                 650                 655                 660 atg cag aaa gat cct gat gtt aaa gga gga gaa aca tct cta att atc     2372
Met Gln Lys Asp Pro Asp Val Lys Gly Gly Glu Thr Ser Leu Ile Ile
                665                 670                 675
```

| | | | | | | | | | | | | | | | | |
|---|---|---|---|---|---|---|---|---|---|---|---|---|---|---|---|---|
| cct | agc | ctt | gaa | aga | cta | gtt | aat | gct | ata | gaa | tca | aag | aat | gca | gaa | 2420 |
| Pro | Ser | Leu | Glu | Arg | Leu | Val | Asn | Ala | Ile | Glu | Ser | Lys | Asn | Ala | Glu | |
| | | | 680 | | | | | 685 | | | | | 690 | | | |
| gga | atc | ttt | gat | gcg | agt | ctg | cat | ttg | aaa | gcc | caa | gtt | gat | cag | ctt | 2468 |
| Gly | Ile | Phe | Asp | Ala | Ser | Leu | His | Leu | Lys | Ala | Gln | Val | Asp | Gln | Leu | |
| | | 695 | | | | | 700 | | | | | 705 | | | | |
| acc | gga | aga | aat | gaa | gaa | tta | aga | cag | gag | ctc | agg | gaa | tct | cgg | aaa | 2516 |
| Thr | Gly | Arg | Asn | Glu | Glu | Leu | Arg | Gln | Glu | Leu | Arg | Glu | Ser | Arg | Lys | |
| | 710 | | | | | 715 | | | | | 720 | | | | | |
| gag | gct | ata | aat | tat | tca | cag | cag | ttg | gca | aaa | gct | aat | tta | aag | ata | 2564 |
| Glu | Ala | Ile | Asn | Tyr | Ser | Gln | Gln | Leu | Ala | Lys | Ala | Asn | Leu | Lys | Ile | |
| 725 | | | | | 730 | | | | | 735 | | | | | 740 | |
| gac | cat | ctt | gaa | aaa | gaa | act | agt | ctt | tta | cga | caa | tca | gaa | gga | tcg | 2612 |
| Asp | His | Leu | Glu | Lys | Glu | Thr | Ser | Leu | Leu | Arg | Gln | Ser | Glu | Gly | Ser | |
| | | | | 745 | | | | | 750 | | | | | 755 | | |
| aat | gtt | gtt | ttt | aaa | gga | att | gac | tta | cct | gat | ggg | ata | gca | cca | tct | 2660 |
| Asn | Val | Val | Phe | Lys | Gly | Ile | Asp | Leu | Pro | Asp | Gly | Ile | Ala | Pro | Ser | |
| | | | 760 | | | | | 765 | | | | | 770 | | | |
| agt | gcc | agt | atc | att | aat | tct | cag | aat | gaa | tat | tta | ata | cat | ttg | tta | 2708 |
| Ser | Ala | Ser | Ile | Ile | Asn | Ser | Gln | Asn | Glu | Tyr | Leu | Ile | His | Leu | Leu | |
| | | | 775 | | | | | 780 | | | | | 785 | | | |
| cag | gaa | cta | gaa | aat | aaa | gaa | aaa | aag | tta | aag | aat | tta | gaa | gat | tct | 2756 |
| Gln | Glu | Leu | Glu | Asn | Lys | Glu | Lys | Lys | Leu | Lys | Asn | Leu | Glu | Asp | Ser | |
| | 790 | | | | | 795 | | | | | 800 | | | | | |
| ctt | gaa | gat | tac | aac | aga | aaa | ttt | gct | gta | att | cgt | cat | caa | caa | agt | 2804 |
| Leu | Glu | Asp | Tyr | Asn | Arg | Lys | Phe | Ala | Val | Ile | Arg | His | Gln | Gln | Ser | |
| 805 | | | | | 810 | | | | | 815 | | | | | 820 | |
| ttg | ttg | tat | aaa | gaa | tac | cta | agt | gaa | aag | gag | acc | tgg | aaa | aca | gaa | 2852 |
| Leu | Leu | Tyr | Lys | Glu | Tyr | Leu | Ser | Glu | Lys | Glu | Thr | Trp | Lys | Thr | Glu | |
| | | | | 825 | | | | | 830 | | | | | 835 | | |
| tct | aaa | aca | ata | aaa | gag | gaa | aag | aga | aaa | ctt | gag | gat | caa | gtc | caa | 2900 |
| Ser | Lys | Thr | Ile | Lys | Glu | Glu | Lys | Arg | Lys | Leu | Glu | Asp | Gln | Val | Gln | |
| | | | 840 | | | | | 845 | | | | | 850 | | | |
| caa | gat | gct | ata | aaa | gta | aaa | gaa | tat | aat | aat | ttg | ctc | aat | gct | ctt | 2948 |
| Gln | Asp | Ala | Ile | Lys | Val | Lys | Glu | Tyr | Asn | Asn | Leu | Leu | Asn | Ala | Leu | |
| | | 855 | | | | | 860 | | | | | 865 | | | | |
| cag | atg | gat | tcg | gat | gaa | atg | aaa | aaa | ata | ctt | gca | gaa | aat | agt | agg | 2996 |
| Gln | Met | Asp | Ser | Asp | Glu | Met | Lys | Lys | Ile | Leu | Ala | Glu | Asn | Ser | Arg | |
| | 870 | | | | | 875 | | | | | 880 | | | | | |
| aaa | att | act | gtt | ttg | caa | gtg | aat | gaa | aaa | tca | ctt | ata | agg | caa | tat | 3044 |
| Lys | Ile | Thr | Val | Leu | Gln | Val | Asn | Glu | Lys | Ser | Leu | Ile | Arg | Gln | Tyr | |
| 885 | | | | | 890 | | | | | 895 | | | | | 900 | |
| aca | acc | tta | gta | gaa | ttg | gag | cga | caa | ctt | aga | aaa | gaa | aat | gag | aag | 3092 |
| Thr | Thr | Leu | Val | Glu | Leu | Glu | Arg | Gln | Leu | Arg | Lys | Glu | Asn | Glu | Lys | |
| | | | | 905 | | | | | 910 | | | | | 915 | | |
| caa | aag | aat | gaa | ttg | ttg | tca | atg | gag | gct | gaa | gtt | tgt | gaa | aaa | att | 3140 |
| Gln | Lys | Asn | Glu | Leu | Leu | Ser | Met | Glu | Ala | Glu | Val | Cys | Glu | Lys | Ile | |
| | | | 920 | | | | | 925 | | | | | 930 | | | |
| ggg | tgt | ttg | caa | aga | ttt | aag | gaa | atg | gcc | att | ttc | aag | att | gca | gct | 3188 |
| Gly | Cys | Leu | Gln | Arg | Phe | Lys | Glu | Met | Ala | Ile | Phe | Lys | Ile | Ala | Ala | |
| | | 935 | | | | | 940 | | | | | 945 | | | | |
| ctc | caa | aaa | gtt | gta | gat | aat | agt | gtt | tct | ttg | tct | gaa | cta | gaa | ctg | 3236 |
| Leu | Gln | Lys | Val | Val | Asp | Asn | Ser | Val | Ser | Leu | Ser | Glu | Leu | Glu | Leu | |
| | 950 | | | | | 955 | | | | | 960 | | | | | |
| gct | aat | aaa | cag | tac | aat | gaa | ctg | act | gct | aag | tac | agg | gac | atc | ttg | 3284 |
| Ala | Asn | Lys | Gln | Tyr | Asn | Glu | Leu | Thr | Ala | Lys | Tyr | Arg | Asp | Ile | Leu | |
| 965 | | | | | 970 | | | | | 975 | | | | | 980 | |
| caa | aaa | gat | aat | atg | ctt | gtt | caa | aga | aca | agt | aac | ttg | gaa | cac | ctg | 3332 |
| Gln | Lys | Asp | Asn | Met | Leu | Val | Gln | Arg | Thr | Ser | Asn | Leu | Glu | His | Leu | |
| | | | | 985 | | | | | 990 | | | | | 995 | | |

```
                                    -continued gag tgt gaa aac atc tcc tta aaa gaa caa gtg gag tct ata aat      3377
Glu Cys Glu Asn Ile Ser Leu Lys Glu Gln Val Glu Ser Ile Asn
            1000            1005            1010 aaa gaa ctg gag att acc aag gaa aaa ctt cac act att gaa caa      3422
Lys Glu Leu Glu Ile Thr Lys Glu Lys Leu His Thr Ile Glu Gln
            1015            1020            1025 gcc tgg gaa cag gaa act aaa tta ggt aat gaa tct agc atg gat      3467
Ala Trp Glu Gln Glu Thr Lys Leu Gly Asn Glu Ser Ser Met Asp
            1030            1035            1040 aag gca aag aaa tca ata acc aac agt gac att gtt tcc att tca      3512
Lys Ala Lys Lys Ser Ile Thr Asn Ser Asp Ile Val Ser Ile Ser
            1045            1050            1055 aaa aaa ata act atg ctg gaa atg aag gaa tta aat gaa agg cag      3557
Lys Lys Ile Thr Met Leu Glu Met Lys Glu Leu Asn Glu Arg Gln
            1060            1065            1070 cgg gct gaa cat tgt caa aaa atg tat gaa cac tta cgg act tcg      3602
Arg Ala Glu His Cys Gln Lys Met Tyr Glu His Leu Arg Thr Ser
            1075            1080            1085 tta aag caa atg gag gaa cgt aat ttt gaa ttg gaa acc aaa ttt      3647
Leu Lys Gln Met Glu Glu Arg Asn Phe Glu Leu Glu Thr Lys Phe
            1090            1095            1100 gct gag ctt acc aaa atc aat ttg gat gca cag aag gtg gaa cag      3692
Ala Glu Leu Thr Lys Ile Asn Leu Asp Ala Gln Lys Val Glu Gln
            1105            1110            1115 atg tta aga gat gaa tta gct gat agt gtg agc aag gca gta agt      3737
Met Leu Arg Asp Glu Leu Ala Asp Ser Val Ser Lys Ala Val Ser
            1120            1125            1130 gat gct gat agg caa cgg att cta gaa tta gag aag aat gaa atg      3782
Asp Ala Asp Arg Gln Arg Ile Leu Glu Leu Glu Lys Asn Glu Met
            1135            1140            1145 gaa cta aaa gtt gaa gtg tca aaa ctg aga gag att tct gat att      3827
Glu Leu Lys Val Glu Val Ser Lys Leu Arg Glu Ile Ser Asp Ile
            1150            1155            1160 gcc aga aga caa gtt gaa att ttg aat gca caa caa caa tct agg      3872
Ala Arg Arg Gln Val Glu Ile Leu Asn Ala Gln Gln Gln Ser Arg
            1165            1170            1175 gac aag gaa gta gag tcc ctc aga atg caa ctg cta gac tat cag      3917
Asp Lys Glu Val Glu Ser Leu Arg Met Gln Leu Leu Asp Tyr Gln
            1180            1185            1190 gca cag tct gat gaa aag tcg ctc att gcc aag ttg cac caa cat      3962
Ala Gln Ser Asp Glu Lys Ser Leu Ile Ala Lys Leu His Gln His
            1195            1200            1205 aat gtc tct ctt caa ctg agt gag gct act gct ctt ggt aag ttg      4007
Asn Val Ser Leu Gln Leu Ser Glu Ala Thr Ala Leu Gly Lys Leu
            1210            1215            1220 gag tca att aca tct aaa ctg cag aag atg gag gcc tac aac ttg      4052
Glu Ser Ile Thr Ser Lys Leu Gln Lys Met Glu Ala Tyr Asn Leu
            1225            1230            1235 cgc tta gag cag aaa ctt gat gaa aaa gaa cag gct ctc tat tat      4097
Arg Leu Glu Gln Lys Leu Asp Glu Lys Glu Gln Ala Leu Tyr Tyr
            1240            1245            1250 gct cgt ttg gag gga aga aac aga gca aaa cat ctg cgc caa aca      4142
Ala Arg Leu Glu Gly Arg Asn Arg Ala Lys His Leu Arg Gln Thr
            1255            1260            1265 att cag tct cta cga cga cag ttt agt gga gct tta ccc ttg gca      4187
Ile Gln Ser Leu Arg Arg Gln Phe Ser Gly Ala Leu Pro Leu Ala
            1270            1275            1280 caa cag gaa aag ttc tcc aaa aca atg att caa cta caa aat gac      4232
Gln Gln Glu Lys Phe Ser Lys Thr Met Ile Gln Leu Gln Asn Asp
            1285            1290            1295
```

```
aaa ctt aag ata atg caa gaa atg aaa aat tct caa caa gaa cat         4277
Lys Leu Lys Ile Met Gln Glu Met Lys Asn Ser Gln Gln Glu His
            1300                1305                1310 aga aat atg gag aac aaa aca ttg gag atg gaa tta aaa tta aag         4322
Arg Asn Met Glu Asn Lys Thr Leu Glu Met Glu Leu Lys Leu Lys
            1315                1320                1325 ggc ctg gaa gag tta ata agc act tta aag gat acc aaa gga gcc         4367
Gly Leu Glu Glu Leu Ile Ser Thr Leu Lys Asp Thr Lys Gly Ala
            1330                1335                1340 caa aag gta atc aac tgg cat atg aaa ata gaa gaa ctt cgt ctt         4412
Gln Lys Val Ile Asn Trp His Met Lys Ile Glu Glu Leu Arg Leu
            1345                1350                1355 caa gaa ctt aaa cta aat cgg gaa tta gtc aag gat aaa gaa gaa         4457
Gln Glu Leu Lys Leu Asn Arg Glu Leu Val Lys Asp Lys Glu Glu
            1360                1365                1370 ata aaa tat ttg aat aac ata att tct gaa tat gaa cgt aca atc         4502
Ile Lys Tyr Leu Asn Asn Ile Ile Ser Glu Tyr Glu Arg Thr Ile
            1375                1380                1385 agc agt ctt gaa gaa gaa att gtg caa cag aac aag ttt cat gaa         4547
Ser Ser Leu Glu Glu Glu Ile Val Gln Gln Asn Lys Phe His Glu
            1390                1395                1400 gaa aga caa atg gcc tgg gat caa aga gaa gtt gac ctg gaa cgc         4592
Glu Arg Gln Met Ala Trp Asp Gln Arg Glu Val Asp Leu Glu Arg
            1405                1410                1415 caa cta gac att ttt gac cgt cag caa aat gaa ata cta aat gcg         4637
Gln Leu Asp Ile Phe Asp Arg Gln Gln Asn Glu Ile Leu Asn Ala
            1420                1425                1430 gca caa aag ttt gaa gaa gct aca gga tca atc cct gac cct agt         4682
Ala Gln Lys Phe Glu Glu Ala Thr Gly Ser Ile Pro Asp Pro Ser
            1435                1440                1445 ttg ccc ctt cca aat caa ctt gag atc gct cta agg aaa att aag         4727
Leu Pro Leu Pro Asn Gln Leu Glu Ile Ala Leu Arg Lys Ile Lys
            1450                1455                1460 gag aac att cga ata att cta gaa aca cgg gca act tgc aaa tca         4772
Glu Asn Ile Arg Ile Ile Leu Glu Thr Arg Ala Thr Cys Lys Ser
            1465                1470                1475 cta gaa gag aaa cta aaa gag aaa gaa tct gct tta agg tta gca         4817
Leu Glu Glu Lys Leu Lys Glu Lys Glu Ser Ala Leu Arg Leu Ala
            1480                1485                1490 gaa caa aat ata ctg tca aga gac aaa gta atc aat gaa ctg agg         4862
Glu Gln Asn Ile Leu Ser Arg Asp Lys Val Ile Asn Glu Leu Arg
            1495                1500                1505 ctt cga ttg cct gcc act gca gaa aga gaa aag ctc ata gct gag         4907
Leu Arg Leu Pro Ala Thr Ala Glu Arg Glu Lys Leu Ile Ala Glu
            1510                1515                1520 cta ggc aga aaa gag atg gaa cca aaa tct cac cac aca ttg aaa         4952
Leu Gly Arg Lys Glu Met Glu Pro Lys Ser His His Thr Leu Lys
            1525                1530                1535 att gct cat caa acc att gca aac atg caa gca agg tta aat caa         4997
Ile Ala His Gln Thr Ile Ala Asn Met Gln Ala Arg Leu Asn Gln
            1540                1545                1550 aaa gaa gaa gta tta aag aag tat caa cgt ctt cta gaa aaa gcc         5042
Lys Glu Glu Val Leu Lys Lys Tyr Gln Arg Leu Leu Glu Lys Ala
            1555                1560                1565 aga gag gag caa aga gaa att gtg aag aaa cat gag gaa gac ctt         5087
Arg Glu Glu Gln Arg Glu Ile Val Lys Lys His Glu Glu Asp Leu
            1570                1575                1580 cat att ctt cat cac aga tta gaa cta cag gct gat agt tca cta         5132
His Ile Leu His His Arg Leu Glu Leu Gln Ala Asp Ser Ser Leu
            1585                1590                1595
```

| | | | | | | | | | | | | |
|---|---|---|---|---|---|---|---|---|---|---|---|---|
| aat | aaa | ttc | aaa | caa | acg | gct | tgg | gat | tta | atg | aaa | cag | tct | ccc | 5177 |
| Asn | Lys | Phe | Lys | Gln | Thr | Ala | Trp | Asp | Leu | Met | Lys | Gln | Ser | Pro | |
| | | | 1600 | | | | | 1605 | | | | | 1610 | | |
| act | cca | gtt | cct | acc | aac | aag | cat | ttt | att | cgt | ctg | gct | gag | atg | 5222 |
| Thr | Pro | Val | Pro | Thr | Asn | Lys | His | Phe | Ile | Arg | Leu | Ala | Glu | Met | |
| | | 1615 | | | | | 1620 | | | | | 1625 | | | |
| gaa | cag | aca | gta | gca | gaa | caa | gat | gac | tct | ctt | tcc | tca | ctc | ttg | 5267 |
| Glu | Gln | Thr | Val | Ala | Glu | Gln | Asp | Asp | Ser | Leu | Ser | Ser | Leu | Leu | |
| | 1630 | | | | | 1635 | | | | | 1640 | | | | |
| gtc | aaa | cta | aag | aaa | gta | tca | caa | gat | ttg | gag | aga | caa | aga | gaa | 5312 |
| Val | Lys | Leu | Lys | Lys | Val | Ser | Gln | Asp | Leu | Glu | Arg | Gln | Arg | Glu | |
| 1645 | | | | | 1650 | | | | | 1655 | | | | | |
| atc | act | gaa | tta | aaa | gta | aaa | gaa | ttt | gaa | aat | atc | aaa | tta | cag | 5357 |
| Ile | Thr | Glu | Leu | Lys | Val | Lys | Glu | Phe | Glu | Asn | Ile | Lys | Leu | Gln | |
| | Thr | | 1660 | | | | | 1665 | | | | | 1670 | | |
| ctt | caa | gaa | aac | cat | gaa | gat | gaa | gtg | aaa | aaa | gta | aaa | gcg | gaa | 5402 |
| Leu | Gln | Glu | Asn | His | Glu | Asp | Glu | Val | Lys | Lys | Val | Lys | Ala | Glu | |
| | | | 1675 | | | | | 1680 | | | | | 1685 | | |
| gta | gag | gat | tta | aag | tat | ctt | ctg | gac | cag | tca | caa | aag | gag | tca | 5447 |
| Val | Glu | Asp | Leu | Lys | Tyr | Leu | Leu | Asp | Gln | Ser | Gln | Lys | Glu | Ser | |
| | | 1690 | | | | | 1695 | | | | | 1700 | | | |
| cag | tgt | tta | aaa | tct | gaa | ctt | cag | gct | caa | aaa | gaa | gca | aat | tca | 5492 |
| Gln | Cys | Leu | Lys | Ser | Glu | Leu | Gln | Ala | Gln | Lys | Glu | Ala | Asn | Ser | |
| | 1705 | | | | | 1710 | | | | | 1715 | | | | |
| aga | gct | cca | aca | act | aca | atg | aga | aat | cta | gta | gaa | cgg | cta | aag | 5537 |
| Arg | Ala | Pro | Thr | Thr | Thr | Met | Arg | Asn | Leu | Val | Glu | Arg | Leu | Lys | |
| 1720 | | | | | 1725 | | | | | 1730 | | | | | |
| agc | caa | tta | gcc | ttg | aag | gag | aaa | caa | cag | aaa | gca | ctt | agt | cgg | 5582 |
| Ser | Gln | Leu | Ala | Leu | Lys | Glu | Lys | Gln | Gln | Lys | Ala | Leu | Ser | Arg | |
| | | 1735 | | | | | 1740 | | | | | 1745 | | | |
| gca | ctt | tta | gaa | ctc | cgg | gca | gaa | atg | aca | gca | gct | gct | gaa | gaa | 5627 |
| Ala | Leu | Leu | Glu | Leu | Arg | Ala | Glu | Met | Thr | Ala | Ala | Ala | Glu | Glu | |
| | | 1750 | | | | | 1755 | | | | | 1760 | | | |
| cgt | att | att | tct | gca | act | tct | caa | aaa | gag | gcc | cat | ctc | aat | gtt | 5672 |
| Arg | Ile | Ile | Ser | Ala | Thr | Ser | Gln | Lys | Glu | Ala | His | Leu | Asn | Val | |
| | | 1765 | | | | | 1770 | | | | | 1775 | | | |
| caa | caa | atc | gtt | gat | cga | cat | act | aga | gag | cta | aag | aca | caa | gtt | 5717 |
| Gln | Gln | Ile | Val | Asp | Arg | His | Thr | Arg | Glu | Leu | Lys | Thr | Gln | Val | |
| | | 1780 | | | | | 1785 | | | | | 1790 | | | |
| gaa | gat | tta | aat | gaa | aat | ctt | tta | aaa | ttg | aaa | gaa | gca | ctt | aaa | 5762 |
| Glu | Asp | Leu | Asn | Glu | Asn | Leu | Leu | Lys | Leu | Lys | Glu | Ala | Leu | Lys | |
| | | 1795 | | | | | 1800 | | | | | 1805 | | | |
| aca | agt | aaa | aac | aga | gaa | aac | tca | cta | act | gat | aat | ttg | aat | gac | 5807 |
| Thr | Ser | Lys | Asn | Arg | Glu | Asn | Ser | Leu | Thr | Asp | Asn | Leu | Asn | Asp | |
| | | 1810 | | | | | 1815 | | | | | 1820 | | | |
| tta | aat | aat | gaa | ctg | caa | aag | aaa | caa | aaa | gcc | tat | aat | aaa | ata | 5852 |
| Leu | Asn | Asn | Glu | Leu | Gln | Lys | Lys | Gln | Lys | Ala | Tyr | Asn | Lys | Ile | |
| | | 1825 | | | | | 1830 | | | | | 1835 | | | |
| ctt | aga | gag | aaa | gag | gaa | att | gat | caa | gag | aat | gat | gaa | ctg | aaa | 5897 |
| Leu | Arg | Glu | Lys | Glu | Glu | Ile | Asp | Gln | Glu | Asn | Asp | Glu | Leu | Lys | |
| | | 1840 | | | | | 1845 | | | | | 1850 | | | |
| agg | caa | att | aaa | aga | cta | acc | agt | gga | tta | cag | ggc | aaa | ccc | ctg | 5942 |
| Arg | Gln | Ile | Lys | Arg | Leu | Thr | Ser | Gly | Leu | Gln | Gly | Lys | Pro | Leu | |
| | | 1855 | | | | | 1860 | | | | | 1865 | | | |
| aca | gat | aat | aaa | caa | agt | cta | att | gaa | gaa | ctc | caa | agg | aaa | gtt | 5987 |
| Thr | Asp | Asn | Lys | Gln | Ser | Leu | Ile | Glu | Glu | Leu | Gln | Arg | Lys | Val | |
| | | 1870 | | | | | 1875 | | | | | 1880 | | | |
| aaa | aaa | cta | gag | aac | caa | tta | gag | gga | aag | gtg | gag | gaa | gta | gac | 6032 |
| Lys | Lys | Leu | Glu | Asn | Gln | Leu | Glu | Gly | Lys | Val | Glu | Glu | Val | Asp | |
| | | 1885 | | | | | 1890 | | | | | 1895 | | | |

```
cta aaa cct atg aaa gaa aag aat gct aaa gaa gaa tta att agg    6077
Leu Lys Pro Met Lys Glu Lys Asn Ala Lys Glu Glu Leu Ile Arg
            1900                1905                1910 tgg gaa gaa ggt aaa aag tgg caa gcc aaa ata gaa gga att cga    6122
Trp Glu Glu Gly Lys Lys Trp Gln Ala Lys Ile Glu Gly Ile Arg
        1915                1920                1925 aac aag tta aaa gag aaa gag ggg gaa gtc ttt act tta aca aag    6167
Asn Lys Leu Lys Glu Lys Glu Gly Glu Val Phe Thr Leu Thr Lys
    1930                1935                1940 cag ttg aat act ttg aag gat ctt ttt gcc aaa gcc gat aaa gag    6212
Gln Leu Asn Thr Leu Lys Asp Leu Phe Ala Lys Ala Asp Lys Glu
1945                1950                1955 aaa ctt act ttg cag agg aaa cta aaa aca act ggc atg act gtt    6257
Lys Leu Thr Leu Gln Arg Lys Leu Lys Thr Thr Gly Met Thr Val
                1960                1965                1970 gat cag gtt ttg gga ata cga gct ttg gag tca gaa aaa gaa ttg    6302
Asp Gln Val Leu Gly Ile Arg Ala Leu Glu Ser Glu Lys Glu Leu
            1975                1980                1985 gaa gaa tta aaa aag aga aat ctt gac tta gaa aat gat ata ttg    6347
Glu Glu Leu Lys Lys Arg Asn Leu Asp Leu Glu Asn Asp Ile Leu
        1990                1995                2000 tat atg agg gcc cac caa gct ctt cct cga gat tct gtt gta gaa    6392
Tyr Met Arg Ala His Gln Ala Leu Pro Arg Asp Ser Val Val Glu
    2005                2010                2015 gat tta cat tta caa aat aga tac ctc caa gaa aaa ctt cat gct    6437
Asp Leu His Leu Gln Asn Arg Tyr Leu Gln Glu Lys Leu His Ala
2020                2025                2030 tta gaa aaa cag ttt tca aag gat aca tat tct aag cct tca att    6482
Leu Glu Lys Gln Phe Ser Lys Asp Thr Tyr Ser Lys Pro Ser Ile
                2035                2040                2045 tca gga ata gag tca gat gat cat tgt cag aga gaa cag gag ctt    6527
Ser Gly Ile Glu Ser Asp Asp His Cys Gln Arg Glu Gln Glu Leu
            2050                2055                2060 cag aag gaa aac ttg aag ttg tca tct gaa aat att gaa ctg aaa    6572
Gln Lys Glu Asn Leu Lys Leu Ser Ser Glu Asn Ile Glu Leu Lys
        2065                2070                2075 ttt cag ctt gaa caa gca aat aaa gat ttg cca aga tta aag aat    6617
Phe Gln Leu Glu Gln Ala Asn Lys Asp Leu Pro Arg Leu Lys Asn
    2080                2085                2090 caa gtc aga gat ttg aag gaa atg tgt gaa ttt ctt aag aaa gaa    6662
Gln Val Arg Asp Leu Lys Glu Met Cys Glu Phe Leu Lys Lys Glu
2095                2100                2105 aaa gca gaa gtt cag cgg aaa ctt ggc cat gtt aga ggg tct ggt    6707
Lys Ala Glu Val Gln Arg Lys Leu Gly His Val Arg Gly Ser Gly
                2110                2115                2120 aga agt gga aag aca atc cca gaa ctg gaa aaa acc att ggt tta    6752
Arg Ser Gly Lys Thr Ile Pro Glu Leu Glu Lys Thr Ile Gly Leu
            2125                2130                2135 atg aaa aaa gta gtt gaa aaa gtc cag aga gaa aat gaa cag ttg    6797
Met Lys Lys Val Val Glu Lys Val Gln Arg Glu Asn Glu Gln Leu
        2140                2145                2150 aaa aaa gca tca gga ata ttg act agt gaa aaa atg gct aat att    6842
Lys Lys Ala Ser Gly Ile Leu Thr Ser Glu Lys Met Ala Asn Ile
    2155                2160                2165 gag cag gaa aat gaa aaa ttg aag gct gaa tta gaa aaa ctt aaa    6887
Glu Gln Glu Asn Glu Lys Leu Lys Ala Glu Leu Glu Lys Leu Lys
2170                2175                2180 gct cat ctt ggg cat cag ttg agc atg cac tat gaa tcc aag acc    6932
Ala His Leu Gly His Gln Leu Ser Met His Tyr Glu Ser Lys Thr
                2185                2190                2195
```

```
aaa ggc aca gaa aaa att att gct gaa aat gaa agg ctt cgt aaa         6977
Lys Gly Thr Glu Lys Ile Ile Ala Glu Asn Glu Arg Leu Arg Lys
            2200            2205            2210 gaa ctt aaa aaa gaa act gat gct gca gag aaa tta cgg ata gca         7022
Glu Leu Lys Lys Glu Thr Asp Ala Ala Glu Lys Leu Arg Ile Ala
            2215            2220            2225 aag aat aat tta gag ata tta aat gag aag atg aca gtt caa cta         7067
Lys Asn Asn Leu Glu Ile Leu Asn Glu Lys Met Thr Val Gln Leu
            2230            2235            2240 gaa gag act ggt aag aga ttg cag ttt gca gaa agc aga ggt cca         7112
Glu Glu Thr Gly Lys Arg Leu Gln Phe Ala Glu Ser Arg Gly Pro
            2245            2250            2255 cag ctt gaa ggt gct gac agt aag agc tgg aaa tcc att gtg gtt         7157
Gln Leu Glu Gly Ala Asp Ser Lys Ser Trp Lys Ser Ile Val Val
            2260            2265            2270 aca aga atg tat gaa acc aag tta aaa gaa ttg gaa act gat att         7202
Thr Arg Met Tyr Glu Thr Lys Leu Lys Glu Leu Glu Thr Asp Ile
            2275            2280            2285 gcc aaa aaa aat caa agc att act gac ctt aaa cag ctt gta aaa         7247
Ala Lys Lys Asn Gln Ser Ile Thr Asp Leu Lys Gln Leu Val Lys
            2290            2295            2300 gaa gca aca gag aga gaa caa aaa gtt aac aaa tac aat gaa gac         7292
Glu Ala Thr Glu Arg Glu Gln Lys Val Asn Lys Tyr Asn Glu Asp
            2305            2310            2315 ctt gaa caa cag att aag att ctt aaa cat gtt cct gaa ggt gct         7337
Leu Glu Gln Gln Ile Lys Ile Leu Lys His Val Pro Glu Gly Ala
            2320            2325            2330 gag aca gag caa ggc ctt aaa cgg gag ctt caa gtt ctt aga tta         7382
Glu Thr Glu Gln Gly Leu Lys Arg Glu Leu Gln Val Leu Arg Leu
            2335            2340            2345 gct aat cat cag ctg gat aaa gag aaa gca gaa tta atc cat cag         7427
Ala Asn His Gln Leu Asp Lys Glu Lys Ala Glu Leu Ile His Gln
            2350            2355            2360 ata gaa gct aac aag gac caa agt gga gct gaa agc acc ata cct         7472
Ile Glu Ala Asn Lys Asp Gln Ser Gly Ala Glu Ser Thr Ile Pro
            2365            2370            2375 gat gct gat caa cta aag gaa aaa ata aaa gat cta gag aca cag         7517
Asp Ala Asp Gln Leu Lys Glu Lys Ile Lys Asp Leu Glu Thr Gln
            2380            2385            2390 ctc aaa atg tca gat cta gaa aag cag cat ttg aag gag gaa ata         7562
Leu Lys Met Ser Asp Leu Glu Lys Gln His Leu Lys Glu Glu Ile
            2395            2400            2405 aag aag ctg aaa aaa gaa ctg gaa aat ttt gat cct tca ttt ttt         7607
Lys Lys Leu Lys Lys Glu Leu Glu Asn Phe Asp Pro Ser Phe Phe
            2410            2415            2420 gaa gaa att gaa gat ctt aag tat aat tac aag gaa gaa gtg aag         7652
Glu Glu Ile Glu Asp Leu Lys Tyr Asn Tyr Lys Glu Glu Val Lys
            2425            2430            2435 aag aat att ctc tta gaa gag aag gta aaa aaa ctt tca gaa caa         7697
Lys Asn Ile Leu Leu Glu Glu Lys Val Lys Lys Leu Ser Glu Gln
            2440            2445            2450 ttg gga gtt gaa tta act agc cct gtt gct gct tct gaa gag ttt         7742
Leu Gly Val Glu Leu Thr Ser Pro Val Ala Ala Ser Glu Glu Phe
            2455            2460            2465 gaa gat gaa gaa gaa agt cct gtt aat ttc ccc att tac taaaggtcac     7791
Glu Asp Glu Glu Glu Ser Pro Val Asn Phe Pro Ile Tyr
            2470            2475 ctataaactt tgtttcattt aactatttat taactttata agttaaatat acttggaaat  7851
aagcagttct ccgaactgta gtatttcctt ctcactacct tgtacctta tacttagatt   7911
```

-continued

```
ggaattctta ataaataaaa ttatatgaaa ttttcaactt attaaaaaaa aaaaaaaaa    7971
a                                                                   7972
```

<210> SEQ ID NO 3
<211> LENGTH: 2479
<212> TYPE: PRT
<213> ORGANISM: Homo sapiens

<400> SEQUENCE: 3

```
Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Gly Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Lys Glu Lys Lys Val
    130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
                165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
    210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Asp Pro Ile Met Val
    290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
            340                 345                 350
```

```
Leu Gln Gln Gly Ile Gln Glu Arg Asp Ser Gln Ile Lys Met Leu Thr
            355                 360                 365
Glu Gln Val Glu Gln Tyr Thr Lys Glu Met Glu Lys Asn Thr Cys Ile
        370                 375                 380
Ile Glu Asp Leu Lys Asn Glu Leu Gln Arg Asn Lys Gly Ala Ser Thr
385                 390                 395                 400
Leu Ser Gln Gln Thr His Met Lys Ile Gln Ser Thr Leu Asp Ile Leu
                405                 410                 415
Lys Glu Lys Thr Lys Glu Ala Glu Arg Thr Ala Glu Leu Ala Glu Ala
            420                 425                 430
Asp Ala Arg Glu Lys Asp Lys Glu Leu Val Glu Ala Leu Lys Arg Leu
        435                 440                 445
Lys Asp Tyr Glu Ser Gly Val Tyr Gly Leu Glu Asp Ala Val Val Glu
    450                 455                 460
Ile Lys Asn Cys Lys Asn Gln Ile Lys Ile Arg Asp Arg Glu Ile Glu
465                 470                 475                 480
Ile Leu Thr Lys Glu Ile Asn Lys Leu Glu Leu Lys Ile Ser Asp Phe
                485                 490                 495
Leu Asp Glu Asn Glu Ala Leu Arg Glu Arg Val Gly Leu Glu Pro Lys
            500                 505                 510
Thr Met Ile Asp Leu Thr Glu Phe Arg Asn Ser Lys His Leu Lys Gln
        515                 520                 525
Gln Gln Tyr Arg Ala Glu Asn Gln Ile Leu Leu Lys Glu Ile Glu Ser
    530                 535                 540
Leu Glu Glu Glu Arg Leu Asp Leu Lys Lys Lys Ile Arg Gln Met Ala
545                 550                 555                 560
Gln Glu Arg Gly Lys Arg Ser Ala Thr Ser Gly Leu Thr Thr Glu Asp
                565                 570                 575
Leu Asn Leu Thr Glu Asn Ile Ser Gln Gly Asp Arg Ile Ser Glu Arg
            580                 585                 590
Lys Leu Asp Leu Leu Ser Leu Lys Asn Met Ser Glu Ala Gln Ser Lys
        595                 600                 605
Asn Glu Phe Leu Ser Arg Glu Leu Ile Glu Lys Glu Arg Asp Leu Glu
    610                 615                 620
Arg Ser Arg Thr Val Ile Ala Lys Phe Gln Asn Lys Leu Lys Glu Leu
625                 630                 635                 640
Val Glu Glu Asn Lys Gln Leu Glu Glu Gly Met Lys Glu Ile Leu Gln
                645                 650                 655
Ala Ile Lys Glu Met Gln Lys Asp Pro Asp Val Lys Gly Gly Glu Thr
            660                 665                 670
Ser Leu Ile Ile Pro Ser Leu Glu Arg Leu Val Asn Ala Ile Glu Ser
        675                 680                 685
Lys Asn Ala Glu Gly Ile Phe Asp Ala Ser Leu His Leu Lys Ala Gln
    690                 695                 700
Val Asp Gln Leu Thr Gly Arg Asn Glu Glu Leu Arg Gln Glu Leu Arg
705                 710                 715                 720
Glu Ser Arg Lys Glu Ala Ile Asn Tyr Ser Gln Gln Leu Ala Lys Ala
                725                 730                 735
Asn Leu Lys Ile Asp His Leu Glu Lys Glu Thr Ser Leu Leu Arg Gln
            740                 745                 750
Ser Glu Gly Ser Asn Val Val Phe Lys Gly Ile Asp Leu Pro Asp Gly
        755                 760                 765
```

```
Ile Ala Pro Ser Ser Ala Ser Ile Ile Asn Ser Gln Asn Glu Tyr Leu
770                 775                 780

Ile His Leu Leu Gln Glu Leu Glu Asn Lys Glu Lys Lys Leu Lys Asn
785                 790                 795                 800

Leu Glu Asp Ser Leu Glu Asp Tyr Asn Arg Lys Phe Ala Val Ile Arg
                805                 810                 815

His Gln Gln Ser Leu Leu Tyr Lys Glu Tyr Leu Ser Glu Lys Glu Thr
            820                 825                 830

Trp Lys Thr Glu Ser Lys Thr Ile Lys Glu Glu Lys Arg Lys Leu Glu
                835                 840                 845

Asp Gln Val Gln Gln Asp Ala Ile Lys Val Lys Glu Tyr Asn Asn Leu
850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
                885                 890                 895

Ile Arg Gln Tyr Thr Thr Leu Val Glu Leu Glu Arg Gln Leu Arg Lys
                900                 905                 910

Glu Asn Glu Lys Gln Lys Asn Glu Leu Leu Ser Met Glu Ala Glu Val
                915                 920                 925

Cys Glu Lys Ile Gly Cys Leu Gln Arg Phe Lys Glu Met Ala Ile Phe
930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
                965                 970                 975

Arg Asp Ile Leu Gln Lys Asp Asn Met Leu Val Gln Arg Thr Ser Asn
                980                 985                 990

Leu Glu His Leu Glu Cys Glu Asn Ile Ser Leu Lys Glu Gln Val Glu
                995                 1000                1005

Ser Ile Asn Lys Glu Leu Glu Ile Thr Lys Glu Lys Leu His Thr
        1010                1015                1020

Ile Glu Gln Ala Trp Glu Gln Glu Thr Lys Leu Gly Asn Glu Ser
        1025                1030                1035

Ser Met Asp Lys Ala Lys Lys Ser Ile Thr Asn Ser Asp Ile Val
        1040                1045                1050

Ser Ile Ser Lys Lys Ile Thr Met Leu Glu Met Lys Glu Leu Asn
        1055                1060                1065

Glu Arg Gln Arg Ala Glu His Cys Gln Lys Met Tyr Glu His Leu
        1070                1075                1080

Arg Thr Ser Leu Lys Gln Met Glu Glu Arg Asn Phe Glu Leu Glu
        1085                1090                1095

Thr Lys Phe Ala Glu Leu Thr Lys Ile Asn Leu Asp Ala Gln Lys
        1100                1105                1110

Val Glu Gln Met Leu Arg Asp Glu Leu Ala Asp Ser Val Ser Lys
        1115                1120                1125

Ala Val Ser Asp Ala Asp Arg Gln Arg Ile Leu Glu Leu Glu Lys
        1130                1135                1140

Asn Glu Met Glu Leu Lys Val Glu Val Ser Lys Leu Arg Glu Ile
        1145                1150                1155

Ser Asp Ile Ala Arg Arg Gln Val Glu Ile Leu Asn Ala Gln Gln
        1160                1165                1170
```

```
Gln Ser Arg Asp Lys Glu Val Glu Ser Leu Arg Met Gln Leu Leu
    1175                1180                1185
Asp Tyr Gln Ala Gln Ser Asp Glu Lys Ser Leu Ile Ala Lys Leu
    1190                1195                1200
His Gln His Asn Val Ser Leu Gln Leu Ser Glu Ala Thr Ala Leu
    1205                1210                1215
Gly Lys Leu Glu Ser Ile Thr Ser Lys Leu Gln Lys Met Glu Ala
    1220                1225                1230
Tyr Asn Leu Arg Leu Glu Gln Lys Leu Asp Glu Lys Glu Gln Ala
    1235                1240                1245
Leu Tyr Tyr Ala Arg Leu Glu Gly Arg Asn Arg Ala Lys His Leu
    1250                1255                1260
Arg Gln Thr Ile Gln Ser Leu Arg Arg Gln Phe Ser Gly Ala Leu
    1265                1270                1275
Pro Leu Ala Gln Gln Glu Lys Phe Ser Lys Thr Met Ile Gln Leu
    1280                1285                1290
Gln Asn Asp Lys Leu Lys Ile Met Gln Glu Met Lys Asn Ser Gln
    1295                1300                1305
Gln Glu His Arg Asn Met Glu Asn Lys Thr Leu Glu Met Glu Leu
    1310                1315                1320
Lys Leu Lys Gly Leu Glu Glu Leu Ile Ser Thr Leu Lys Asp Thr
    1325                1330                1335
Lys Gly Ala Gln Lys Val Ile Asn Trp His Met Lys Ile Glu Glu
    1340                1345                1350
Leu Arg Leu Gln Glu Leu Lys Leu Asn Arg Glu Leu Val Lys Asp
    1355                1360                1365
Lys Glu Glu Ile Lys Tyr Leu Asn Asn Ile Ile Ser Glu Tyr Glu
    1370                1375                1380
Arg Thr Ile Ser Ser Leu Glu Glu Ile Val Gln Gln Asn Lys
    1385                1390                1395
Phe His Glu Glu Arg Gln Met Ala Trp Asp Gln Arg Glu Val Asp
    1400                1405                1410
Leu Glu Arg Gln Leu Asp Ile Phe Asp Arg Gln Gln Asn Glu Ile
    1415                1420                1425
Leu Asn Ala Ala Gln Lys Phe Glu Glu Ala Thr Gly Ser Ile Pro
    1430                1435                1440
Asp Pro Ser Leu Pro Leu Pro Asn Gln Leu Glu Ile Ala Leu Arg
    1445                1450                1455
Lys Ile Lys Glu Asn Ile Arg Ile Ile Leu Glu Thr Arg Ala Thr
    1460                1465                1470
Cys Lys Ser Leu Glu Glu Lys Leu Lys Glu Lys Glu Ser Ala Leu
    1475                1480                1485
Arg Leu Ala Glu Gln Asn Ile Leu Ser Arg Asp Lys Val Ile Asn
    1490                1495                1500
Glu Leu Arg Leu Arg Leu Pro Ala Thr Ala Glu Arg Glu Lys Leu
    1505                1510                1515
Ile Ala Glu Leu Gly Arg Lys Glu Met Glu Pro Lys Ser His His
    1520                1525                1530
Thr Leu Lys Ile Ala His Gln Thr Ile Ala Asn Met Gln Ala Arg
    1535                1540                1545
Leu Asn Gln Lys Glu Glu Val Leu Lys Lys Tyr Gln Arg Leu Leu
    1550                1555                1560
```

```
Glu Lys Ala Arg Glu Glu Gln Arg Glu Ile Val Lys Lys His Glu
    1565                1570                1575

Glu Asp Leu His Ile Leu His His Arg Leu Glu Leu Gln Ala Asp
    1580                1585                1590

Ser Ser Leu Asn Lys Phe Lys Gln Thr Ala Trp Asp Leu Met Lys
    1595                1600                1605

Gln Ser Pro Thr Pro Val Pro Thr Asn Lys His Phe Ile Arg Leu
    1610                1615                1620

Ala Glu Met Glu Gln Thr Val Ala Glu Gln Asp Asp Ser Leu Ser
    1625                1630                1635

Ser Leu Leu Val Lys Leu Lys Lys Val Ser Gln Asp Leu Glu Arg
    1640                1645                1650

Gln Arg Glu Ile Thr Glu Leu Lys Val Lys Glu Phe Glu Asn Ile
    1655                1660                1665

Lys Leu Gln Leu Gln Glu Asn His Glu Asp Glu Val Lys Lys Val
    1670                1675                1680

Lys Ala Glu Val Glu Asp Leu Lys Tyr Leu Leu Asp Gln Ser Gln
    1685                1690                1695

Lys Glu Ser Gln Cys Leu Lys Ser Glu Leu Gln Ala Gln Lys Glu
    1700                1705                1710

Ala Asn Ser Arg Ala Pro Thr Thr Thr Met Arg Asn Leu Val Glu
    1715                1720                1725

Arg Leu Lys Ser Gln Leu Ala Leu Lys Glu Lys Gln Gln Lys Ala
    1730                1735                1740

Leu Ser Arg Ala Leu Leu Glu Leu Arg Ala Glu Met Thr Ala Ala
    1745                1750                1755

Ala Glu Glu Arg Ile Ile Ser Ala Thr Ser Gln Lys Glu Ala His
    1760                1765                1770

Leu Asn Val Gln Gln Ile Val Asp Arg His Thr Arg Glu Leu Lys
    1775                1780                1785

Thr Gln Val Glu Asp Leu Asn Glu Asn Leu Leu Lys Leu Lys Glu
    1790                1795                1800

Ala Leu Lys Thr Ser Lys Asn Arg Glu Asn Ser Leu Thr Asp Asn
    1805                1810                1815

Leu Asn Asp Leu Asn Asn Glu Leu Gln Lys Lys Gln Lys Ala Tyr
    1820                1825                1830

Asn Lys Ile Leu Arg Glu Lys Glu Glu Ile Asp Gln Glu Asn Asp
    1835                1840                1845

Glu Leu Lys Arg Gln Ile Lys Arg Leu Thr Ser Gly Leu Gln Gly
    1850                1855                1860

Lys Pro Leu Thr Asp Asn Lys Gln Ser Leu Ile Glu Glu Leu Gln
    1865                1870                1875

Arg Lys Val Lys Lys Leu Glu Asn Gln Leu Glu Gly Lys Val Glu
    1880                1885                1890

Glu Val Asp Leu Lys Pro Met Lys Glu Lys Asn Ala Lys Glu Glu
    1895                1900                1905

Leu Ile Arg Trp Glu Glu Gly Lys Lys Trp Gln Ala Lys Ile Glu
    1910                1915                1920

Gly Ile Arg Asn Lys Leu Lys Glu Lys Glu Gly Glu Val Phe Thr
    1925                1930                1935

Leu Thr Lys Gln Leu Asn Thr Leu Lys Asp Leu Phe Ala Lys Ala
    1940                1945                1950
```

```
Asp Lys Glu Lys Leu Thr Leu Gln Arg Lys Leu Lys Thr Thr Gly
1955                 1960                 1965

Met Thr Val Asp Gln Val Leu Gly Ile Arg Ala Leu Glu Ser Glu
1970                 1975                 1980

Lys Glu Leu Glu Glu Leu Lys Lys Arg Asn Leu Asp Leu Glu Asn
1985                 1990                 1995

Asp Ile Leu Tyr Met Arg Ala His Gln Ala Leu Pro Arg Asp Ser
2000                 2005                 2010

Val Val Glu Asp Leu His Leu Gln Asn Arg Tyr Leu Gln Glu Lys
2015                 2020                 2025

Leu His Ala Leu Glu Lys Gln Phe Ser Lys Asp Thr Tyr Ser Lys
2030                 2035                 2040

Pro Ser Ile Ser Gly Ile Glu Ser Asp Asp His Cys Gln Arg Glu
2045                 2050                 2055

Gln Glu Leu Gln Lys Glu Asn Leu Lys Leu Ser Ser Glu Asn Ile
2060                 2065                 2070

Glu Leu Lys Phe Gln Leu Glu Gln Ala Asn Lys Asp Leu Pro Arg
2075                 2080                 2085

Leu Lys Asn Gln Val Arg Asp Leu Lys Glu Met Cys Glu Phe Leu
2090                 2095                 2100

Lys Lys Glu Lys Ala Glu Val Gln Arg Lys Leu Gly His Val Arg
2105                 2110                 2115

Gly Ser Gly Arg Ser Gly Lys Thr Ile Pro Glu Leu Glu Lys Thr
2120                 2125                 2130

Ile Gly Leu Met Lys Lys Val Val Glu Lys Val Gln Arg Glu Asn
2135                 2140                 2145

Glu Gln Leu Lys Lys Ala Ser Gly Ile Leu Thr Ser Glu Lys Met
2150                 2155                 2160

Ala Asn Ile Glu Gln Glu Asn Glu Lys Leu Lys Ala Glu Leu Glu
2165                 2170                 2175

Lys Leu Lys Ala His Leu Gly His Gln Leu Ser Met His Tyr Glu
2180                 2185                 2190

Ser Lys Thr Lys Gly Thr Glu Lys Ile Ile Ala Glu Asn Glu Arg
2195                 2200                 2205

Leu Arg Lys Glu Leu Lys Lys Glu Thr Asp Ala Ala Glu Lys Leu
2210                 2215                 2220

Arg Ile Ala Lys Asn Asn Leu Glu Ile Leu Asn Glu Lys Met Thr
2225                 2230                 2235

Val Gln Leu Glu Glu Thr Gly Lys Arg Leu Gln Phe Ala Glu Ser
2240                 2245                 2250

Arg Gly Pro Gln Leu Glu Gly Ala Asp Ser Lys Ser Trp Lys Ser
2255                 2260                 2265

Ile Val Val Thr Arg Met Tyr Glu Thr Lys Leu Lys Glu Leu Glu
2270                 2275                 2280

Thr Asp Ile Ala Lys Lys Asn Gln Ser Ile Thr Asp Leu Lys Gln
2285                 2290                 2295

Leu Val Lys Glu Ala Thr Glu Arg Glu Gln Lys Val Asn Lys Tyr
2300                 2305                 2310

Asn Glu Asp Leu Glu Gln Gln Ile Lys Ile Leu Lys His Val Pro
2315                 2320                 2325

Glu Gly Ala Glu Thr Glu Gln Gly Leu Lys Arg Glu Leu Gln Val
2330                 2335                 2340
```

```
Leu Arg Leu Ala Asn His Gln Leu Asp Lys Glu Lys Ala Glu Leu
    2345                2350                2355

Ile His Gln Ile Glu Ala Asn Lys Asp Gln Ser Gly Ala Glu Ser
    2360                2365                2370

Thr Ile Pro Asp Ala Asp Gln Leu Lys Glu Lys Ile Lys Asp Leu
    2375                2380                2385

Glu Thr Gln Leu Lys Met Ser Asp Leu Glu Lys Gln His Leu Lys
    2390                2395                2400

Glu Glu Ile Lys Lys Leu Lys Lys Glu Leu Glu Asn Phe Asp Pro
    2405                2410                2415

Ser Phe Phe Glu Glu Ile Glu Asp Leu Lys Tyr Asn Tyr Lys Glu
    2420                2425                2430

Glu Val Lys Lys Asn Ile Leu Leu Glu Glu Lys Val Lys Lys Leu
    2435                2440                2445

Ser Glu Gln Leu Gly Val Glu Leu Thr Ser Pro Val Ala Ala Ser
    2450                2455                2460

Glu Glu Phe Glu Asp Glu Glu Ser Pro Val Asn Phe Pro Ile
    2465                2470                2475

Tyr

<210> SEQ ID NO 4
<211> LENGTH: 128
<212> TYPE: DNA
<213> ORGANISM: Homo sapiens
<220> FEATURE:
<221> NAME/KEY: misc_feature
<222> LOCATION: (1)..(128)
<223> OTHER INFORMATION: 128 nucleotide aberrant CE0290 exon

<400> SEQUENCE: 4
tagagatggg gtttcacctt gttagccagg atggtgtcga tctcctgaac tcgtgatcca    60
cccgcctcgg cctcctaaag tgctgggatt acagatgtga ccaccgcac ctggccccag   120 ttgtaatt                                                            128

<210> SEQ ID NO 5
<211> LENGTH: 997
<212> TYPE: PRT
<213> ORGANISM: Homo sapiens
<220> FEATURE:
<221> NAME/KEY: misc_feature
<222> LOCATION: (1)..(997)
<223> OTHER INFORMATION: Aberrant CEP290 polypeptide

<400> SEQUENCE: 5

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110
```

```
Leu Arg Asn Glu Ile Cys Gln Leu Glu Lys Gln Leu Glu Gln Lys Asp
            115                 120                 125
Arg Glu Leu Glu Asp Met Glu Lys Glu Leu Glu Lys Glu Lys Lys Val
        130                 135                 140
Asn Glu Gln Leu Ala Leu Arg Asn Glu Glu Ala Glu Asn Glu Asn Ser
145                 150                 155                 160
Lys Leu Arg Arg Glu Asn Lys Arg Leu Lys Lys Asn Glu Gln Leu
                165                 170                 175
Cys Gln Asp Ile Ile Asp Tyr Gln Lys Gln Ile Asp Ser Gln Lys Glu
            180                 185                 190
Thr Leu Leu Ser Arg Arg Gly Glu Asp Ser Asp Tyr Arg Ser Gln Leu
        195                 200                 205
Ser Lys Lys Asn Tyr Glu Leu Ile Gln Tyr Leu Asp Glu Ile Gln Thr
    210                 215                 220
Leu Thr Glu Ala Asn Glu Lys Ile Glu Val Gln Asn Gln Glu Met Arg
225                 230                 235                 240
Lys Asn Leu Glu Glu Ser Val Gln Glu Met Lys Met Thr Asp Glu
                245                 250                 255
Tyr Asn Arg Met Lys Ala Ile Val His Gln Thr Asp Asn Val Ile Asp
            260                 265                 270
Gln Leu Lys Lys Glu Asn Asp His Tyr Gln Leu Gln Val Gln Glu Leu
        275                 280                 285
Thr Asp Leu Leu Lys Ser Lys Asn Glu Glu Asp Asp Pro Ile Met Val
    290                 295                 300
Ala Val Asn Ala Lys Val Glu Glu Trp Lys Leu Ile Leu Ser Ser Lys
305                 310                 315                 320
Asp Asp Glu Ile Ile Glu Tyr Gln Gln Met Leu His Asn Leu Arg Glu
                325                 330                 335
Lys Leu Lys Asn Ala Gln Leu Asp Ala Asp Lys Ser Asn Val Met Ala
            340                 345                 350
Leu Gln Gln Gly Ile Gln Glu Arg Asp Ser Gln Ile Lys Met Leu Thr
        355                 360                 365
Glu Gln Val Glu Gln Tyr Thr Lys Glu Met Glu Lys Asn Thr Cys Ile
    370                 375                 380
Ile Glu Asp Leu Lys Asn Glu Leu Gln Arg Asn Lys Gly Ala Ser Thr
385                 390                 395                 400
Leu Ser Gln Gln Thr His Met Lys Ile Gln Ser Thr Leu Asp Ile Leu
                405                 410                 415
Lys Glu Lys Thr Lys Glu Ala Glu Arg Thr Ala Glu Leu Ala Glu Ala
            420                 425                 430
Asp Ala Arg Glu Lys Asp Lys Glu Leu Val Glu Ala Leu Lys Arg Leu
        435                 440                 445
Lys Asp Tyr Glu Ser Gly Val Tyr Gly Leu Glu Asp Ala Val Val Glu
    450                 455                 460
Ile Lys Asn Cys Lys Asn Gln Ile Lys Ile Arg Asp Arg Glu Ile Glu
465                 470                 475                 480
Ile Leu Thr Lys Glu Ile Asn Lys Leu Glu Leu Lys Ile Ser Asp Phe
                485                 490                 495
Leu Asp Glu Asn Glu Ala Leu Arg Glu Arg Val Gly Leu Glu Pro Lys
            500                 505                 510
Thr Met Ile Asp Leu Thr Glu Phe Arg Asn Ser Lys His Leu Lys Gln
        515                 520                 525
```

-continued

```
Gln Gln Tyr Arg Ala Glu Asn Gln Ile Leu Leu Lys Glu Ile Glu Ser
        530                 535                 540

Leu Glu Glu Glu Arg Leu Asp Leu Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
            595                 600                 605

Asn Glu Phe Leu Ser Arg Glu Leu Ile Glu Lys Glu Arg Asp Leu Glu
        610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
                645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
            675                 680                 685

Lys Asn Ala Glu Gly Ile Phe Asp Ala Ser Leu His Leu Lys Ala Gln
        690                 695                 700

Val Asp Gln Leu Thr Gly Arg Asn Glu Glu Leu Arg Gln Glu Leu Arg
705                 710                 715                 720

Glu Ser Arg Lys Glu Ala Ile Asn Tyr Ser Gln Gln Leu Ala Lys Ala
                725                 730                 735

Asn Leu Lys Ile Asp His Leu Glu Lys Glu Thr Ser Leu Leu Arg Gln
            740                 745                 750

Ser Glu Gly Ser Asn Val Val Phe Lys Gly Ile Asp Leu Pro Asp Gly
            755                 760                 765

Ile Ala Pro Ser Ser Ala Ser Ile Ile Asn Ser Gln Asn Glu Tyr Leu
        770                 775                 780

Ile His Leu Leu Gln Glu Leu Glu Asn Lys Glu Lys Lys Leu Lys Asn
785                 790                 795                 800

Leu Glu Asp Ser Leu Glu Asp Tyr Asn Arg Lys Phe Ala Val Ile Arg
                805                 810                 815

His Gln Gln Ser Leu Leu Tyr Lys Glu Tyr Leu Ser Glu Lys Glu Thr
            820                 825                 830

Trp Lys Thr Glu Ser Lys Thr Ile Lys Glu Glu Lys Arg Lys Leu Glu
            835                 840                 845

Asp Gln Val Gln Gln Asp Ala Ile Lys Val Lys Glu Tyr Asn Asn Leu
        850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
                885                 890                 895

Ile Arg Gln Tyr Thr Thr Leu Val Glu Leu Glu Arg Gln Leu Arg Lys
            900                 905                 910

Glu Asn Glu Lys Gln Lys Asn Glu Leu Leu Ser Met Glu Ala Glu Val
            915                 920                 925

Cys Glu Lys Ile Gly Cys Leu Gln Arg Phe Lys Glu Met Ala Ile Phe
        930                 935                 940
```

```
Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
            965                 970                 975

Arg Asp Ile Leu Gln Lys Asp Asn Met Leu Val Gln Arg Thr Ser Asn
        980                 985                 990

Leu Glu His Leu Glu
        995

<210> SEQ ID NO 6
<211> LENGTH: 143
<212> TYPE: DNA
<213> ORGANISM: Homo sapiens
<220> FEATURE:
<221> NAME/KEY: misc_feature
<222> LOCATION: (1)..(143)
<223> OTHER INFORMATION: 143 nucleotide motif

<400> SEQUENCE: 6
tagagatggg gtttcacctt gttagccagg atggtgtcga tctcctgaac tcgtgatcca      60
cccgcctcgg cctcctaaag tgctgggatt acagatgtga gccaccgcac ctggccccag     120
ttgtaattgt gaatatctca tac                                             143

<210> SEQ ID NO 7
<211> LENGTH: 42
<212> TYPE: DNA
<213> ORGANISM: Homo sapiens
<220> FEATURE:
<221> NAME/KEY: misc_feature
<222> LOCATION: (1)..(42)
<223> OTHER INFORMATION: 42 nucleotide motif

<400> SEQUENCE: 7
acagatgtga gccaccgcac ctggccccag ttgtaattgt ga                         42

<210> SEQ ID NO 8
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 24 nucleotide motif

<400> SEQUENCE: 8
ccaccgcacc tggccccagt tgta                                             24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-1

<400> SEQUENCE: 9
taatcccagc actttaggag                                                  20

<210> SEQ ID NO 10
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: AON-2

<400> SEQUENCE: 10
gggccaggtg cggtgg                                                   16

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-3

<400> SEQUENCE: 11
aactggggcc aggtgcg                                                  17

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-4

<400> SEQUENCE: 12
tacaactggg gccaggtg                                                 18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-5

<400> SEQUENCE: 13
actcacaatt acaactgggg                                               20

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SON-3

<400> SEQUENCE: 14
cgcacctggc cccagtt                                                  17

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      PCR primer
```

```
<400> SEQUENCE: 15
tgctaagtac agggacatct tgc                                              23

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 16
agactccact tgttctttta aggag                                            25

<210> SEQ ID NO 17
<211> LENGTH: 36
<212> TYPE: DNA
<213> ORGANISM: Homo sapiens

<400> SEQUENCE: 17
cacctggccc cagttgtaat tgtgaatatc tcatac                                36

<210> SEQ ID NO 18
<211> LENGTH: 36
<212> TYPE: RNA
<213> ORGANISM: Homo sapiens

<400> SEQUENCE: 18
caccuggccc caguuguaau gugaauauc ucauac                                 36

<210> SEQ ID NO 19
<211> LENGTH: 36
<212> TYPE: DNA
<213> ORGANISM: Homo sapiens

<400> SEQUENCE: 19
cacctggccc cagttgtaat tgtgagtatc tcatac                                36

<210> SEQ ID NO 20
<211> LENGTH: 36
<212> TYPE: RNA
<213> ORGANISM: Homo sapiens

<400> SEQUENCE: 20
caccuggccc caguuguaau gugaguauc ucauac                                 36

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
auacuacuaa uuacaacugg g                                                21
```